(12) United States Patent
Matsuoka et al.

(10) Patent No.: US 8,217,031 B2
(45) Date of Patent: Jul. 10, 2012

(54) HETEROARYL DERIVATIVES

(75) Inventors: Masato Matsuoka, Otsu (JP); Tatsuya Oyama, Magaokakyo (JP)

(73) Assignee: Nippon Shinyaku Co., Ltd., Kyoto (JP)

( * ) Notice: Subject to any disclaimer, the term of this patent is extended or adjusted under 35 U.S.C. 154(b) by 375 days.

(21) Appl. No.: 12/593,566

(22) PCT Filed: Mar. 28, 2008

(86) PCT No.: PCT/JP2008/056217
§ 371 (c)(1),
(2), (4) Date: Sep. 28, 2009

(87) PCT Pub. No.: WO2008/120761
PCT Pub. Date: Oct. 9, 2008

(65) Prior Publication Data
US 2010/0048537 A1 Feb. 25, 2010

(30) Foreign Application Priority Data

Mar. 30, 2007 (JP) ................................ 2007-094548
May 31, 2007 (JP) ................................ 2007-146039

(51) Int. Cl.
*A61K 31/55* (2006.01)
*C07D 223/16* (2006.01)
(52) U.S. Cl. ...................................... 514/215; 540/593
(58) Field of Classification Search .................. None
See application file for complete search history.

(56) References Cited

U.S. PATENT DOCUMENTS

| 4,065,460 A | 12/1977 | Heymes et al. |
| 4,076,819 A | 2/1978 | Maffrand |
| 2006/0003990 A1 | 1/2006 | Bennani et al. |

FOREIGN PATENT DOCUMENTS

| JP | 51149297 A | 12/1976 |
| JP | 52000294 A | 1/1977 |
| WO | 2006004931 A2 | 1/2006 |
| WO | 2006082354 A1 | 8/2006 |

OTHER PUBLICATIONS

Kent et al., "SNaRIs, NaSSAs, and NaRIs: new agents for the treatment of depression", Lancet, vol. 355, Mar. 11, 2000.
Philippe Tremblay and Pierre Blier et al., "Catecholaminergic Strategies for the Treatment of Major Depression", Current Drug Targets, 2006, 7, 149-158.
Jean-Marc Cloos et al., "The treatment of panic disorder" Curr Opin Psychiatry 18:45-50; 2005.
Sohita Dhillon et al., "Escitalopram: a review of its use in the management of anxiety disorders", CNS Drugs 2006; 20(9): 763-790.
Kunitoshi Kamijima et al., "Effectivness of paroxetine in the treatment of obsessive-compulsive disorders", Expert Rev. Neurotherapeutics 6(7), 945-956; 2006.
Dale R. Grothe et al., "Treatment of pain syndromes with venlafaxine", Pharmacotherapy 2004; 24(5): 621-629.
Daniel S. Rooks et al., "Fibromyalgia treatment update", Curr Opin. Rheumatol 19: 11-117; 2007.
Vojtech Hainer et al., "Serotonin and Norepinephrine Reuptake Inhibition and Eating Behavior", Ann. N.Y. Acad. Sci. 1083: 252-269 (2006).
Paramananthan Mariappan et al., "Duloxetine, a Serotonin and Noradrenaline Reuptake Inhibitor (SNRI) for the Treatment of Stress Urinary Incontinence: A Systematic Review", European Urology 51 (2007) 67-74.
Bob Djavan et al., "Pretreatment prostate-specific antigen as an outcome predictor of targeted transurethral microwave thermotherapy", Urology 55: 51-57; 2000.
Beth A. Sproule et al., "Selective Serotonin Reuptake Inhibitors and CNS Drug Interactions", Clin. Pharmacokiner. 1997; 456-471.

*Primary Examiner* — Noble Jarrell
(74) *Attorney, Agent, or Firm* — McDermott Will & Emery LLP

(57) ABSTRACT

The present invention relates to a compound represented by formula [1] or a pharmaceutically acceptable salt thereof:

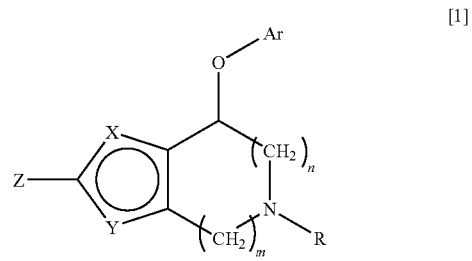

In formula [1], one of X and Y is CH and the other is oxygen or sulfur; R is hydrogen, etc.; Z is hydrogen, etc.; Ar is phenyl, etc.; and n is 1 or 2 and or m is 1 or 2, excluding compounds where n is 2 and m is 2 simultaneously. Also provided is a pharmaceutical composition comprising a compound of formula [1] or a pharmaceutically acceptable salt thereof as an active ingredient. The composition is usable as an agent for the prevention or treatment of depression, panic disorder, anxiety, obsessive-compulsive disorder, chronic pain, fibromyalgia, obesity, stress urinary incontinence, and overactive bladder.

10 Claims, No Drawings

HETEROARYL DERIVATIVES

This application is the U.S. national phase application under 35 U.S.C. §371 of International Patent Application No. PCT/JP2008/056217 filed Mar. 28, 2008, which claims the benefit of priority to Japanese Patent Application No. 2007-094548 filed Mar. 30, 2007 and Japanese Patent Application No. 2007-146039 filed May 31, 2007, the disclosures of all of which are hereby incorporated by reference in their entireties. The International Application was published in Japanese on Oct. 9, 2008 as WO 2008/120761.

FIELD OF THE INVENTION

The present invention relates to a novel heteroaryl derivative and a pharmaceutical composition comprising the heteroaryl derivative as an active ingredient.

BACKGROUND

Neuronal signal transduction is carried out by such a manner that a neurotransmitter such as serotonin and norepinephrine is released from the terminal of presynaptic neuron and binds to various receptors on the postsynaptic neuronal plasma membrane (synaptic transmission). For the next synaptic transmission, the neurotransmitter existing in the synaptic cleft is subjected to reuptake via an uptake site existing in the presynaptic nerve terminal.

When the reuptake is inhibited, concentration of the neurotransmitter in the synaptic cleft becomes high whereby stronger signal transduction takes place.

At present, many compounds having a serotonin reuptake inhibiting activity and a norepinephrine reuptake inhibiting activity have been known. Those known compounds inhibit the reuptake of serotonin and norepinephrine in presynaptic cell membranes whereby various pharmacological effects are exerted and they are used as therapeutic agents for various diseases throughout the world (refer, for example, to NPL 1).

Examples of specific indications by serotonin and norepinephrine reuptake inhibitors include depression, panic disorder, anxiety, obsessive-compulsive disorder, chronic pain, fibromyalgia, obesity, stress urinary incontinence, and overactive bladder (NPL 2 to NPL 10).

[NPL 1] Kent J M, Lancet, 355, 911-918, 2000
[NPL 2] Tremblay P and Blier P, Curr Drug Targets, 7(2), 149-158, 2006
[NPL 3] Cloos J M, Curr Opin Psychiatry, 18(1), 45-50, 2005
[NPL 4] Dhillon S et al., CNS Drugs, 20(9), 763-790, 2006
[NPL 5] Kamijima K and Aoki M, Expert Rev Neurother, 6(7), 945-956, 2006
[NPL 6] Grothe D R et al., Pharmacotherapy, 24(5), 621-629, 2004
[NPL 7] Rooks D S, Curr Opin Rheumatol, 19(2), 111-117, 2007
[NPL 8] Hainer V et al., Ann N Y Acad. Sci., 1083, 252-269, 2006
[NPL 9] Mariappan P et al., Eur Urol., 51(1), 67-74, 2007
[NPL 10] Andersson K E, Urology, 55(5A Suppl), 51-57, 2000

DETAILED DESCRIPTION OF THE INVENTION

A main object of the present invention is to provide a novel heteroaryl derivative. Another object of the present invention is to provide a pharmaceutical composition comprising the heteroaryl derivative as an active ingredient.

The present invention can include the compounds mentioned in the following (1) to (15).

(1) A compound represented by the following formula [1] (hereinafter, referred to as "the compound of the present invention") or a pharmaceutically acceptable salt thereof.

Chemical Scheme 1

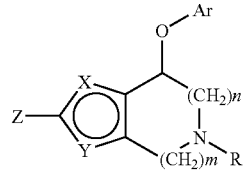

[1]

In the formula [1]:

Either of X and Y is CH and the other is oxygen or sulfur;

R represents hydrogen, dialkylaminoacetyl or alkyl which may be substituted with one to three substituents selected from the group consisting of cycloalkyl, alkenyl, halogen, cyano, amino, dialkylamino, alkoxycarbonyl, pyridyl, alkoxy and hydroxy;

Z represents hydrogen, alkyl, halogen, nitrile or phenyl which may be substituted with one to three substituents selected from the group consisting of alkyl, alkoxy and halogen;

Ar represents phenyl, naphthyl, pyridyl, quinolyl, isoquinolyl, indolyl, carbazolyl, dibenzofuranyl, benzothienyl or benzofuranyl, each of which may be substituted with one to three substituents selected from the group consisting of alkyl, hydroxyalkyl, alkoxy, halogen, haloalkyl, haloalkoxy, nitro, cyano, phenyl, aminocarbonyl, benzyloxy, benzyloxycarbonyl, hydroxycarbonyl, methoxycarbonyl, methanesulfonyl, amino, acetylamino, phthalimido, acetyl, monoalkylaminocarbonyl and dialkylaminocarbonyl;

when Ar is an optionally substituted phenyl, the phenyl as such may be condensed with a cyclopentane ring, a cyclohexane ring or a dioxolane ring; and n is 1 or 2 and m is 1 or 2, excluding the compounds where n is 2 and m is 2 simultaneously.

(2) The compound according to the above (1) or a pharmaceutically acceptable salt thereof,
wherein, in the formula [1]:
either of X and Y is CH and the other is oxygen.

(3) The compound according to the above (1) or a pharmaceutically acceptable salt thereof,
wherein, in the formula [1]:
either of X and Y is CH and the other is sulfur.

(4) The compound according to the above (1) or a pharmaceutically acceptable salt thereof,
wherein, in the formula [1]:
n is 1 and m is 1.

(5) The compound according to the above (1) or a pharmaceutically acceptable salt thereof,
wherein, in the formula [1]:
n is 1 and m is 2 or n is 2 and m is 1.

(6) The compound according to any one of the above (1) to (5) or a pharmaceutically acceptable salt thereof,
wherein, in the formula [1]:
R is hydrogen or alkyl which may be substituted with one to three substituents selected from the group consisting of cycloalkyl, alkenyl, halogen, cyano, amino, dialkylamino, alkoxycarbonyl, pyridyl, alkoxy and hydroxy.

(7) The compound according to any one of the above (1) to (5) or a pharmaceutically acceptable salt thereof,
wherein, in the formula [1]:
Z is hydrogen, alkyl, halogen or nitrile.

(8) The compound according to any one of the above (1) to (5) or a pharmaceutically acceptable salt thereof,
wherein, in the formula [1]:
Z is hydrogen or alkyl.

(9) The compound according to any one of the above (1) to (5) or a pharmaceutically acceptable salt thereof,
wherein, in the formula [1]:
Ar is phenyl, naphthyl or pyridyl, each of which may be substituted with one to three substituents selected from the group consisting of alkyl, hydroxyalkyl, alkoxy, halogen, haloalkyl, haloalkoxy, nitro, cyano, phenyl, aminocarbonyl, benzyloxy, benzyloxycarbonyl, hydroxycarbonyl, methoxycarbonyl, methanesulfonyl, amino, acetylamino, phthalimido, acetyl, monoalkylaminocarbonyl and dialkylaminocarbonyl; and
when Ar is an optionally substituted phenyl, the phenyl as such may be condensed with a cyclopentane ring, a cyclohexane ring or a dioxolane ring.

(10) The compound according to any one of the above (1) to (5) or a pharmaceutically acceptable salt thereof,
wherein, in the formula [1]:
Ar is phenyl, naphthyl or pyridyl, each of which may be substituted with one to three substituents selected from the group consisting of alkyl, halogen, aminocarbonyl and dialkylaminocarbonyl.

(11) The compound according to the above (2) or a pharmaceutically acceptable salt thereof,
wherein, in the formula [1]:
R is hydrogen or alkyl which may be substituted with one to three substituents selected from the group consisting of cycloalkyl, alkenyl, halogen, cyano, amino, dialkylamino, alkoxycarbonyl, pyridyl, alkoxy and hydroxy; Z is hydrogen or alkyl;
Ar is phenyl, naphthyl or pyridyl, each of which may be substituted with one to three substituents selected from the group consisting of alkyl, halogen, aminocarbonyl and dialkylaminocarbonyl; and
n is 1 and m is 1.

(12) The compound according to the above (2) or a pharmaceutically acceptable salt thereof,
wherein, in the formula [1]:
R is hydrogen or alkyl which may be substituted with one to three substituents selected from the group consisting of cycloalkyl, alkenyl, halogen, cyano, amino, dialkylamino, alkoxycarbonyl, pyridyl, alkoxy and hydroxy;
Z is hydrogen or alkyl;
Ar is phenyl, naphthyl or pyridyl, each of which may be substituted with one to three substituents selected from the group consisting of alkyl, halogen, aminocarbonyl and dialkylaminocarbonyl; and
n is 1 and m is 2, or n is 2 and m is 1.

(13) The compound according to the above (3) or a pharmaceutically acceptable salt thereof,
wherein, in the formula [1]:
R is hydrogen or alkyl which may be substituted with one to three substituents selected from the group consisting of cycloalkyl, alkenyl, halogen, cyano, amino, dialkylamino, alkoxycarbonyl, pyridyl, alkoxy and hydroxy;
Z is hydrogen or alkyl;
Ar is phenyl, naphthyl or pyridyl, each of which may be substituted with one to three substituents selected from the group consisting of alkyl, halogen, aminocarbonyl and dialkylaminocarbonyl; and
n is 1 and m is 1.

(14) The compound according to the above (3) or a pharmaceutically acceptable salt thereof,
wherein, in the formula [1]:
R is hydrogen or alkyl which may be substituted with one to three substituents selected from the group consisting of cycloalkyl, alkenyl, halogen, cyano, amino, dialkylamino, alkoxycarbonyl, pyridyl, alkoxy and hydroxy;
Z is hydrogen or alkyl;
Ar is phenyl, naphthyl or pyridyl, each of which may be substituted with one to three substituents selected from the group consisting of alkyl, halogen, aminocarbonyl and dialkylaminocarbonyl; and
n is 1 and m is 2, or n is 2 and m is 1.

(15) The compound according to the above (1) or a pharmaceutically acceptable salt thereof, which compound is selected from the group consisting of the following (1a) to (25a).

(1a) 5-methyl-7-(naphthalen-1-yloxy)-4,5,6,7-tetrahydrothieno[3,2-c]pyridine (2a) 4-(3,4-dichlorophenyloxy)-6-ethyl-4,5,6,7-tetrahydrothieno[2,3-c]pyridine, (3a) 4-(3,4-dichlorophenyloxy)-2,6-dimethyl-4,5,6,7-tetrahydrofuro[2,3-c]pyridine, (4a) 4-(4-bromo-3-chlorophenyloxy)-6-methyl-4,5,6,7-tetrahydrofuro[2,3-c]pyridine, (5a) 4-(4-chloronaphthalen-1-yloxy)-2,6-dimethyl-4,5,6,7-tetrahydrofuro[2,3-c]pyridine, (6a) 4-(3,4-dibromophenyloxy)-2,6-dimethyl-4,5,6,7-tetrahydrothieno[2,3-c]pyridine, (7a) 2,7-dimethyl-4-(naphthalen-1-yloxy)-5,6,7,8-tetrahydro-4H-thieno[2,3-c]azepine (8a) 8-(3,4-dichlorophenyloxy)-5-methyl-5,6,7,8-tetrahydro-4H-thieno[3,2-c]azepine, (9a) 6-methyl-4-(naphthalen-1-yloxy)-5,6,7,8-tetrahydro-4H-thieno[2,3-d]azepine, (10a) 8-(4-chloronaphthalen-1-yloxy)-5-methyl-5,6,7,8-tetrahydro-4H-thieno[3,2-c]azepine, (11a) 4-(3,4-dibromophenyloxy)-2,7-dimethyl-5,6,7,8-tetrahydro-4H-thieno[2,3-c]azepine, (12a) 2,7-dimethyl-4-(naphthalen-1-yloxy)-5,6,7,8-tetrahydro-4H-furo[2,3-c]azepine, (13a) 4-(2,3-dichlorophenyloxy)-2,7-dimethyl-5,6,7,8-tetrahydro-4H-thieno[2,3-c]azepine, (14a) 4-(2,3-dichlorophenyloxy)-7-methyl-5,6,7,8-tetrahydro-4H-thieno[2,3-c]azepine, (15a) 5-methyl-8-(naphthalen-1-yloxy)-5,6,7,8-tetrahydro-4H-furo[3,2-c]azepine, (16a) 4-(2,3-dichlorophenyloxy)-2,7-dimethyl-5,6,7,8-tetrahydro-4H-furo[2,3-c]azepine, (17a) 8-(2,3-dichlorophenyloxy)-5-methyl-5,6,7,8-tetrahydro-4H-furo[3,2-c]azepine, (18a) 4-(3-bromo-2-chlorophenyloxy)-7-methyl-5,6,7,8-tetrahydro-4H-furo[2,3-c]azepine, (19a) 7-methyl-4-(naphthalen-1-yloxy)-5,6,7,8-tetrahydro-4H-furo[2,3-c]azepine, (20a) 4-(2,3-dichlorophenyloxy)-7-methyl-5,6,7,8-tetrahydro-4H-furo[2,3-c]azepine, (21a) 4-(3-bromo-2-chlorophenyloxy)-2,7-dimethyl-5,6,7,8-tetrahydro-4H-furo[2,3-c]azepine, (22a) 4-(2-chloro-4-carbamoylphenyloxy)-7-methyl-5,6,7,8-tetrahydro-4H-furo[2,3-c]azepine, (23a) (+)-4-(3-bromo-2-chlorophenoxy)-7-methyl-5,6,7,8-tetrahydro-4H-furo[2,3-c]azepine, (24a) (+)-4-(2,3-dichlorophenoxy)-7-methyl-5,6,7,8-tetrahydro-4H-furo[2,3-c]azepine, and (25a) (+)-2,7-dimethyl-4-(naphthalen-1-yloxy)-5,6,7,8-tetrahydro-4H-furo[2,3-c]azepine.

A pharmaceutical composition comprising the compound of the present invention or a pharmaceutically acceptable salt thereof as an active ingredient is able to be used as a preventive or a therapeutic agent for depression, panic disorder, anxiety, obsessive-compulsive disorder, chronic pain, fibromyalgia, obesity, stress urinary incontinence or overactive bladder.

The present invention will now be illustrated in detail as follows.

Examples of the "alkyl" include a liner or branched alkyl having 1 to 10 carbon(s) or, to be more specific, methyl, ethyl, n-propyl, isopropyl, n-butyl, isobutyl, sec-butyl, tert-butyl, n-pentyl, isopentyl, n-hexyl, isohexyl, n-heptyl, isoheptyl, n-octyl, n-nonyl and n-decyl. Among the above, alkyl having 1 to 6 carbon(s) is preferable and alkyl having 1 to 4 carbon(s) is more preferable.

Examples of the alkyl moiety of "hydroxyalkyl", "dialkylamino", "monoalkylaminocarbonyl", "dialkylaminocarbonyl", "dialkylaminoacetyl" and "alkoxycarbonyl" include the same alkyl as described above.

Examples of the "alkoxy" include a liner or branched alkoxy having 1 to 10 carbon(s) or, to be more specific, methoxy, ethoxy, n-propoxy, isopropoxy, n-butoxy, isobutoxy, sec-butoxy, tert-butoxy, n-pentyloxy, isopentyloxy, n-hexyloxy, isohexyloxy, n-heptyloxy, isoheptyloxy, n-octyloxy, n-nonyloxy and n-decyloxy. Among the above, alkoxy having 1 to 6 carbon(s) is preferable and alkoxy having 1 to 4 carbon(s) is more preferable.

Examples of the "cycloalkyl" include a mono- to tricyclic cycloalkyl having 3 to 10 carbons or, to be more specific, cyclopropyl, cyclobutyl, cyclopentyl, cyclohexyl, cycloheptyl, cyclooctyl, cyclononyl and cyclodecanyl. Among the above, cycloalkyl having 4 to 9 carbons is preferable and cycloalkyl having 5 to 8 carbons is more preferable.

Examples of the "alkenyl" include a linear or branched alkenyl having 2 to 8 carbons or, to be more specific, vinyl, propenyl, butenyl, pentenyl, hexenyl, heptenyl and octenyl. Among the above, alkenyl having 2 to 6 carbons is preferable and alkenyl having 2 to 4 carbons is more preferable.

Examples of the "halogen" include fluorine, chlorine, bromine and iodine.

Examples of the "haloalkyl" include an alkyl where hydrogen(s) is/are substituted at 1 to 3-position(s) thereof with halogen, namely, monohaloalkyl, dihaloalkyl and trihaloalkyl.

Examples of the alkyl moiety of the "haloalkyl" include the same alkyl as described above.

Examples of the halogen moiety of the "haloalkyl" include halogen described above.

Examples of the "haloalkoxy" include an alkoxy where 1 to 3-position(s) of the alkyl moiety thereof is/are substituted with halogen(s), namely, monohaloalkoxy, dihaloalkoxy and trihaloalkoxy.

Examples of the alkoxy moiety of the "haloalkoxy" include the same alkoxy as described above.

Examples of the halogen moiety of the "haloalkoxy" include the same halogen as described above.

Examples of the "naphthyl" include 1-naphthyl and 2-naphthyl.

Examples of the "pyridyl" include 2-pyridyl, 3-pyridyl and 4-pyridyl.

Examples of the "quinolyl" include 2-quinolyl, 3-quinolyl, 4-quinolyl, 5-quinolyl, 6-quinolyl, 7-quinolyl and 8-quinolyl.

Examples of the "isoquinolyl" in the present invention include 1-isoquinoly, 3-isoquinolyl, 4-isoquinolyl, 5-isoquinolyl, 6-isoquinolyl, 7-isoquinolyl and 8-isoquinolyl.

Examples of the "indolyl" include 1-indolyl, 2-indolyl, 3-indolyl, 4-indolyl, 5-indolyl, 6-indolyl and 7-indolyl.

Examples of the "carbazolyl" include 1-carbazolyl, 2-carbazolyl, 3-carbazolyl, 4-carbazolyl and 9-carbazolyl.

Examples of the "dibenzofuranyl" include 1-dibenzofuranyl, 2-dibenzofuranyl, 3-dibenzofuranyl and 4-dibenzofuranyl.

Examples of the "benzothienyl" include 2-benzothienyl, 3-benzothienyl, 4-benzothienyl, 5-benzothienyl, 6-benzothienyl and 7-benzothienyl.

Examples of the "benzofuranyl" include 2-benzofuranyl, 3-benzolfuranyl, 4-benzofuranyl, 5-benzofuranyl, 6-benzofuranyl and 7-benzofuranyl.

The compound of the present invention is able to be produced from a known compound or an intermediate which is able to be easily prepared by, for example, the following production process 1. When the material has a substituent which may affect the reaction in the production of the compound of the present invention, it is usual that the reaction is conducted after the material is modified to include appropriate protective groups by a conventional method. The protective group is able to be removed by a conventional method after the reaction.

Production Process 1

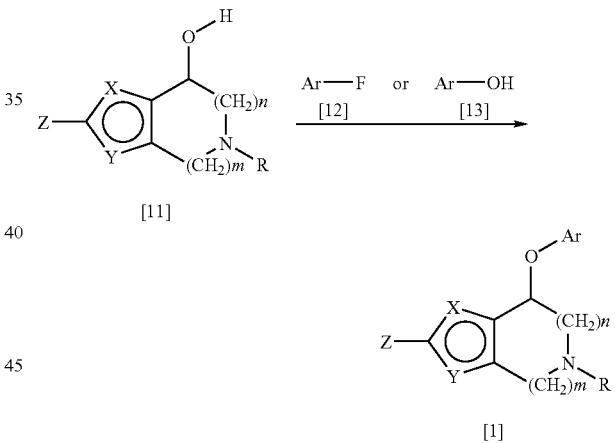

In the formulae, X, Y, Z, R, Ar, n and m have the same meanings as mentioned above.

Since the present reaction is a condensation reaction of a compound [11] with a compound [12] or [13], it is able to be carried out by a method which has been known per se as a condensation reaction. A compound [1] is able to be produced by the reaction of the compound [12] or [13] with the compound [11].

When the compound [12] is used, a condensing agent (such as potassium benzoate) is used and the reaction is able to be conducted at a temperature within the range of −20° C. to 100° C. in the presence or absence of a base (such as sodium hydride and potassium hydride). The solvent usable therefor is not specifically limited so far as it does not participate in the reaction and examples thereof include amides such as N,N-dimethylformamide (DMF) and N,N-dimethylacetamide; ethers such as tetrahydrofuran (THF) and diethyl ether; nitriles such as acetonitrile and propionitrile; hydrocarbons such as benzene and toluene; halogenated hydrocarbons such as chloroform and methylene chloride; sulfoxide such as dimethyl sulfoxide (DMSO); and a mixture thereof. Reaction time may vary depending upon the type of material and condensing agent, the reaction temperature, etc. and, usually, it is appropriate to be within the range of 30 minutes to 24 hours. Amounts of the compound [12] and the condensing agent used therefor are preferable within the range of 1 to 3 times molar quantities relative to the compound [11].

When the compound [13] is used, various kinds of azodicarboxylate (such as diethyl azodicarboxylate (DEAD) and diisopropyl azodicarboxylate (DIAD)) may be used as a condensing agent and the reaction may be conducted in the presence of trialkylphosphine or triarylphosphine (such as tributylphosphine and triphenylphosphine) at a temperature within the range of −20 to 100° C. The solvent usable therefor is not specifically limited so far as it does not participate in the reaction and examples thereof include amides such as DMF and N,N-dimethylacetamide; ethers such as THF and diethyl ether; nitrites such as acetonitrile and propionitrile; hydrocarbons such as benzene and toluene; halogenated hydrocarbons such as chloroform and methylene chloride; sulfoxide such as DMSO; and a mixture thereof. Reaction time may vary depending upon the type of material and condensing agent, the reaction temperature, etc. and, usually, it is appropriate to be within the range of 30 minutes to 24 hours. Amounts of the compound [13] and the condensing agent are preferable within the range of 1 to 3 times molar quantities relative to the compound [11].

Production Process 1-1: Production Process for the Material Compound (11)

The material compound [11] is able to be produced by a conventional method. To be more specific, the compound [11] is able to be produced by the following process.

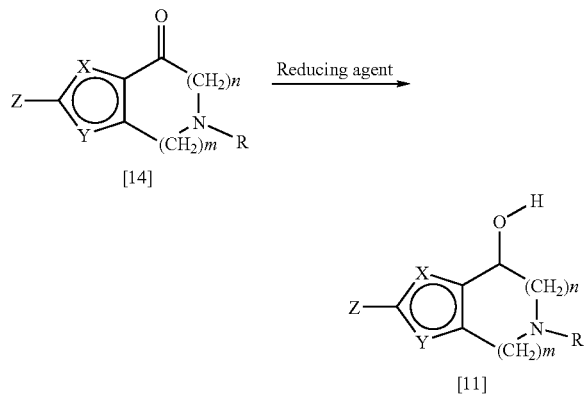

Chemical Scheme 3

In the formulae, X, Y, Z, R, Ar, n and m have the same meanings as mentioned above This reaction is a reducing reaction of a ketone group of the compound [14] to an alcohol group and, therefore, it is able to be carried out by a method which has been known per se as a reducing reaction.

The present reaction is able to be conducted using an appropriate reducing agent (such as lithium aluminum hydride, sodium borohydride, lithium borohydride, sodium cyanoborohydride and borane). It is also possible to use a catalytic reduction method using, for example, platinum, Raney nickel, platinum-carbon (Pt—C), palladium-carbon (Pd—C) or ruthenium complex as a catalyst whereby a ketone group is able to be hydrogenated. It is also possible in this reaction to produce the optically active compound [11] using an appropriate asymmetric ligand (such as (R)-2,2'-bis(diphenylphosphino)-1,1'-binaphthyl ((R)-BINAP), (S)-2,2'-bis(diphenylphosphino)-1,1'-binaphthyl ((S)-BINAP), (R)-2,2'-bis(di-p-tolylphosphino)-1,1'-binaphthyl ((R)-Tol-BINAP), (S)-2,2'-bis(di-p-tolylphosphino)-1,1'-binaphthyl ((S)-Tol-BINAP), (R)-1,1'-bis(p-methoxyphenyl)-2-isopropyl-1,2-ethanediamine ((R)-DAIPEN), (S)-1,1'-bis(p-methoxyphenyl)-2-isopropyl-1,2-ethanediamine ((S)-DAIPEN), (R)-1,2-diphenyl-1,2-ethanediamine ((R)-DPEN), (S)-1,2-diphenyl-1,2-ethanediamine ((S)-DPEN), (R)—N-(p-toluenesulfonyl)-1,2-diphenyl-1,2-ethanediamine ((R)-TsDPEN), (S)—N-(p-toluenesulfonyl)-1,2-diphenyl-1,2-ethanediamine ((S)-TsDPEN), (R)—N-(methanesulfonyl)-1,2-diphenyl-1,2-ethanediamine ((R)-MsDPEN) or (S)—N-(methanesulfonyl)-1,2-diphenyl-1,2-ethanediamine ((S)-MsDPEN)) and an asymmetric reducing catalyst (such as chloro[(1S,2S)—N-(p-toluenesulfonyl)-1,2-diphenylethanediamine](p-cymene)ruthenium(II), chloro[(1R,2R)—N-(p-toluenesulfonyl)-1,2-diphenyl-1,2-ethanediamine](p-cymene) ruthenium(II), chloro[(1S,2S)—N-(p-toluenesulfonyl)-1,2-diphenyl-1,2-ethanediamine](mesitylene)ruthenium(II), chloro[(1R,2R)—N-(p-toluenesulfonyl)-1,2-diphenyl-1,2-ethanediamine](mesitylene)ruthenium(II), chloro[(1S,2S)—N-(p-toluenesulfonyl)-1,2-diphenyl-1,2-ethanediamine](hexamethylbenzene)ruthenium(II), chloro[(1R,2R)—N-(p-toluenesulfonyl)-1,2-diphenyl-1,2-ethanediamine](hexamethylbenzene)ruthenium(II), chloro[(1S,2S)—N-(methanesulfonyl)-1,2-diphenyl-1,2-ethanediamine](p-cymene)ruthenium(II), chloro[(1R,2R)—N-(methanesulfonyl)-1,2-diphenyl-1,2-ethanediamine](p-cymene)ruthenium(II), [(1S,2S)—N-(p-toluenesulfonyl)-1,2-diphenyl-1,2-ethanediamine](p-cymene)ruthenium(II), [(1R,2R)—N-(p-toluenesulfonyl)-1,2-diphenyl-1,2-ethanediamine](p-cymene)ruthenium(II), [(1S,2S)—N-(p-toluenesulfonyl)-1,2-diphenyl-1,2-ethanediamine](mesitylene)ruthenium(II) hydride and [(1R,2R)—N-(p-toluenesulfonyl)-1,2-diphenyl-1,2-ethanediamine](mesitylene)ruthenium(II) hydride).

Production Process 1-1-1: Production Process for the Material Compound [14]

The material compound [14] is able to be produced according to a method mentioned, for example, in Chemistry Letters, 1980, 1389, J. Heterocyclic Chem., 13, 1347, 1976, J. Heterocyclic Chem., 22, 1011, 1985 or J. Chem. Soc. Perkin Trans. 1, 1986, 877-884. To be more specific, the compound [14] is able to be produced by the following process.

Chemical Scheme 4

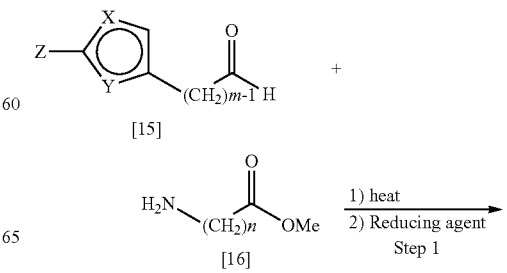

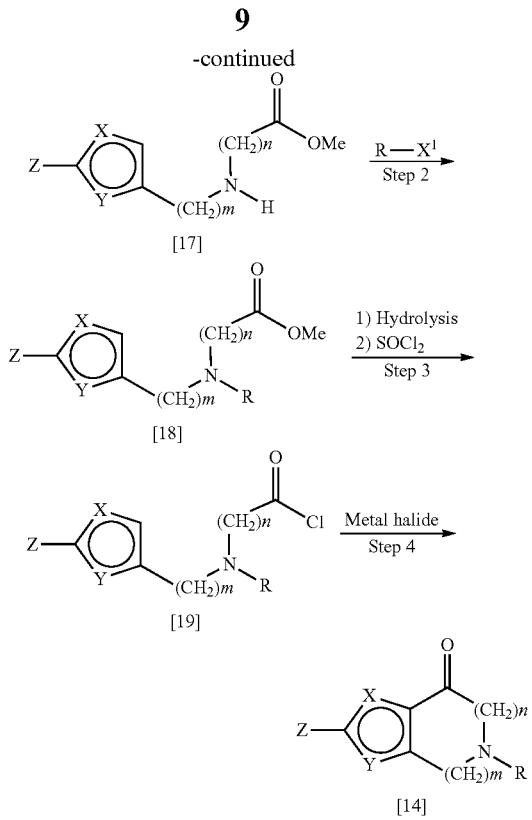

In the formulae, X, Y, Z, R, n and m have the same meanings as mentioned above. $X^1$ is halogen. Me is methyl.

Step 1

The compound [17] is able to be produced by reducing an imine prepared by a dehydrating condensation of the compound [16] with the compound [15]. Therefore, this reaction may be carried out by the methods which have been known per se as dehydrating reaction and reducing reaction.

This reaction may be usually carried out by such a manner that the compound

[15] is allowed to react with the compound [16] with accompanying dehydration under heating conditions in an appropriate solvent (such as a nonpolar solvent such as benzene and toluene) and the resulting imine is reduced by an appropriate reducing agent (such as lithium aluminum hydride, sodium borohydride, lithium borohydride, sodium cyanoborohydride and borane).

It is also possible to use a catalytic reduction reaction instead of a reducing agent. An example of the catalytic reduction method is that a catalyst such as platinum, Raney nickel, platinum-carbon (Pt—C), palladium-carbon (Pd—C) and a ruthenium complex is used to hydrogenate. As to the reaction temperature, the range of −78° C. to 200° C. is usually appropriate. The reaction time varies depending upon the type and the amount of the material used and upon the reaction temperature and, usually, the range of 30 minutes to 24 hours is appropriate.

Step 2

The compound [18] is produced by alkylation or carbonylation of the compound [17]. Therefore, this reaction is able to be conducted by a method which has been known per se as alkylation reaction or carbonylation reaction.

This step is usually carried out using the corresponding alkyl halide or carbonyl halide and acid anhydride, etc. in an appropriate solvent and in the presence of an appropriate base if necessary. Examples of the base which may be used therefor include any conventionally usable basic substance (such as pyridine and triethylamine), metal hydride (such as sodium hydride) and inorganic base (such as potassium carbonate, sodium hydrogen carbonate, sodium hydroxide and potassium hydroxide). The solvent usable therefor is not specifically limited so far as it does not participate in the reaction and examples thereof include ethers such as THF and 1,4-dioxane, amides such as DMF and N,N-dimethylacetamide, nitriles such as acetonitrile and propionitrile, hydrocarbons such as benzene and toluene, halogenated hydrocarbons such as chloroform and methylene chloride, sulfoxide such as DMSO, water, and a mixed solvent thereof. Reaction temperature within the range of −78° C. to 200° C. is usually appropriate. Reaction time varies depending upon the type and the amount of the material used and upon the reaction temperature and, usually, the range of 30 minutes to 24 hours is appropriate.

Step 3

The compound [19] is able to be produced in such a manner that the compound [18] is hydrolyzed and the resulting carboxylic acid is converted to an acid chloride. Therefore, this reaction is conducted by a method known per se as a hydrolysis reaction of ester followed by a conversion reaction into an acid chloride.

Production of a carboxylic acid by hydrolysis of ester is conducted under an acidic or alkaline condition. Examples of the acid which is able to be used for the hydrolysis include inorganic acids such as hydrochloric acid and sulfuric acid and those of the base usable therefor include inorganic bases such as sodium hydroxide and potassium hydroxide. The reaction solvent usable therefor is not specifically limited so far as it does not participate in the reaction and examples thereof include alcohols such as methanol and ethanol, ethers such as THF and 1,4-dioxane, water and a mixed solvent thereof. Reaction temperature within the range of 0° C. to 100° C. is appropriate and reaction time is usually within the range of several minutes to 24 hours.

Conversion of a carboxylic acid into an acid chloride is usually able to be conducted using thionyl chloride in an appropriate solvent if necessary. The reaction solvent usable therefor is not specifically limited so far as it does not participate in the reaction and examples thereof include ethers such as THF and 1,4-dioxane, amides such as DMF and N,N-dimethylacetamide, nitriles such as acetonitrile and propionitrile, hydrocarbons such as benzene and toluene, halogenated hydrocarbons such as chloroform and methylene chloride, sulfoxides such as DMSO, water and a mixed solvent thereof. Reaction temperature within the range of 0° C. to 100° C. is usually appropriate and the reaction time is usually within the range of several minutes to 24 hours.

Step 4

The compound [14] is able to be produced by an intramolecular cyclization reaction of a Friedel-Crafts type using the compound [19]. This reaction is able to be carried out using an appropriate metal halide or the like in an appropriate solvent if necessary. Examples of the usable metal halide include aluminum chloride, tin chloride, aluminum bromide and tin bromide. The reaction solvent usable therefor is not specifically limited so far as it does not participate in the reaction and examples thereof include ethers such as THF and 1,4-dioxane, amides such as DMF and N,N-dimethylacetamide, nitrites such as acetonitrile and propionitrile, hydrocarbons such as benzene, halogenated hydrocarbons such as chloroform and methylene chloride, sulfoxide such as DMSO, acetone, water and a mixed solvent thereof. Reaction temperature within the range of −78° C. to 200° C. is usually appropriate. Reaction time varies depending upon the type of the material used and upon the reaction temperature and, usually, it is appropriate to be within the range of 30 minutes to 24 hours.

Production Process 1-1-2: Production Process for the Material Compound [14] (Where m=2 and n=1)

The material compound [14] (m=2, n=1) is also able to be produced by the following method.

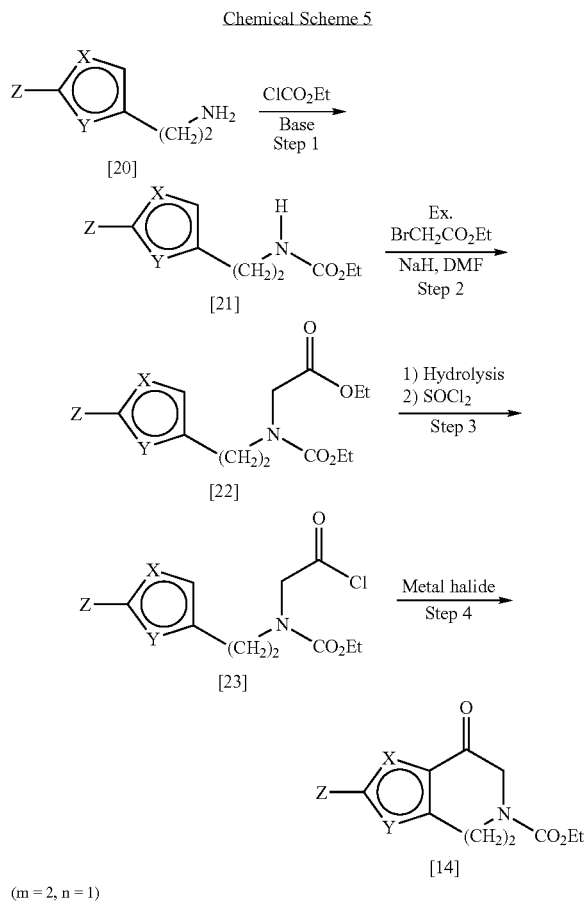

Chemical Scheme 5

(m = 2, n = 1)

In the formulae, X, Y, Z and Me have the same meanings as mentioned already. Et is ethyl.

Step 1

The compound [21] is able to be produced from the compound [20] by a carbonylation reaction using ethylchloroformate. Therefore, this reaction is able to be conducted by a method known per se as a carbonylation reaction.

This step is able to be usually carried out using the corresponding carbonyl halide, acid anhydride, etc. in the presence of an appropriate base if necessary in an appropriate solvent. Examples of the base usable therefor include the conventionally used any basic substance (such as pyridine and triethylamine), metal hydride (such as sodium hydride) and inorganic base (such as potassium carbonate, sodium hydrogen carbonate, sodium hydroxide and potassium hydroxide). The solvent usable therefor is not specifically limited so far as it does not participate in the reaction and examples thereof include ethers such as THF and 1,4-dioxane, amides such as DMF and N,N-dimethylacetamide, nitriles such as acetonitrile and propionitrile, hydrocarbons such as benzene and toluene, halogenated hydrocarbons such as chloroform and methylene chloride, sulfoxide such as DMSO, water and a mixed solvent thereof. Reaction temperature within the range of −78° C. to 200° C. is usually appropriate. Reaction time varies depending upon the type of the material used and upon the reaction temperature and, usually, it is appropriate to be within the range of 30 minutes to 24 hours.

Step 2

The compound [22] is able to be produced by alkylation of the compound [21]. Therefore, this reaction is able to be conducted by a known method per se as an alkylation reaction.

This step is usually carried out using the corresponding α-haloacetate in the presence of an appropriate base if necessary in an appropriate solvent. Examples of the base usable therefor include any conventionally used basic substance (such as pyridine and triethylamine), metal hydride (such as sodium hydride) and inorganic base (such as potassium carbonate, sodium hydrogen carbonate, sodium hydroxide and potassium hydroxide). The solvent usable therefor is not specifically limited so far as it does not participate in the reaction and examples thereof include ethers such as THF and 1,4-dioxane, amides such as DMF and N,N-dimethylacetamide, nitriles such as acetonitrile and propionitrile, hydrocarbons such as benzene and toluene, sulfoxide such as DMSO, water and a mixed solvent thereof. Reaction temperature within the range of −78° C. to 200° C. is usually appropriate. Reaction time varies depending upon the type of the material used and upon the reaction temperature and, usually, it is appropriate to be within the range of 30 minutes to 24 hours.

Step 3

The compound [23] is able to be produced in such a manner that an ester moiety of the compound [22] is hydrolyzed and the resulting carboxylic acid is converted into its acid chloride. Therefore, this reaction is conducted by a method known per se as a hydrolysis reaction of ester followed by a conversion reaction into an acid chloride.

Production of a carboxylic acid by hydrolysis of ester is able to be conducted under an acidic or alkaline condition. Examples of the acid which is able to be used for the hydrolysis include inorganic acid such as hydrochloric acid and sulfuric acid and those of the base usable therefor include inorganic base such as sodium hydroxide and potassium hydroxide. The reaction solvent usable therefor is not specifically limited so far as it does not participate in the reaction and examples thereof include alcohols such as methanol and ethanol, ethers such as THF and 1,4-dioxane, water and a mixed solvent thereof. Reaction temperature within the range of 0° C. to 100° C. is usually appropriate and reaction time is usually within the range of several minutes to 24 hours.

Conversion of a carboxylic acid into an acid chloride is usually able to be conducted using thionyl chloride in an appropriate solvent if necessary. The reaction solvent usable therefor is not specifically limited so far as it does not participate in the reaction and examples thereof include ethers such as THF and 1,4-dioxane, amides such as DMF and N,N-dimethylacetamide, nitriles such as acetonitrile and propionitrile, hydrocarbons such as benzene and toluene, sulfoxide such as DMSO, water and a mixed solvent thereof. Reaction temperature within the range of 0° C. to 100° C. is usually appropriate and reaction time is usually within the range of several minutes to 24 hours.

Step 4

The compound [14] is able to be produced by an intramolecular cyclization reaction of a Friedel-Crafts type using the compound [23].

This reaction is able to be carried out using an appropriate metal halide or the like in an appropriate solvent if necessary. Examples of the metal halide usable therefor include aluminum chloride, tin chloride, aluminum bromide and tin bromide. The reaction solvent usable therefor is not specifically limited so far as it does not participate in the reaction and examples thereof include ethers such as THF and 1,4-dioxane, amides such as DMF and N,N-dimethylacetamide, nitriles such as acetonitrile and propionitrile, hydrocarbons such as benzene, halogenated hydrocarbons such as chloroform and methylene chloride, sulfoxide such as DMSO, acetone, water and a mixed solvent thereof. Reaction temperature within the range of −78° C. to 200° C. is usually appropriate. Reaction time varies depending upon the type of the material used and upon the reaction temperature and, usually, it is appropriate to be within the range of 30 minutes to 24 hours.

Production Process 1-2: Production Process for the Material Compound [11]

The material compound [11] is also able to be produced, for example, by a method similar to that mentioned in Heterocycles, 12, 1479, 1979. To be more specific, the compound [11] is also able to be produced by the following method.

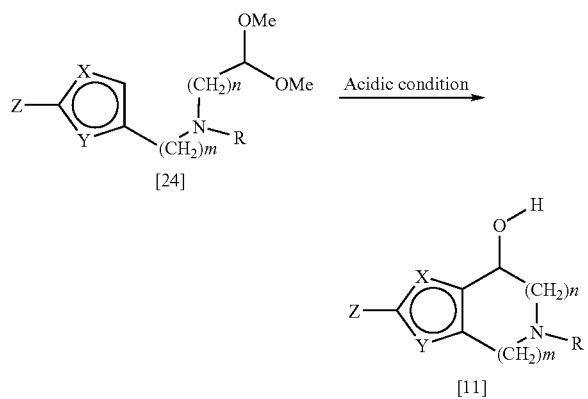

In the formulae, X, Y, Z, R, Ar, n, m and Me have the same meanings as mentioned above.

This reaction is an intramolecular cyclization reaction of the compound [24] and is able to be carried out by the methods known per se as a deprotection of acetal group under an acidic condition and a subsequent intramolecular reducing reaction.

This reaction proceeds under an appropriate acidic condition (for example, in an inorganic strong acid such as aqueous solution of hydrochloric acid, alcoholic hydrochloric acid, aqueous solution of sulfuric acid and alcoholic sulfuric acid).

Reaction time varies depending upon the type of material and acid, the reaction temperature, etc. and, usually, it is appropriately to be within the range of 30 minutes to 24 hours. The amount of acid to be used varies depending upon the type of material and acid, the reaction temperature, etc. and, usually, it is appropriate to be within the range of 0.01 to 3 times molar quantities relative to the compound [24].

Production Process 1-2-1: Production Process for the Material Compound [24]

The material compound [24] is also able to be produced, for example, by a method similar to that mentioned in Heterocycles, 12, 1479, 1979. To be more specific, the compound [24] is also able to be produced by the following method.

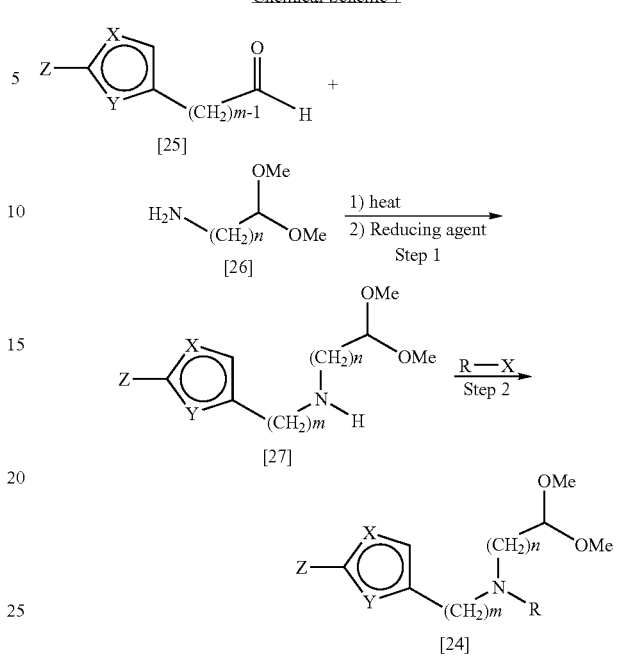

In the formulae, X, Y, Z, R, n, m and Me have the same meanings as mentioned already.

Step 1

The compound [27] is able to be produced by reducing an imine prepared by dehydrating condensation of the compound [25] with the compound [26]. Therefore, this reaction may be carried out by the methods which have been known per se as dehydrating reaction and reducing reaction.

This reaction may be usually carried out by such a manner that the compound [25] is allowed to react with the compound [26] accompanied by dehydration under a heating condition in an appropriate solvent (such as a nonpolar solvent such as benzene and toluene) and the resulting imine is reduced by an appropriate reducing agent (such as lithium aluminum hydride, sodium borohydride, lithium borohydride, sodium cyanoborohydride or borane) so as to convert to a secondary amine [27].

It is also possible to use a catalytic reduction reaction instead of a reducing agent. An example of the catalytic reduction method is that a catalyst such as platinum, Raney nickel, platinum-carbon (Pt—C), palladium-carbon (Pd—C) or a ruthenium complex is used to hydrogenate. As to the reaction temperature, the range of −78° C. to 200° C. is usually appropriate. The reaction time varies depending upon the type of the material used and upon the reaction temperature and, usually, the range of 30 minutes to 24 hours is appropriate.

Step 2

The compound [24] is produced by alkylation of the compound [27]. Therefore, this reaction is able to be conducted by a method which has been known per se as alkylation reaction or carbonylation reaction.

This step is usually carried out using the corresponding alkyl halide or carbonyl halide and acid anhydride, etc. in an appropriate solvent and in the presence of an appropriate base if necessary. Examples of the base which may be used therefor include any conventionally usable basic substance (such as pyridine and triethylamine), metal hydride (such as sodium hydride) and inorganic base (such as potassium carbonate, sodium hydrogen carbonate, sodium hydroxide and potassium hydroxide). The solvent usable therefor is not specifically limited so far as it does not participate in the reaction and examples thereof include ethers such as THF and 1,4-dioxane, amides such as DMF and N,N-dimethylacetamide, nitriles such as acetonitrile and propionitrile, hydrocarbons such as benzene and toluene, halogenated hydrocarbons such as chloroform and methylene chloride, sulfoxide such as DMSO, water and a mixed solvent thereof. Reaction temperature within the range of −78° C. to 200° C. is usually appropriate. Reaction time varies depending upon the type of the material used and upon the reaction temperature and, usually, the range of 30 minutes to 24 hours is appropriate.

Although it is possible to use the compound per se of the present invention as a drug, it is also possible to use after converting it into a form of a pharmaceutically acceptable salt by means of conventional methods. Examples of the salt as such include a salt with mineral acid such as hydrochloric acid, hydrobromic acid, sulfuric acid and phosphoric acid, and a salt with organic acid such as acetic acid, citric acid, tartaric acid, maleic acid, succinic acid, fumaric acid, p-toluenesulfonic acid, benzenesulfonic acid and methanesulfonic acid.

For example, a hydrochloride of the compound of the present invention is able to be produced by dissolving the compound of the present invention into a solution of hydrogen chloride in alcohol, ethyl acetate or diethyl ether.

In the compounds of the present invention, there are some compounds having asymmetric carbon and any one of the optical isomers and a mixture thereof is covered by the present invention. An optical isomer is able to be produced, for example, by means of optical resolution according to conventional methods using an optically active acid (such as tartaric acid, dibenzoyltartaric acid, mandelic acid and 10-camphorsulfonic acid) from the above-mentioned racemic compound utilizing its basic property or by means of the use of the optically active compound prepared beforehand as a material. Besides those, it is also possible to produce by means of an optical resolution using a chiral column or an asymmetric synthesis.

In some of the compounds of the present invention, there are cis-, trans-, Z- and E-compounds and each of those isomers and a mixture thereof are also covered by the present invention.

When the compound of the present invention or a pharmaceutically acceptable salt thereof is administered as a drug, the compound of the present invention or a pharmaceutically acceptable salt thereof is administered to mammals including humans either as it is or as a pharmaceutical composition containing the compound, for example, in 0.001% to 99.5% or, preferably, 0.1% to 90% thereof in a pharmaceutically acceptable non-toxic and inert carrier.

As to the carrier, one or more kind(s) of solid, semi-solid or liquid diluent(s), filler(s) and other auxiliary agent(s) for pharmaceutical prescriptions may be used. The pharmaceutical composition in accordance with the present invention is preferably administered in a dose unit form. The pharmaceutical composition is able to be administered interstitially, orally, intravenously, topically (such as percutaneously and by dropping into eye) or transrectally. It goes without saying that the administration is conducted by a dosage form suitable for the administering method as above.

The dose as a drug is preferably adjusted by taking into account the state of a patient such as age and body weight, type and degree of the disease and route of administration and, usually, amount of the compound of the present invention or a pharmaceutically acceptable salt thereof as the active ingredient to an adult per day in the case of oral administration is within the range of 0.1 mg to 5 g/adult or, preferably, within the range of 1 mg to 500 mg/adult. In some cases, not more than the above amount will be sufficient while, in some other cases, not less than the above amount may be necessary. Usually, it is administered once daily or by dividing into several times a day or it may be intravenously administered for a period of 1 to 24 hour(s) continuously.

EXAMPLES

The present invention will now be further illustrated by way of the following Reference Examples, Examples, Test Examples and Preparation Examples although the present invention is not limited thereto.

Reference Example 1

6-Methyl-4,5,6,7-tetrahydrofuro[2,3-c]pyridin-4-ol

Step 1

Ethyl Furfurylaminoacetate

Furfurylamine (15.0 g) and 17.2 g of triethylamine were dissolved in 75 mL of toluene, 20.8 g of ethyl chloroacetate was added thereto and the mixture was heated to reflux for 3 hours. After the reaction solution was cooled, 100 mL of water was added thereto and the mixture was subjected to extraction with ethyl acetate. The organic layer was washed with water and a saturated solution of sodium chloride and dried over anhydrous magnesium sulfate and the solvent was evaporated therefrom in vacuo. The residue was purified by silica gel column chromatography to give 18.2 g of an objective compound as yellow liquid.

Step 2

Ethyl furfuryl(ethoxycarbonyl)aminoacetate

Ethyl furfurylaminoacetate (18.2 g) prepared in the step 1 and 13.1 g of triethylamine were dissolved in 135 mL of methylene chloride, 11.9 g of ethyl chloroformate was gradually dropped thereinto under cooling with ice and the mixture was stirred at room temperature for 3 hours. Water (100 mL) was added to the reaction solution and the mixture was subjected to extraction with methylene chloride. The organic layer was washed with water and a saturated solution of sodium chloride successively and dried over anhydrous magnesium sulfate and the solvent was evaporated therefrom in vacuo. The residue was purified by silica gel column chromatography to give 24.0 g of an objective compound as slightly yellow liquid.

Step 3

Furfuryl(ethoxycarbonyl)aminoacetate

Ethyl furfuryl(ethoxycarbonyl)aminoacetate (19.1 g) prepared in the step 2 was dissolved in 100 mL of methanol, 6.3 g of potassium hydroxide was added thereto and the mixture was heated to reflux for 3 hours. The solvent of the reaction solution was evaporated in vacuo and the residue was dissolved in methylene chloride. The resulting solution was slowly neutralized with 1N aqueous solution of hydrochloric acid (ca. 150 mL) with stirring to adjust to pH 3. The organic layer was separated, washed with water and a saturated solution of sodium chloride successively and dried over anhydrous magnesium sulfate and the solvent was evaporated in vacuo to give 17.0 g of the objective compound.

Step 4

6-Ethoxycarbonyl-4,5,6,7-tetrahydrofuro[2,3-c]pyridin-4-one

Furfuryl(ethoxycarbonyl)aminoacetic acid (17.0 g) prepared in the step 3 was dissolved in 320 mL of methylene chloride, then 8.2 mL of thionyl chloride and 0.78 mL of DMF were added thereto and the mixture was heated to reflux for 3 hours. After the reaction solution was cooled and diluted with 600 mL of methylene chloride, 20.0 g of aluminum chloride was added thereto and the mixture was stirred at room temperature for 25 minutes. The reaction solution was poured over 500 mL of ice water, the organic layer was separated, washed with water and a saturated solution of sodium chloride successively and dried over anhydrous magnesium sulfate and the solvent was evaporated therefrom in vacuo. The residue was dissolved in ethyl acetate, washed with 5% aqueous ammonia and water successively and dried over anhydrous magnesium sulfate and the solvent was evaporated therefrom in vacuo. The residue was purified by silica gel column chromatography to give 9.61 g of the objective compound as slightly yellow powder.

Step 5

6-Methyl-4,5,6,7-tetrahydrofuro[2,3-c]pyridin-4-ol

A solution of 1.76 g of 6-ethoxycarbonyl-4,5,6,7-tetrahydrofuro[2,3-c]pyridin-4-one prepared in the step 4 in 20 mL of dry THF was slowly dropped into an ice-cooled solution of 0.45 g of lithium aluminum hydride in 20 mL of dry THF. The reaction solution was gradually heated followed by heating to reflux for 30 minutes. The reaction solution was cooled, an excess of lithium aluminum hydride was decomposed by a gradual addition of ice thereto and the mixture was subjected to extraction with ethyl acetate. The organic layer was washed with a saturated solution of sodium chloride and dried over anhydrous magnesium sulfate and the solvent was evaporated therefrom in vacuo. The residue was purified by silica gel column chromatography to give 1.03 g of the objective compound.
Slightly yellow powder, MS spectrum: 154[M+H]$^+$ Reference Example 2

2,6-Dimethyl-4,5,6,7-tetrahydrofuro[2,3-c]pyridin-4-ol

The same method as in Reference Example 1 was conducted using 5-methylfurfurylamine instead of furfurylamine to give the objective compound.
MS spectrum: 168[M+H]$^+$ Reference Example 3-1

5-Methyl-4,5,6,7-tetrahydrofuro[3,2-c]pyridin-7-ol

The same method as in Reference Example 1 was conducted using 3-furylmethylamine instead of furfurylamine to give the objective compound
MS spectrum: 154[M+H]$^+$.

Reference Example 3-2 (An Alternative Process)

5-Methyl-4,5,6,7-tetrahydrofuro[3,2-c]pyridin-7-ol

The same method as in Reference Example 6 was conducted using 4,5,6,7-tetrahydrofuro[3,2-c]pyridin-7-ol provided with Reference Example 33 instead of 4,5,6,7-tetrahydrothieno[2,3-c]pyridin-4-olto give the objective compound.
MS spectrum: 154[M+H]$^+$ Reference Example 4

4,5,6,7-Tetrahydrofuro[2,3-c]pyridin-4-ol

Step 1

N-(Trifluoromethanesulfonyl)furfurylamine

Furfurylamine (5.0 g) and 5.73 g of triethylamine were dissolved in 50 mL of methylene chloride and then 16.0 g of trifluoromethanesulfonic acid anhydride was slowly dropped thereinto with stirring and cooling with ice. The reaction solution was stirred at room temperature for 10 minutes and poured over 50 mL of water and the mixture was subjected to extraction with methylene chloride. The organic layer was washed with water and a saturated solution of sodium chloride successively and dried over anhydrous magnesium sulfate and the solvent was evaporated therefrom in vacuo to give 11.8 g of the objective compound as light yellow liquid.

Step 2 t-Butyl N-furfuryl-N-(trifluoromethanesulfonyl)aminoacetate

N-(Trifluoromethanesulfonyl)furfurylamine (11.8 g) prepared in the step 1 was dissolved in 30 mL of DMF, then 2.47 g of 60% sodium hydride was slowly added thereto with stirring under cooling with ice and the mixture was stirred at room temperature for 1 hour more. tert-Butyl bromoacetate (12.1 g) was slowly dropped into the above reaction solution under cooling with ice and the mixture was made back to room temperature and stirred for 2 hours.
The reaction solution was poured over 50 mL of water and the mixture was subjected to extraction with methylene chloride. The organic layer was washed with water and a saturated solution of sodium chloride successively and dried over anhydrous magnesium sulfate and the solvent was evaporated therefrom in vacuo. The residue was purified by silica gel column chromatography to give 10.9 g of the objective compound as light yellow liquid.

Step 3

N-Furfuryl-N-(trifluoromethanesulfonyl)aminoacetate tert-Butyl N-furfuryl-N-(trifluoromethanesulfonyl)-aminoacetate (10.9 g) prepared in the step 2 was dissolved in 60 mL of methylene chloride, 20 mL of trifluoroacetic acid was added thereto and the mixture was stirred overnight at room temperature. The solvent of the reaction solution was evaporated in vacuo and the residue was solidified by washing with n-hexane to give 8.69 g of the objective compound as light yellow powder.

Step 4

6-Trifluoromethanesulfonyl-4,5,6,7-tetrahydrofuro[2,3-c]pyridin-4(5H)one

N-Furfuryl-N-(trifluoromethanesulfonyl)aminoacetic acid (1.70 g) prepared in the step 3 was dissolved in 20 mL of methylene chloride, then 0.5 mL of thionyl chloride and one drop of DMF were added thereto and the mixture was heated to reflux for 1 hour. After the reaction solution was cooled, it was diluted by addition of 50 mL of methylene chloride, 1.5 g of aluminum chloride was added thereto and the mixture was stirred at room temperature for 30 minutes. The reaction solution was poured over 100 mL of ice water, the organic layer was separated, washed with water and a saturated solution of sodium chloride successively and dried over anhydrous magnesium sulfate and the solvent was evaporated therefrom in vacuo. The residue was dissolved in ethyl acetate, washed with a 5% aqueous ammonia and water successively and dried over anhydrous magnesium sulfate and the solvent was evaporated therefrom in vacuo. The residue was purified by silica gel column chromatography to give 1.10 g of the objective compound as slightly yellow liquid.

Step 5

4,5,6,7-Tetrahydrofuro[2,3-c]pyridin-4-ol

A solution of 1.10 g of 6-trifluoromethanesulfonyl-4,5,6,7-tetrahydrofuro[2,3-c]pyridin-4(5H)-one prepared in the step 4 in 10 ml of dry THF was slowly dropped into an ice-cooled solution of 0.31 g of lithium aluminum hydride in 10 ml of dry THF. The reaction solution was gradually heated followed by heating to reflux for 30 minutes. The reaction solution was cooled, an excess of lithium aluminum hydride was decomposed by a gradual addition of ice and the reaction solution was subjected to extraction with ethyl acetate. The organic layer was washed with a saturated solution of sodium chloride and dried over anhydrous magnesium sulfate and the solvent was evaporated therefrom in vacuo. The residue was purified by silica gel column chromatography to give 0.49 g of the objective compound.

Slightly yellow liquid, MS spectrum: 140[M+H]$^+$

Reference Example 5

4,5,6,7-Tetrahydrothieno[2,3-c]pyridin-4-ol

Step 1

2,2-Diethoxy-N-(thiophen-2-ylmethylene)ethanamine

2-Thiophene aldehyde (62.8 g) and 74.6 g of aminoacetaldehyde diethylacetal were dissolved in 200 mL of toluene and heated to reflux for 6 hours together with dehydration using a Dean-Stark trap. After confirming that a theoretical amount of water was separated, the solvent was evaporated therefrom in vacuo. The concentrated liquid was purified by a vacuum distillation to give 119 g of the objective compound.

Pale yellow liquid, Boiling point: 160° C./1 mmHg

Step 2

2,2-Diethoxy-N-(thiophen-2-ylmethyl)ethanamine 2,2-Diethoxy-N-(thiophen-2-ylmethylene)ethaneamine (100 g) prepared in the step 1 was dissolved in 500 mL of dry ethanol, then 18.3 g of sodium borohydride was slowly added thereto little by little at room temperature and the mixture was stirred overnight at room temperature. The solvent was evaporated from the reaction solution in vacuo and the residue was poured over 300 mL of a 10% aqueous solution of acetic acid. The resulting aqueous solution was washed with diethyl ether, neutralized with 10% aqueous ammonia and subjected to extraction with diethyl ether. The organic layer was washed with water and a saturated solution of sodium chloride successively and dried over anhydrous magnesium sulfate and the solvent was evaporated therefrom in vacuo to give 72.5 g of the objective compound as colorless liquid.

Step 3

4,5,6,7-Tetrahydrothieno[2,3-c]pyridin-4-ol 2,2-Diethoxy-N-(thiophen-2-ylmethyl)ethaneamine (72.5 g) prepared in the step 2 was dissolved in 5N aqueous solution of hydrochloric acid and stirred overnight at room temperature. The reaction solution was neutralized with 10% aqueous ammonia and subjected to extraction with ethyl acetate. The organic layer was separated, washed with water and a saturated solution of sodium chloride successively, dried over anhydrous magnesium sulfate and the solvent was evaporated therefrom in vacuo. The residue was purified by silica gel column chromatography to give 14.0 g of the objective compound.

Slightly yellow solid, MS spectrum: 156[M+H]$^+$

Reference Example 6

6-Methyl-4,5,6,7-tetrahydrothieno[2,3-c]pyridin-4-ol 4,5,6,7-Tetrahydrothieno[2,3-c]pyridin-4-ol (6.21 g) prepared in Reference Example 5 and 8.29 g of sodium carbonate were suspended in 50 mL of DMF, 6.25 g of methyl iodide was added thereto by dropping thereinto and the mixture was stirred at room temperature for 3 hours. The reaction solution was poured over 200 mL of water and subjected to extraction with ethyl acetate. The organic layer was washed with water and a saturated solution of sodium chloride successively and dried over anhydrous magnesium sulfate and the solvent was evaporated therefrom in vacuo to give 5.63 g of the objective compound.

Yellow solid, MS spectrum: 170[M+H]$^+$

Reference Example 7

6-Ethyl-4,5,6,7-tetrahydrothieno[2,3-c]pyridin-4-ol

The same method as in Reference Example 6 was conducted using methyl iodide instead of ethyl iodide to give the objective compound.

MS spectrum: 184[M+H]$^+$

Reference Example 8

2-Methyl-4,5,6,7-tetrahydrothieno[2,3-c]pyridin-4-ol

The same method as in Reference Example 5 (steps 1 to 3) was conducted using 5-methyl-2-thiophenaldehyde instead of 2-thiophenaldehyde to give the objective compound.

MS spectrum: 170[M+H]$^+$

Reference Example 9

2,6-Dimethyl-4,5,6,7-tetrahydrothieno[2,3-c]pyridin-4-ol

The same method as in Reference Example 6 was conducted using 2-methyl-4,5,6,7-tetrahydrothieno[2,3-c]pyridin-4-ol provided with Reference Example 8 instead of 4,5,6,7-tetrahydrothieno[2,3-c]pyridin-4-ol to give the objective compound.
MS spectrum: 184[M+H]$^+$

Reference Example 10

6-Ethyl-2-methyl-4,5,6,7-tetrahydrothieno[2,3-c]pyridin-4-ol

The same method as in Reference Example 6 was conducted using 2-methyl-4,5,6,7-tetrahydrothieno[2,3-c]pyridin-4-ol provided with Reference Example 8 instead of 4,5,6,7-tetrahydrothieno[2,3-c]pyridin-4-ol and was conducted using ethyl iodide instead of methyl iodide to give the objective compound.
MS spectrum: 198[M+H]$^+$

Reference Example 11

2-Chloro-6-methyl-4,5,6,7-tetrahydrothieno[2,3-c]pyridin-4-ol

Step 1

2-Chloro-4,5,6,7-tetrahydrothieno[2,3-c]pyridin-4-ol

The same method as in Reference Example 5 (steps 1 to 3) was conducted using 5-chloro-2-thiophenaldehyde instead of 2-thiophenaldehyde to give the objective compound.

Step 2

2-Chloro-6-methyl-4,5,6,7-tetrahydrothieno[2,3-c]pyridin-4-ol

The same method as in Reference Example 6 was conducted using 2-chloro-4,5,6,7-tetrahydrothieno[2,3-c]pyridin-4-ol provided with process 1 instead of 4,5,6,7-tetrahydrothieno[2,3-c]pyridin-4-ol to give the objective compound.
MS spectrum: 204[M+H]$^+$

Reference Example 12

2-Bromo-6-methyl-4,5,6,7-tetrahydrothieno[2,3-c]pyridin-4-ol

6-Methyl-4,5,6,7-tetrahydrothieno[2,3-c]pyridin-4-ol (1.2 g) prepared in Reference Example 6 was dissolved in 60 mL of acetic acid, a solution of 2.72 g of bromine in 10 mL of acetic acid was added thereto by dropping, then 0.1 mL of 33% solution of hydrogen bromide in acetic acid solution was added thereto and the mixture was stirred for 3 hours at room temperature. To the reaction solution was added 10 mL of 10% aqueous solution of sodium thiosulfate and then the reaction solution was concentrated in vacuo to evaporate acetic acid. The residue was made basic by addition of 25% aqueous ammonia with cooling followed by extracting with ethyl acetate. The organic layer was washed with water and a saturated solution of sodium chloride successively and dried over anhydrous magnesium sulfate and the solvent was evaporated therefrom in vacuo. The residue was purified by silica gel column chromatography to give 0.74 g of the objective compound.
Yellow powder, MS spectrum: 249[M+H]$^+$

Reference Example 13

4,5,6,7-Tetrahydrothieno[3,2-c]pyridin-7-ol

The same method as in Reference Example 5 (steps 1 to 3) was conducted using 3-thiophenaldehyde instead of 2-thiophenaldehyde to give the objective compound.
MS spectrum: 156[M+H]$^+$

Reference Example 14

5-Methyl-4,5,6,7-tetrahydrothieno[3,2-c]pyridin-7-ol

The same method as in Reference Example 6 was conducted using 4,5,6,7-tetrahydrothieno[3,2-c]pyridin-7-ol provided with Reference Example 13 instead of 4,5,6,7-tetrahydrothieno[2,3-c]pyridin-4-ol to give the objective compound.
MS spectrum: 170[M+H]$^+$

Reference Example 15

5-Cyclopropylmethyl-4,5,6,7-tetrahydrothieno[3,2-c]pyridin-7-ol

The same method as in Reference Example 6 was conducted using 4,5,6,7-tetrahydrothieno[3,2-c]pyridin-7-ol provided with Reference Example 13 instead of 4,5,6,7-tetrahydrothieno[2,3-c]pyridin-4-ol and was conducted using (bromomethyl)cyclopropane instead of methyl iodide to give the objective compound.
MS spectrum: 210[M+H]$^+$

Reference Example 16

5-Allyl-4,5,6,7-tetrahydrothieno[3,2-c]pyridin-7-ol

The same method as in Reference Example 6 was conducted using 4,5,6,7-tetrahydrothieno[3,2-c]pyridin-7-ol provided with Reference Example 13 instead of 4,5,6,7-tetrahydrothieno[2,3-c]pyridin-4-ol and was conducted using an allyl bromide instead of methyl iodide to give the objective compound.
MS spectrum: 196[M+H]$^+$

Reference Example 17

5-(2-Fluoroethyl)-4,5,6,7-tetrahydrothieno[3,2-c]pyridin-7-ol

The same method as in Reference Example 6 was conducted using 4,5,6,7-tetrahydrothieno[3,2-c]pyridin-7-ol provided with Reference Example 13 instead of 4,5,6,7-tetrahydrothieno[2,3-c]pyridin-4-ol and was conducted using 1-bromo-2-fluoroethane instead of methyl iodide to give the objective compound.
MS spectrum: 202[M+H]$^+$

Reference Example 18

2-Bromo-5-methyl-4,5,6,7-tetrahydrothieno[3,2-c]pyridin-7-ol

The same method as in Reference Example 12 was conducted using 5-methyl-4,5,6,7-tetrahydrothieno[3,2-c]pyridin-7-ol provided with Reference Example 14 instead of 6-methyl-4,5,6,7-tetrahydrothieno[2,3-c]pyridin-4-ol to give the objective compound.
MS spectrum: 248[M+H]$^+$

Reference Example 19

7-Methyl-5,6,7,8-tetrahydro-4H-furo[2,3-c]azepin-4-ol

Step 1

Ethyl 3-[(furan-2-ylmethylene)amino]propanoate

2-Furaldehyde (10 g) was dissolved in 170 mL of methylene chloride, then 10 g of magnesium sulfate, 16 mL of triethylamine and 16 g of ethyl 3-aminopropionate hydrochloride were successively added thereto and the mixture was stirred overnight at room temperature. The reaction solution was poured over 100 mL of water, the mixture was subjected to extraction with methylene chloride and the solvent was evaporated therefrom in vacuo. The residue was dissolved in 100 mL of ethyl acetate, washed with water and a saturated solution of sodium chloride successively and dried over anhydrous magnesium sulfate and the solvent was evaporated therefrom in vacuo to give 19.2 g of the objective compound as yellow liquid.

Step 2

Ethyl 3-[(furan-2-ylmethyl)amino]propanoate

Ethyl 3-[(furan-2-ylmethylene)amino]propionate (19.2 g) prepared in the step 1 was dissolved in 200 mL of dry ethanol, 4.46 g of sodium borohydride was slowly added thereto little by little at room temperature and the mixture was stirred overnight at room temperature. The solvent was evaporated in vacuo from the reaction and the residue was poured over 300 mL of 10% aqueous solution of acetic acid. The resulting aqueous solution was washed with diethyl ether, neutralized with 10% aqueous ammonia and subjected to extraction with diethyl ether. The organic layer was washed with water and a saturated solution of sodium chloride successively and dried over anhydrous magnesium sulfate and the solvent was evaporated in vacuo therefrom to give 10.8 g of the objective compound as yellow liquid.

Step 3

Ethyl 3-[(furan-2-ylmethyl)(ethoxycarbonyl)amino]propanoate

Ethyl 3-[(furan-2-ylmethyl)amino]propionate (10.8 g) prepared in the step 2 and 18.3 mL of triethylamine were dissolved in 180 mL of methylene chloride, 7.14 g of ethyl chloroformate was added by slowly dropping thereinto under cooling with ice and the mixture was stirred at room temperature for 5 hours. Water (200 mL) was added to the reaction solution and the mixture was subjected to extraction with methylene chloride. The organic layer was washed with water and a saturated solution of sodium chloride successively and dried over anhydrous magnesium sulfate and the solvent was evaporated in vacuo therefrom. The residue was purified by silica gel column chromatography to give 13.77 g of the objective compound as yellow liquid.

Step 4

3-[(Furan-2-ylmethyl)(ethoxycarbonyl)amino]propanoic acid

Ethyl 3-[(furan-2-ylmethyl) (ethoxycarbonyl)amino]-propionate (13.77 g) prepared in the step 3 was dissolved in 200 mL of methanol, 5.0 g of potassium hydroxide was added thereto and the mixture was heated to reflux for 3 hours. The solvent of the reaction solution was evaporated in vacuo and the residue was dissolved in methylene chloride. The resulting solution was slowly neutralized to pH 3 using 1N aqueous solution of hydrochloric acid (about 80 mL) with stirring. The organic layer was separated, washed with water and a saturated solution of sodium chloride successively and dried over anhydrous magnesium sulfate and the solvent was evaporated in vacuo therefrom to give 12.56 g of the objective compound as yellow liquid.

Step 5

7-Ethoxycarbonyl-5,6,7,8-tetrahydrofuro[2,3-c]azepin-4-one

3-[(Furan-2-ylmethyl)(ethoxycarbonyl)amino]propionic acid (3.6 g) prepared in the step 4 was dissolved in 300 mL of methylene chloride, then 2.66 g of thionyl chloride and 5 drops of DMF were added thereto and the mixture was heated to reflux for 3 hours. The reaction solution was cooled, 20.0 g of aluminum chloride was added thereto and the mixture was heated to reflux again for 30 minutes. The reaction solution was poured over 300 mL of ice water, the organic layer was separated, washed with water and a saturated solution of sodium chloride successively and dried over anhydrous magnesium sulfate and the solvent was evaporated in vacuo therefrom. The residue was purified by silica gel column chromatography to give 1.38 g of the objective compound as yellow liquid.

Step 6

7-Methyl-5,6,7,8-tetrahydro-4H-furo[2,3-c]azepin-4-ol

A solution of 1.38 g of 7-ethoxycarbonyl-5,6,7,8-tetrahydrofuro[2,3-c]azepin-4-one prepared in the step 5 in 30 mL of dry THF was slowly added by dropping into an ice-cooled solution of 0.29 g of lithium aluminum hydride in 20 mL of dry THF. The reaction solution was gradually heated followed by heating to reflux for 30 minutes. The reaction solution was cooled, an excess of lithium aluminum hydride was decomposed by gradual addition of ice thereto and the reaction solution was subjected to extraction with ethyl acetate. The organic layer was washed with a saturated solution of sodium chloride and dried over anhydrous magnesium sulfate and the solvent was evaporated therefrom in vacuo. The residue was purified by silica gel column chromatography to give 0.45 g of the objective compound.
Yellow liquid, MS spectrum: 168[M+H]$^+$

Reference Example 20

2,7-Dimethyl-5,6,7,8-tetrahydro-4H-furo[2,3-c]azepin-4-ol

The same method as in Reference Examples 19 was conducted using 5-methyl-2-furaldehyde instead of 2-furaldehyde to give the objective compound.

MS spectrum: 182[M+H]$^+$

Reference Example 21

5-Methyl-5,6,7,8-tetrahydro-4H-furo[3,2-c]azepin-8-ol

The same method as in Reference Example 19 was conducted using 3-furaldehyde instead of 2-furaldehyde to give the objective compound.

MS spectrum: 168[M+H]$^+$

Reference Example 22

7-Methyl-5,6,7,8-tetrahydro-4H-thieno[2,3-c]azepin-4-ol

The same method as in Reference Example 19 was conducted using 2-thiophenaldehyde instead of 2-furaldehyde to give the objective compound.

MS spectrum: 184[M+H])

Reference Example 23

2,7-Dimethyl-5,6,7,8-tetrahydro-4H-thieno[2,3-c]azepin-4-ol

The same method as in Reference Example 19 was conducted using 5-methyl-2-thiophenaldehyde instead of 2-furaldehyde to give the objective compound.

MS spectrum: 198[M+H]$^+$

Reference Example 24

2-Chloro-7-methyl-5,6,7,8-tetrahydro-4H-thieno[2,3-c]azepin-4-ol

The same method as in Reference Example 19 was conducted using 5-chloro-2-thiophenaldehyde instead of 2-furaldehyde to give the objective compound.

MS spectrum: 218[M+H]$^+$

Reference Example 25

5-Methyl-5,6,7,8-tetrahydro-4H-thieno[3,2-c]azepin-8-ol

The same method as in Reference Example 19 was conducted using 3-thiophenaldehyde instead of 2-furaldehyde to give the objective compound.

MS spectrum: 184[M+H]$^+$

Reference Example 26

2,6-Dimethyl-5,6,7,8-tetrahydro-4H-furo[2,3-d]azepin-4-ol

Step 1

2-Methyl-5-(2-nitrovinyl) furan

5-Methyl-2-furaldehyde (2.75 g) was gradually added by dropping, with stirring under ice cooling, to a solution prepared by dropping 3.05 g of nitromethane into 50 mL of an ice-cooled 20% aqueous solution of sodium hydroxide. After completion of the addition, the mixture was vigorously stirred for 10 minutes more to finish the reaction and the reaction solution was slowly poured over 60 mL of an ice-cooled 6N hydrochloric acid. The mixed solution was stirred for 10 minutes and the resulting separated crystals were filtered, washed with water and dried to give 2.20 g of the objective compound as yellow powder.

Step 2

2-(5-Methylfuran-2-yl)ethylamine

A solution of 2.0 g of 2-methyl-5-(2-nitrovinyl)furan prepared in the step 1 in 50 mL of dry THF was slowly dropped into a solution of 1.0 g of ice-cooled lithium aluminum hydride in 50 mL of dry THF. The reaction solution was gradually heated followed by heating to reflux for 4 hours. The reaction solution was cooled, ice was gradually added thereto to decompose an excess of lithium aluminum hydride and the reaction solution was subjected to extraction with ethyl acetate. The organic layer was washed with a saturated solution of sodium chloride and dried over anhydrous magnesium sulfate and the solvent was evaporated therefrom in vacuo to give 1.75 g of the objective compound as yellow liquid.

Step 3

Ethyl[2-(5-methylfuran-2-yl)ethyl]carbamate 2-(5-Methylfuran-2-yl)ethylamine (1.0 g) prepared in the step 2 and 2.2 mL of triethylamine were dissolved in 25 mL of methylene chloride, 0.87 g of ethyl chloroformate was slowly dropped thereinto under cooling with ice and the mixture was stirred at room temperature for 8 hours. To the reaction solution was added 200 mL of water followed by extracting with methylene chloride. The organic layer was washed with water and a saturated solution of sodium chloride successively and dried over anhydrous magnesium sulfate and the solvent was evaporated therefrom in vacuo. The residue was purified by silica gel column chromatography to give 0.61 g of the objective compound as yellow liquid.

Step 4

Ethyl{ethoxycarbonyl[2-(5-methylfuran-2-yl)ethyl]amino}acetate

Ethyl[2-(5-methylfuran-2-yl)ethyl]carbamate (0.60 g) prepared in the step 3 was dissolved in 6 mL of DMF, 0.15 g of 60% sodium hydride was slowly added thereto with stirring and ice-cooling and the mixture was stirred at room temperature for 1 hour more. Ethyl bromoacetate (0.40 g) was slowly dropped into the reaction solution under cooling with ice and the mixture was made back to room temperature followed by stirring overnight. The reaction solution was poured over 20 mL of water followed by extracting with diethyl ether. The organic layer was washed with water and a saturated solution of sodium chloride successively and dried over anhydrous magnesium sulfate and the solvent was evaporated therefrom in vacuo. The residue was purified by silica gel column chromatography to give 0.65 g of the objective compound as pale yellow liquid.

Step 5

{Ethoxycarbonyl[2-(5-methylfuran-2-yl)ethyl]amino}acetic acid

Ethyl{ethoxycarbonyl[2-(5-methylfuran-2-yl)ethyl]-amino}acetate (0.65 g) prepared in the step 4 was dissolved in 5 mL of ethanol, 0.30 g of potassium hydroxide was added thereto and the mixture was heated to reflux for 3 hours. The solvent of the reaction solution was evaporated in vacuo and the residue was dissolved in ethyl acetate. The resulting solution was slowly neutralized with 1N aqueous solution of hydrochloric acid (ca. 80 mL) with stirring to adjust to pH 3. The organic layer was separated, washed with water and a saturated solution of sodium chloride successively and dried over anhydrous magnesium sulfate and the solvent was evaporated therefrom in vacuo. The residue was purified by silica gel column chromatography to give 0.18 g of the objective compound as yellow liquid.

Step 6

6-Ethoxycarbonyl-2-methyl-5,6,7,8-tetrahydrofuro[2,3-d]azepin-4-one

[Ethoxycarbonyl[2-(5-methylfuran-2-yl)ethyl]amino]-acetic acid (0.17 g) prepared in the step 5 was dissolved in 3.5 mL of methylene chloride, then 0.12 g of thionyl chloride and 1 drop of DMF were added thereto and the mixture was heated to reflux for 2 hours. After the reaction solution was cooled, it was diluted with 5 mL of methylene chloride, then 0.18 g of aluminum chloride was added thereto and the mixture was heated to reflux again for 30 minutes. After the reaction solution was cooled, it was poured over 50 mL of ice water, the organic layer was separated, washed with water and a saturated solution of sodium chloride successively and dried over anhydrous magnesium sulfate and the solvent was evaporated therefrom in vacuo. The residue was purified by silica gel column chromatography to give 0.07 g of the objective compound as yellow liquid.

Step 7

2,6-Dimethyl-5,6,7,8-tetrahydro-4H-furo[2,3-d]azepin-4-ol

A solution of 6-ethoxycarbonyl-2-methyl-4,5,7,8-tetrahydrofuro[2,3-d]azepin-4-one (27 mg) prepared in the step 6 in 1 mL of dry THF was slowly dropped into an ice-cooled solution of 6.4 mg of lithium aluminum hydride in 1 mL of dry THF. The reaction solution was gradually heated followed by heating to reflux for 2 hours. Then the reaction solution was cooled, ice was gradually added thereto so that an excess amount of lithium aluminum hydride was decomposed and the mixture was subjected to extraction with ethyl acetate. The organic layer was washed with a saturated solution of sodium chloride and dried over anhydrous magnesium sulfate and the solvent was evaporated therefrom in vacuo. The residue was purified by silica gel column chromatography to give 17 mg of the objective compound.

Yellow liquid, MS spectrum: 182[M+H]$^+$

Reference Example 27

6-Methyl-5,6,7,8-tetrahydro-4H-furo[2,3-d]azepin-4-ol

The same method as in Reference Example 26 was conducted using 2-furaldehyde instead of 5-methyl-2-thiophenaldehyde to give the objective compound.

MS spectrum: 168[M+H]$^+$

Reference Example 28

6-Methyl-5,6,7,8-tetrahydro-4H-thieno[2,3-d]azepin-4-ol

The same method as in Reference Example 26 was conducted using 2-thiophenaldehyde instead of 5-methyl-2-furaldehyde to give the objective compound.

MS spectrum: 184[M+H]$^+$

Reference Example 29

5,6,7,8-tetrahydro-4H-thieno[2,3-d]azepin-4-ol

Step 1

N-[2-(Thieno-2-yl)ethyl]trifluoromethanesulfonamide 2-(Thieno-2-yl)ethylamine (5.0 g) and 4.38 g of triethylamine were dissolved in 100 mL of methylene chloride and 12.2 g of trifluoromethanesulfonic acid anhydride was slowly dropped thereinto with stirring under ice-cooling. The reaction solution was stirred at room temperature for 10 minutes and poured over 200 mL of water and the mixture was subjected to extraction with methylene chloride. The organic layer was washed with water and a saturated solution of sodium chloride successively and dried over anhydrous magnesium sulfate and the solvent was evaporated therefrom in vacuo to give 10.2 g of the objective compound as yellow liquid.

Step 2

Ethyl{trifluoromethanesulfonyl-[2-(thieno-2-yl)ethyl]amino}acetate

N-[2-(Thieno-2-yl)ethyl]trifluoromethane sulfonamide (10.2 g) prepared in the step 1 was dissolved in 30 mL of DMF, 1.73 g of 60% sodium hydride was slowly added thereto under ice-cooling with stirring and the mixture was stirred at room temperature for 1 hour more. Into the reaction solution was slowly dropped 7.23 g of ethyl bromoacetate under ice-cooling and the mixture was made back to room temperature and stirred overnight.

The reaction solution was poured over 100 mL of water followed by extracting with methylene chloride. The organic layer was washed with water and a saturated solution of sodium chloride successively and dried over anhydrous magnesium sulfate and the solvent was evaporated therefrom in vacuo. The residue was purified by silica gel column chromatography to give 12.5 g of the objective compound as colorless liquid.

Step 3

{Trifluoromethanesulfonyl[2-(thieno-2-yl)ethyl]amino}acetic acid

Ethyl{trifluoromethanesulfonyl-[2-(thieno-2-yl)-ethyl]amino}acetate (12.3 g) prepared in the step 2 was dissolved in 100 mL of ethanol, then 0.71 g of water and 1.57 g of sodium hydroxide were added thereto and the mixture was stirred overnight at room temperature. The solvent of the reaction solution was evaporated in vacuo and the residue was dissolved in ethyl acetate. The resulting solution was slowly neutralized with 1N aqueous solution of hydrochloric acid (ca. 50 mL) with stirring to adjust to pH 3. The organic layer was separated, washed with water and a saturated solution of sodium chloride successively and dried over anhydrous magnesium sulfate and the solvent was evaporated therefrom in vacuo. The residue was purified by silica gel column chromatography to give 10.6 g of the objective compound as yellow liquid.

Step 4

6-Trifluoromethanesulfonyl-4,5,7,8-tetrahydro-thieno[2,3-d]azepin-4-one

{Trifluoromethanesulfonyl-[2-(thieno-2-yl)ethyl]-amino}acetic acid (10.5 g) prepared in the step 3 and 0.7 mL of DMF were dissolved in 120 mL of thionyl chloride and the mixture was heated to reflux for 3 hours. Thionyl chloride was evaporated from the reaction solution in vacuo, the residue was diluted with 200 mL of methylene chloride, 8.8 g of aluminum chloride was added thereto and the mixture 4 was stirred at room temperature for 3 hours. The reaction solution was poured over 300 mL of ice water, the organic layer was separated, washed with water and a saturated solution of sodium chloride successively and dried over anhydrous magnesium sulfate and the solvent was evaporated therefrom in vacuo. The residue was purified by silica gel column chromatography to give 7.0 g of the objective compound.

Step 5

5,6,7,8-Tetrahydro-4H-thieno[2,3-d]azepin-4-ol

A solution of 2.5 g of 6-trifluoromethanesulfonyl-4,5,7,8-tetrahydro-thieno[2,3-d]azepin-4-one prepared in the step 4 in 30 mL of dry THF was slowly dropped into an ice-cooled solution of 0.63 g of lithium aluminum hydride in 20 mL of dry THF. The reaction solution was gradually heated followed by heating to reflux overnight. Then the reaction solution was cooled, ice was gradually added thereto so that an excess of lithium aluminum hydride was decomposed and the mixture was subjected to extraction with ethyl acetate. The organic layer was washed with a saturated solution of sodium chloride and dried over anhydrous magnesium sulfate and the solvent was evaporated therefrom in vacuo. The residue was purified by silica gel column chromatography to give 0.69 g of the objective compound.
MS spectrum: 170[M+H]$^+$ Reference Example 30

2-Methyl-4,5,6,7-tetrahydrothieno[3,2-c]pyridin-7-ol

The same method as in Reference Example 5 (steps 1 to 3) was conducted using 5-methyl-3-thiophenaldehyde instead of 2-thiophenaldehyde to give the objective compound.
MS spectrum: 170[M+H]$^+$ Reference Example 31

2,5-Dimethyl-4,5,6,7-tetrahydrothieno[3,2-c]pyridin-7-ol

The same method as in Reference Example 6 was conducted using 2-methyl-4,5,6,7-tetrahydrothieno[3,2-c]pyridin-7-ol provided with Reference Example 30 instead of 4,5,6,7-tetrahydrothieno[2,3-c]pyridin-4-ol to give the objective compound.
MS spectrum: 184[M+H]$^+$ Reference Example 32

5-Ethyl-2-methyl-4,5,6,7-tetrahydrothieno[3,2-c]pyridin-7-ol

The same method as in Reference Example 6 was conducted using 4,5,6,7-tetrahydrothieno[2,3-c]pyridin-7-ol provided with Reference Example 30 instead of 4,5,6,7-tetrahydrothieno[2,3-c]pyridin-4-ol and was conducted using ethyl iodide instead of methyl iodide to give the objective compound.
MS spectrum: 198[M+H]$^+$ Reference Example 33

4,5,6,7-Tetrahydrofuro[3,2-c]pyridin-7-ol

The same method as in Reference Example 5 (steps 1 to 3) was conducted using 2-thiophenaldehyde instead of 3-furaldehyde to give the objective compound.
MS spectrum: 140[M+H])

Reference Example 34

5-Ethyl-4,5,6,7-tetrahydrofuro[3,2-c]pyridin-7-ol

The same method as in Reference Example 6 was conducted using 4,5,6,7-tetrahydrofuro[3,2-c]pyridin-7-ol provided with Reference Example 33 instead of 4,5,6,7-tetrahydrothieno[2,3-c]pyridin-4-ol and was conducted using ethyl iodide instead of methyl iodide to give the objective compound.
MS spectrum: 168[M+H])

Reference Example 35

5,6,7,8-Tetrahydro-4H-thieno[2,3-c]azepin-4-ol

Step 1

Ethyl 3-[(thiophen-2-ylmethyl)amino]propanoate

2-Thiophene aldehyde (11.2 g) was dissolved in 100 mL of methanol, then 12.1 g of triethylamine and 16.1 g of ethyl 3-aminopropionate hydrochloride were added thereto in this order and the mixture was stirred overnight at room temperature. The reaction solution was cooled down to 0° C., 2.27 g of sodium borohydride was slowly added thereto little by little and the mixture was stirred at room temperature for 1 hour.

The solvent was evaporated from the reaction solution in vacuo and the residue was poured over 300 mL of 10% aqueous solution of acetic acid. The resulting aqueous solution was washed with diethyl ether, neutralized with 10% aqueous ammonia and subjected to extraction with diethyl-ether. The organic layer was washed with water and a saturated solution of sodium chloride successively and dried over anhydrous magnesium sulfate and the solvent was evaporated therefrom in vacuo to give 15.5 g of the objective compound as yellow liquid.

Step 2

Ethyl 3-[(thiophen-2-ylmethyl)(formyl)amino]propanoate

Ethyl 3-[(thiophen-2-ylmethyl)amino]propionate (13.8 g) prepared in the step 1 and 47.8 g of ethyl formate were dissolved in 100 mL of toluene and heated to reflux overnight. After the reaction solution was cooled, the solvent was evaporated therefrom in vacuo to give 15.6 g of the objective compound as light yellow liquid.

Step 3

3-[(Thiophen-2-ylmethyl)(formyl)amino]propanoic acid

Ethyl 3-[(thiophen-2-ylmethyl) (formyl)amino]-propionate (15.6 g) prepared in the step 2 was added to a solution of 5.4 g of potassium hydroxide in 100 mL of ethanol and stirred at room temperature for 2 hours. The solvent was evaporated from the reaction solution in vacuo, 50 mL of water was added to the residue and the mixture was subjected to extraction with diethyl ether. The resulting aqueous solution was slowly neutralized with a 1N aqueous solution of hydrochloric acid with stirring to adjust to pH 3 followed by extracting with diethyl ether. The organic layer was separated, washed with water and a saturated solution of sodium chloride successively and dried over anhydrous magnesium sulfate and the solvent was evaporated therefrom in vacuo to give 13.8 g of the objective compound as light yellow liquid.

Step 4

7-Formyl-5,6,7,8-tetrahydrothieno[2,3-c]azepin-4-one

3-[(Thiophen-2-ylmethyl) (formyl)amino]-propionic acid (13.8 g) prepared in the step 3 was dissolved in 25 mL of nitrobenzene, then 9.2 g of thionyl chloride and 0.01 mL of DMF were added thereto and the mixture was heated with stirring at 70° C. for 2 hours.

A solution of 22.6 g of zirconium chloride in 80 mL of nitrobenzene was heated at 70° C. and the above reaction solution was slowly dropped thereinto followed by heating for 1 hour with stirring.

After the reaction solution was cooled, it was poured over 200 mL of ice water, 10 g of active charcoal was added thereto and the mixture was stirred for 10 minutes. The mixture was filtered through Celite to remove insoluble matters and the filtrate was subjected to extraction with diethyl ether (2×200 mL). The organic layer was separated, washed with water and a saturated solution of sodium chloride successively and diethyl ether was evaporated therefrom in vacuo to give a solution containing nitrobenzene. The residue was purified by silica gel column chromatography to give 9.2 g of the objective compound as light yellow liquid.

Step 5

5,6,7,8-Tetrahydrothieno[2,3-c]azepin-4-one

7-Formyl-5,6,7,8-tetrahydrothieno[2,3-c]azepin-4-one (2.6 g) prepared in the step 4 was dissolved in 4N hydrochloric acid/dioxane solution, 13.5 mL of water was added thereto and the mixture was heated at 60° C. for 6 hours with stirring. The solvent was evaporated from the reaction solution in vacuo, water was added to the residue and the mixture was subjected to extraction with diethyl ether. The resulting aqueous solution was slowly neutralized with an aqueous solution of sodium hydrogen carbonate with stirring and subjected to extraction with diethyl ether. The organic layer was separated, washed with water and a saturated solution of sodium chloride successively and dried over anhydrous magnesium sulfate and the solvent was evaporated therefrom in vacuo to give 2.1 g of the objective compound as a brown solid.

Step 6

5,6,7,8-Tetrahydro-4H-thieno[2,3-c]azepin-4-ol

A solution of 2.1 g of 5,6,7,8-tetrahydrothieno-[2,3-c] azepin-4-one prepared in the step 5 in 20 mL of methanol was cooled with ice, 0.28 g of sodium borohydride was slowly added thereto and the mixture was stirred for 3 hours at room temperature. The reaction solution was slowly added to ice water so that an excess of sodium borohydride was decomposed and, after that, the reaction solution was subjected to extraction with diethyl ether. The organic layer was washed with a saturated solution of sodium chloride and dried over anhydrous magnesium sulfate and the solvent was evaporated therefrom in vacuo to give 1.37 g of the objective compound.

Pale yellow powder, MS spectrum: 170[M+H]$^+$

Reference Example 36

2,5-Dimethyl-5,6,7,8-tetrahydro-4H-thieno[3,2-c]azepin-8-ol

The same method as in Reference Example 19 was conducted using 5-methyl-3-thiophenaldehyde instead of 2-furaldehyde to give the objective compound.

MS spectrum: 198[M+H]$^+$

Reference Example 37

5,6,7,8-Tetrahydro-4H-furo[2,3-c]azepin-4-ol

The same method as in Reference Example 35 was conducted using 2-furaldehyde instead of 2-thiophenaldehyde to give the objective compound.

MS spectrum: 154[M+H]$^+$

Reference Example 38

7-(2,2,2-Trifluoro-1-ethyl)-5,6,7,8-tetrahydro-4H-furo[2,3-c]azepin-4-ol

Step 1

7-Trifluoroacetyl-5,6,7,8-tetrahydro-4H-furo[2,3-c]azepin-4-ol 5,6,7,8-Tetrahydro-4H-furo[2,3-c]azepin-4-ol (28 mg) prepared in Reference Example 37 and 57 mg of triethylamine were dissolved in 1 mL of methylene chloride, 57 mg of trifluoroacetic acid anhydride was dropped thereinto and the mixture was stirred at room temperature for 3 hours. The reaction solution was poured over 1 mL of water followed by extracting with ethyl acetate. The organic layer was washed with water and a saturated solution of sodium chloride successively and dried over anhydrous magnesium sulfate and the solvent was evaporated therefrom in vacuo to give 37 mg of the objective compound.

Step 2

7-(2,2,2-Trifluoro-1-ethyl)-5,6,7,8-tetrahydro-4H-furo[2,3-c]azepin-4-ol

7-Trifluoroacetyl-5,6,7,8-tetrahydro-4H-furo[2,3-c]-azepin-4-ol prepared in the step 1 was dissolved in 1 mL of THF, a three molar equivalent of a solution of borane in THF was dropped thereinto under ice-cooling with stirring and the mixture was stirred at room temperature for 2 hours. The reaction solution was poured over 1 mL of water followed by extracting with ethyl acetate. The organic layer was washed with water and a saturated solution of sodium chloride successively and dried over anhydrous magnesium sulfate and the solvent was evaporated therefrom in vacuo. The resulting residue was purified by silica gel column chromatography to give 23 mg of the objective compound.
MS spectrum: 236[M+H]$^+$

Reference Example 39

7-Cyclopropylmethyl-5,6,7,8-tetrahydro-4H-furo[2,3-c]azepin-4-ol

The same method as in Reference Example 38 (steps 1 to 2) was conducted using cyclopropane carbonyl chloride instead of trifluoroacetic anhydride to give the objective compound.
MS spectrum: 208[M+H]$^+$

Reference Example 40

7-(2-Methoxy-1-ethyl)-5,6,7,8-tetrahydro-4H-furo[2,3-c]azepin-4-ol

The same method as in Reference Example 6 was conducted using 4,5,6,7-tetrahydro-4H-furo[2,3-c]azepin-4-ol provided with Reference Example 37 instead of 4,5,6,7-tetrahydrothieno[2,3-c]pyridin-4-ol and was conducted using 2-bromoethyl methyl ether instead of methyl iodide to give the objective compound.
MS spectrum: 212[M+H]$^+$

Reference Example 41

7-Cyanomethyl-5,6,7,8-tetrahydro-4H-furo[2,3-c]azepin-4-ol

The same method as in Reference Example 6 was conducted using 5,6,7,8-tetrahydro-4H-furo[2,3-c]azepin-4-ol provided with Reference Example 37 instead of 4,5,6,7-tetrahydrothieno[2,3-c]pyridin-4-ol and was conducted using bromoacetonitrile instead of methyl iodide to give the objective compound.
MS spectrum: 193[M+H]$^+$

Reference Example 42

7-Ethoxycarbonylmethyl-5,6,7,8-tetrahydro-4H-furo[2,3-c]azepin-4-ol

The same method as in Reference Example 6 was conducted using 5,6,7,8-tetrahydro-4H-furo[2,3-c]azepin-4-ol provided with Reference Example 37 instead of 4,5,6,7-tetrahydrothieno[2,3-c]pyridin-4-ol and was conducted using ethylbromoacetate instead of methyl iodide to give the objective compound.
MS spectrum: 240[M+H]$^+$

Reference Example 43

7-(2-Hydroxy-2-methyl-1-propyl)-5,6,7,8-tetrahydro-4H-furo[2,3-c]azepin-4-ol The same method as Reference Example 6 was conducted using 5,6,7,8-tetrahydro-4H-furo[2,3-c]azepin-4-ol provided with Reference Example 37 instead of 4,5,6,7-tetrahydrothieno[2,3-c]pyridin-4-ol and was conducted using 1-chloro-2-methyl-2-propanol instead of methyl iodide to give the objective compound.
MS spectrum: 226[M+H]$^+$

Reference Example 44

2-Methyl-5,6,7,8-tetrahydro-4H-furo[2,3-c]azepin-4-ol

The same method as in Reference Example 35 was conducted using 5-methyl-2-furaldehyde instead of 2-thiophenaldehyde to give the objective compound.
MS spectrum: 168[M+H]$^+$

Reference Example 45

6-Ethyl-5,6,7,8-tetrahydro-4H-thieno[2,3-d]azepin-4-ol

The same method as in Reference Example 6 was conducted using 5,6,7,8-tetrahydro-4H-thieno[2,3-d]azepin-4-ol provided with Reference Example 29 instead of 4,5,6,7-tetrahydrothieno[2,3-c]pyridin-4-ol and was conducted using ethyl iodide instead of methyl iodide to give the objective compound.
MS spectrum: 198[M+H]$^+$

Reference Example 46

5,6,7,8-Tetrahydro-4H-thieno[3,2-d]azepin-4-ol

The same method as in Reference Example 29 (steps 1 to 5) was conducted using 2-(thieno-2-yl)ethylamine instead of 2-(thieno-3-yl)ethylamine to give the objective compound.
MS spectrum: 170[M+H]$^+$

Reference Example 47

6-Methyl-5,6,7,8-tetrahydro-4H-thieno[3,2-d]azepin-4-ol

The same method as in Reference Example 6) was conducted using 5,6,7,8-tetrahydro-4H-thieno[3,2-d]azepin-4-ol provided with Reference Example 46 instead of 4,5,6,7-tetrahydrothieno[2,3-c]pyridin-4-ol to give the objective compound.

MS spectrum: 184[M+H]$^+$

Reference Example 48

6-Ethyl-5,6,7,8-tetrahydro-4H-thieno[3,2-d]azepin-4-ol

The same method as in Reference Example 6 was conducted using 5,6,7,8-tetrahydro-4H-thieno[3,2-d]azepin-4-ol provided with Reference Example 46 instead of 4,5,6,7-tetrahydrothieno[2,3-c]pyridin-4-ol and was conducted using ethyl iodide instead of methyl iodide to give the objective compound.

MS spectrum: 198[M+H]$^+$

Reference Example 49

(+)-6-Ethoxycarbonyl-4,5,6,7-tetrahydrofuro[2,3-c]pyridin-4-ol

6-Ethoxycarbonyl-4,5,6,7-tetrahydrofuro[2,3-c]-pyridin-4-one (0.42 g) prepared in Reference Example 1 (Step 4) and 0.066 g of chloro[(1R,2R)—N-(p-toluenesulfonyl)-1,2-diphenylethanediamine](hexamethylbenzene)ruthenium(II) were prepared in an argon atmosphere and 0.87 g of a 5/2 (in molar ratio) mixture of formic acid/triethylamine was added thereto followed by stirring under a room temperature condition for 65 hours. The reaction mixture was diluted with water and subjected to extraction with ethyl acetate. The organic layer was washed with an aqueous solution of sodium hydrogen carbonate and a saturated solution of sodium chloride and dried over anhydrous magnesium sulfate and the solvent was evaporated therefrom in vacuo. The resulting residue was purified by silica gel column chromatography to give 0.42 g of the objective compound.

Pale yellow liquid, MS spectrum: 212[M+H]$^+$, 99.0% ee

Specific rotation $[\alpha]_D$=+43.5° (25° C., c=1.55, MeOH)

Reference Example 50

(+)-6-Methyl-4,5,6,7-tetrahydrofuro[2,3-c]pyridin-4-ol

A solution of 0.42 g of (+)-6-ethoxycarbonyl-4,5,6,7-tetrahydrofuro[2,3-c]pyridin-4-ol prepared in Reference Example 49 in 8 mL of dry THF was slowly dropped into an ice-cooled solution of 0.12 g of lithium aluminum hydride in 4 mL of dry THF. The reaction solution was gradually heated followed by heating to reflux for 60 minutes. The reaction solution was cooled, ice was gradually added thereto so that an excess of lithium aluminum hydride was decomposed and the mixture was subjected to extraction with ethyl acetate. The organic layer was washed with a saturated solution of sodium chloride and dried over anhydrous magnesium sulfate and the solvent was evaporated therefrom in vacuo. The residue was purified by silica gel column chromatography to give 0.27 g of the objective compound.

Pale yellow liquid, MS spectrum: 154[M+H]$^+$

Specific rotation $[\alpha]_D$=+11.2° (25° C., c=0.93, MeOH)

Reference Example 51

(+)-7-Ethoxycarbonyl-5,6,7,8-tetrahydro-4H-furo[2,3-c]azepin-4-ol

7-Ethoxycarbonyl-5,6,7,8-tetrahydrofuro[2,3-c]-azepin-4-one (0.80 g) prepared in Reference Example 19 (Step 5) and 0.11 g of chloro[(1R,2R)—N-(p-toluenesulfonyl)-1,2-diphenylethanediamine](mesitylene)ruthenium(II) were prepared in an argon atmosphere and 1.55 g of a 5/2 (in molar ratio) mixture of formic acid/triethylamine was added thereto followed by stirring under a room temperature condition for 24 hours. The reaction solution was diluted with water followed by extracting with ethyl acetate. The organic layer was washed with an aqueous solution of sodium hydrogen carbonate and a saturated solution of sodium chloride and dried over anhydrous magnesium sulfate and the solvent was evaporated therefrom in vacuo. The residue was purified by silica gel column chromatography to give 0.90 g of the objective compound.

Pale yellow liquid, MS spectrum: 226[M+H]$^+$, 99.0% ee

Specific rotation $[\alpha]_D$=+20.7° (25° C., c=0.91, MeOH)

Reference Example 52

(+)-7-Methyl-5,6,7,8-tetrahydro-4H-furo[2,3-c]azepin-4-ol

A solution of 0.90 g of (+)-7-ethoxycarbonyl-5,6,7,8-tetrahydro-4H-furo[2,3-c]azepin-4-ol prepared in Reference Example 51 in 20 mL of dry THF was slowly dropped into an ice-cooled solution of 0.20 g of lithium aluminum hydride in 10 mL of dry THF. The reaction solution was gradually heated followed by heating to reflux for 30 minutes. Then the reaction solution was cooled, ice was gradually added thereto so that an excess of lithium aluminum hydride was decomposed and the mixture was subjected to extraction with ethyl acetate. The organic layer was washed with a saturated solution of sodium chloride and dried over anhydrous magnesium sulfate and the solvent was evaporated therefrom in vacuo. The residue was purified by silica gel column chromatography to give 0.58 g of the objective compound.

Pale yellow liquid, MS spectrum: 168[M+H]$^+$

Specific rotation $[\alpha]_D$=+26.2° (25° C., c=1.24, MeOH)

Reference Example 53

(−)-7-Ethoxycarbonyl-5,6,7,8-tetrahydro-4H-furo[2,3-c]azepin-4-ol

The same method as in Reference Example 51 was conducted using chloro[(1S,2S)—N-(p-toluenesulfonyl)-1,2-diphenylethanediamine](mesitylene)ruthenium(II) instead of chloro[(1R,2R)—N-(p-toluenesulfonyl)-1,2-diphenylethanediamine](mesitylene)ruthenium(II) to give the objective compound.

Pale yellow liquid, MS spectrum: 226[M+H]$^+$, 98.7% ee

Specific rotation $[\alpha]_D$=−15.2° (25° C., c=1.02, MeOH)

Reference Example 54

(−)-7-Methyl-5,6,7,8-tetrahydro-4H-furo[2,3-c]
azepin-4-ol

The same method as in Reference Example 52 was conducted using (−)-7-ethoxycarbonyl-5,6,7,8-tetrahydro-4H-furo[2,3-c]azepin-4-ol provided with Reference Example 53 instead of (+)-7-ethoxycarbonyl-5,6,7,8-tetrahydro-4H-furo[2,3-c]azepin-4-ol to give the objective compound.

Pale yellow liquid, MS spectrum: 168[M+H]$^+$
Specific rotation $[\alpha]_D$=−26.7° (25° C., c=1.81, MeOH)

Reference Example 55

(+)-7-Ethoxycarbonyl-2-methyl-5,6,7,8-tetrahydro-
4H-furo[2,3-c]azepin-4-ol

The same method as in Reference Example 51 was conducted using 7-ethoxycarbonyl-2-methyl-5,6,7,8-tetrahydrofuro[2,3-c]azepin-4-one provided with Reference Example 20 (step 5) instead of 7-ethoxycarbonyl-5,6,7,8-tetrahydrofuro[2,3-c]azepin-4-one to give the objective compound.

Pale yellow liquid, MS spectrum: 240[M+H]$^+$, 99.9% ee
Specific rotation $[\alpha]_D$=+2.3° (25° C., c=0.84, MeOH)

Reference Example 56

(+)-2,7-Dimethyl-5,6,7,8-tetrahydro-4H-furo[2,3-c]
azepin-4-ol

The same method as in Reference Example 52 was conducted using (+)-7-ethoxycarbonyl-2-methyl-5,6,7,8-tetrahydro-4H-furo[2,3-c]azepin-4-ol provided with Reference Example 55 instead of (+)-7-ethoxycarbonyl-5,6,7,8-tetrahydro-4H-furo[2,3-c]azepin-4-ol to give the objective compound.

Pale yellow liquid, MS spectrum: 182[M+H]$^+$
Specific rotation $[\alpha]_D$=+22.1° (25° C., c=0.95, MeOH)

Reference Example 57

(−)-7-Ethoxycarbonyl-2-methyl-5,6,7,8-tetrahydro-
4H-furo[2,3-c]azepin-4-ol

The same method as in Reference Example 51 was conducted using 7-ethoxycarbonyl-2-methyl-5,6,7,8-tetrahydrofuro[2,3-c]azepin-4-one (Reference Example 20 (step 5)) instead of 7-ethoxycarbonyl-5,6,7,8-tetrahydrofuro[2,3-c]azepin-4-one and was conducted using chloro[(1S,2S)—N-(p-toluenesulfonyl)-1,2-diphenylethanediamine](mesitylene)ruthenium(II) instead of chloro[(1R,2R)—N-(p-toluenesulfonyl)-1,2-diphenylethanediamine](mesitylene)ruthenium(II) to give the objective compound.

Pale yellow liquid, MS spectrum: 240[M+H]$^+$, 99.0% ee
Specific rotation $[\alpha]_D$=−2.5° (25° C., c=1.11, MeOH)

Reference Example 58

(−)-2,7-Dimethyl-5,6,7,8-tetrahydro-4H-furo[2,3-c]
azepin-4-ol

The same method as in Reference Example 52 was conducted using (−)-7-ethoxycarbonyl-2-methyl-5,6,7,8-tetrahydro-4H-furo[2,3-c]azepin-4-ol provided with Reference Example 57 instead of (+)-7-ethoxycarbonyl-5,6,7,8-tetrahydro-4H-furo[2,3-c]azepin-4-ol to give the objective compound.

Pale yellow liquid, MS spectrum: 182[M+H]$^+$
Specific rotation $[\alpha]_D$=−14.7° (25° C., c=0.97, MeOH)

Example 1

6-Methyl-4-(naphthalen-1-yloxy)-4,5,6,7-tetrahy-
drothieno[2,3-c]pyridine

60% Sodium hydride (96 mg) was washed with n-hexane and 5 mL of DMSO was added thereto. To the resulting suspension was added 340 mg of 6-methyl-4,5,6,7-tetrahydrothieno[2,3-c]-pyridin-4-ol (Reference Example 6) followed by stirring at room temperature for 30 minutes. To this mixed solution was added 385 mg of potassium benzoate followed by stirring at room temperature for 30 minutes more. Into this reaction solution was slowly dropped 351 mg of 1-fluoronaphthalene followed by stirring at 80° C. overnight. The reaction solution was poured over 30 mL of ice water followed by extracting with ethyl acetate. The organic layer was washed with water and dried over anhydrous magnesium sulfate and the solvent was evaporated therefrom in vacuo. The residue was purified by silica gel column chromatography to give 150 mg of the objective compound.

Pale yellow powder, MS spectrum: 296[M+H]$^+$

Example 2

5-Methyl-7-(naphthalen-1-yloxy)-4,5,6,7-tetrahy-
drothieno[3,2-c]pyridine

The same method as in Example 1 was conducted using 5-methyl-4,5,6,7-tetrahydrothieno[3,2-c]pyridin-7-ol (Reference Example 14) instead of 6-methyl-4,5,6,7-tetrahydrothieno[2,3-c]pyridin-4-ol (Reference Example 6) to give the objective compound.

Colorless powder, MS spectrum: 296[M+H]$^+$

Example 3

4-(3-Fluorophenyloxy)-6-methyl-4,5,6,7-tetrahy-
drothieno[2,3-c]pyridine hydrochloride 60% Sodium hydride (96 mg) was washed with n-hexane and 5 mL of DMSO was added thereto. To the resulting suspension was added 340 mg of 6-methyl-4,5,6,7-tetrahydrothieno[2,3-c]-pyridin-4-ol (Reference Example 6) followed by stirring at room temperature for 30 minutes. To this mixed solution was added 385 mg of potassium benzoate followed by stirring at room temperature for 30 minutes more. Into this reaction solution was slowly dropped 251 mg of 1,3-difluorobenzene followed by stirring at 80° C. overnight. The reaction solution was poured over 30 mL of ice water followed by extracting with ethyl acetate. The organic layer was washed with water and dried over anhydrous magnesium sulfate and the solvent was evaporated therefrom in vacuo. The residue was purified by silica gel column chromatography to give a free substance of the objective compound.

The resulting free substance was dissolved in 5 mL of ethyl acetate and 1 equivalent of a hydrochloric acid/ethyl acetate solution was dropped thereinto followed by stirring for 30 minutes. The mixed solution was concentrated to give 220 mg of the objective compound.

Pale yellow powder, MS spectrum: 264[M+H]$^+$

Example 4

7-(3-Fluorophenyloxy)-5-methyl-4,5,6,7-tetrahydrothieno[3,2-c]pyridine hydrochloride

The same method as in Example 3 was conducted using 5-methyl-4,5,6,7-tetrahydrothieno[3,2-c]pyridin-7-ol (Reference Example 14) instead of 6-methyl-4,5,6,7-tetrahydrothieno[2,3-c]pyridin-4-ol (Reference Example 6) to give the objective compound.
Colorless powder, MS spectrum: 264[M+H]$^+$

Example 5

4-(2-Methoxyphenyloxy)-6-methyl-4,5,6,7-tetrahydrothieno[2,3-c]pyridine

The same method as in Reference Example 1 was conducted using o-fluoroanisole instead of 1-fluoronaphthalene to give the objective compound.
Colorless liquid, MS spectrum: 276[M+H]$^+$

Example 6

7-(2-Methoxyphenyloxy)-5-methyl-4,5,6,7-tetrahydrothieno[3,2-c]pyridine hydrochloride

The same method as in Reference Example 3 was conducted using 5-methyl-4,5,6,7-tetrahydrothieno[3,2-c]pyridin-7-ol (Reference Example 14) instead of 6-methyl-4,5,6,7-tetrahydrothieno[2,3-c]pyridin-4-ol (Reference Example 6) and was conducted using o-fluoroanisole instead of 1,3-difluorobenzene to give the objective compound.
Brown liquid, MS spectrum: 313[M+H]$^+$

Example 7

4-(2,3-Dichlorophenyloxy)-6-methyl-4,5,6,7-tetrahydrothieno[2,3-c]pyridine

The same method as in Example 1 was conducted using 2,3-dichloro-1-fluorobenzene instead of 1-fluoronaphthalene to give the objective compound.
Colorless powder, MS spectrum: 314[M+H]$^+$

Example 8

4-(3,4-Dichlorophenyloxy)-6-methyl-4,5,6,7-tetrahydrothieno[2,3-c]pyridine

The same method as in Example 1 was conducted using 3,4-dichloro-1-fluorobenzene instead of 1-fluoronaphthalene to give the objective compound.
Colorless powder, MS spectrum: 314[M+H]$^+$

Example 9

7-(2,3-Dichlorophenyloxy)-5-methyl-4,5,6,7-tetrahydrothieno[3,2-c]pyridine

The same method as in Example 1 was conducted using 5-methyl-4,5,6,7-tetrahydrothieno[3,2-c]pyridin-7-ol (Reference Example 14) instead of 6-methyl-4,5,6,7-tetrahydrothieno[2,3-c]pyridin-4-ol (Reference Example 6) and was conducted using 2,3-dichloro-1-fluorobenzene instead of 1-fluoronaphthalene to give the objective compound.
Colorless powder, MS spectrum: 314[M+H]$^+$

Example 10

7-(3,4-Dichlorophenyloxy)-5-methyl-4,5,6,7-tetrahydrothieno[3,2-c]pyridine

The same method as in Example 1 was conducted using 5-methyl-4,5,6,7-tetrahydrothieno[3,2-c]pyridin-7-ol (Reference Example 14) instead of 6-methyl-4,5,6,7-tetrahydrothieno[2,3-c]pyridin-4-ol (Reference Example 6) and was conducted using 3,4-dichloro-1-fluorobenzene instead of 1-fluoronaphthalene to give the objective compound.
Colorless powder, MS spectrum: 314[M+H]$^+$

Example 11

7-(4-Bromonaphthalen-1-yloxy)-5-methyl-4,5,6,7-tetrahydrothieno[3,2-c]pyridine

The same method as in Example 1 was conducted using 5-methyl-4,5,6,7-tetrahydrothieno[3,2-c]pyridin-7-ol (Reference Example 14) instead of 6-methyl-4,5,6,7-tetrahydrothieno[2,3-c]pyridin-4-ol (Reference Example 6) and was conducted using 1-bromo-4-fluoronaphthalene instead of 1-fluoronaphthalene to give the objective compound.
Colorless powder, MS spectrum: 374[M+H]$^+$

Example 12

4-(4-Bromonaphthalen-1-yloxy)-6-methyl-4,5,6,7-tetrahydrothieno[2,3-c]pyridine hydrochloride

The same method as in Example 3 was conducted using 1-bromo-4-fluoronaphthalene instead of 1,3-difluorobenzene to give the objective compound.
Colorless powder, MS spectrum: 374[M+H]$^+$

Example 13

6-Methyl-4-(3-nitrophenyloxy)-4,5,6,7-tetrahydrothieno[2,3-c]pyridine

The same method as in Example 1 was conducted using 1-fluoro-3-nitrobenzene instead of 1-fluoronaphthalene to give the objective compound.
Colorless powder, MS spectrum: 291[M+H]$^+$

Example 14

4-(3-Cyanophenyloxy)-6-methyl-4,5,6,7-tetrahydrothieno[2,3-c]pyridine

The same method as in Example 1 was conducted using 3-fluorobenzo carbonitrile instead of 1-fluoronaphthalene to give the objective compound.
Yellow powder, MS spectrum: 271[M+H]$^+$

Example 15

6-Methyl-4-[3-(trifluoromethyl)phenyloxy]-4,5,6,7-tetrahydrothieno[2,3-c]pyridine

The same method as in Example 1 was conducted using 3-fluorobenzotrifluoride instead of 1-fluoronaphthalene to give the objective compound.
Yellow powder, MS spectrum: 314[M+H]$^+$

Example 16

5-Methyl-7-(3-nitrophenyloxy)-4,5,6,7-tetrahydrothieno[3,2-c]pyridine

The same method as in Example 1 was conducted using 5-methyl-4,5,6,7-tetrahydrothieno[3,2-c]pyridin-7-ol (Reference Example 14) instead of 6-methyl-4,5,6,7-tetrahydrothieno[2,3-c]pyridin-4-ol (Reference Example 6) and 1-fluoro-3-nitro benzene instead of 1-fluoronaphthalene to give the objective compound.
Yellow powder, MS spectrum: 291[M+H]$^+$

Example 17

7-(3-Cyanophenyloxy)-5-methyl-4,5,6,7-tetrahydrothieno[3,2-c]pyridine

The same method as in Example 1 was conducted using 5-methyl-4,5,6,7-tetrahydrothieno[3,2-c]pyridin-7-ol (Reference Example 14) instead of 6-methyl-4,5,6,7-tetrahydrothieno[2,3-c]pyridin-4-ol (Reference Example 6) and was conducted using 3-fluorobenzo carbonitrile instead of 1-fluoronaphthalene to give the objective compound.
Yellow powder, MS spectrum: 271[M+H]$^+$

Example 18

5-Methyl-7-[3-(trifluoromethyl)phenyloxy]-4,5,6,7-tetrahydrothieno[3,2-c]pyridine The same method as in Example 1 was conducted using 5-methyl-4,5,6,7-tetrahydrothieno[3,2-c]pyridin-7-ol (Reference Example 14) instead of 6-methyl-4,5,6,7-tetrahydrothieno[2,3-c]pyridin-4-ol (Reference Example 6) and was conducted using 3-fluorobenzo trifluoride instead of 1-fluoronaphthalene to give the objective compound.
Yellow powder, MS spectrum: 314[M+H]$^+$

Example 19

4-(2,3-Dichlorophenyloxy)-6-methyl-4,5,6,7-tetrahydrofuro[2,3-c]pyridine

The same method as in Example 1 was conducted using 6-methyl-4,5,6,7-tetrahydrofuro[2,3-c]pyridin-4-ol (Reference Example 1) instead of 6-methyl-4,5,6,7-tetrahydrothieno[2,3-c]pyridin-4-ol (Reference Example 6) and was conducted using 2,3-dichloro-1-fluorobenzene instead of 1-fluoronaphthalene to give the objective compound.
Pale yellow solid, MS spectrum: 298[M+H]$^+$

Example 20

6-Methyl-4-(naphthalen-1-yloxy)-4,5,6,7-tetrahydrofuro[2,3-c]pyridine

The same method as in Example 1 was conducted using 6-methyl-4,5,6,7-tetrahydrofuro[2,3-c]pyridin-4-ol (Reference Example 1) instead of 6-methyl-4,5,6,7-tetrahydrothieno[2,3-c]pyridin-4-ol (Reference Example 6) to give the objective compound.
Colorless solid, MS spectrum: 280[M+H]$^+$

Example 21

4-(3,4-Dichlorophenyloxy)-6-methyl-4,5,6,7-tetrahydrofuro[2,3-c]pyridine hydrochloride The same method as in Example 3 was conducted using 6-methyl-4,5,6,7-tetrahydrofuro[2,3-c]pyridin-4-ol (Reference Example 1) instead of 6-methyl-4,5,6,7-tetrahydrothieno[2,3-c]pyridin-4-ol (Reference Example 6) and was conducted using 3,4-dichloro-1-fluorobenzene instead of 1,3-difluorobenzene to give the objective compound.
Ecru solid, MS spectrum: 298[M+H]$^+$

Example 22

4-(4-Bromonaphthalen-1-yloxy)-6-methyl-4,5,6,7-tetrahydrofuro[2,3-c]pyridine hydrochloride The same method as in Example 3 was conducted using 6-methyl-4,5,6,7-tetrahydrofuro[2,3-c]pyridin-4-ol (Reference Example 1) instead of 6-methyl-4,5,6,7-tetrahydrothieno[2,3-c]pyridin-4-ol (Reference Example 6) and was conducted using 1-bromo-4-fluoronaphthalene instead of 1,3-difluorobenzene to give the objective compound.
Ecru solid, MS spectrum: 358[M+H]$^+$

Example 23

4-(2,3-Dichlorophenyloxy)-6-ethyl-4,5,6,7-tetrahydrothieno[2,3-c]pyridine hydrochloride The same method as in Example 3 was conducted using 6-ethyl-4,5,6,7-tetrahydrothieno[2,3-c]pyridin-4-ol (Reference Example 7) instead of 6-methyl-4,5,6,7-tetrahydrothieno[2,3-c]pyridin-4-ol (Reference Example 6) and was conducted using 2,3-dichloro-1-fluorobenzene instead of 1,3-difluorobenzene to give the objective compound.
Colorless powder, MS spectrum: 328[M+H]$^+$

Example 24

4-(3,4-Dichlorophenyloxy)-6-ethyl-4,5,6,7-tetrahydrothieno[2,3-c]pyridine hydrochloride The same method as in Example 3 was conducted using 6-ethyl-4,5,6,7-tetrahydrothieno[2,3-c]pyridin-4-ol (Reference Example 7) instead of 6-methyl-4,5,6,7-tetrahydrothieno[2,3-c]pyridin-4-ol (Reference Example 6) and was conducted using 3,4-dichloro-1-fluorobenzene instead of 1,3-difluorobenzene to give the objective compound.
Colorless powder, MS spectrum: 328[M+H]$^+$

Example 25

5-Methyl-7-(naphthalen-1-yloxy)-4,5,6,7-tetrahydrothieno[3,2-c]pyridine hydrochloride The same method as in Example 3 was conducted using 5-methyl-4,5,6,7-tetrahydrothieno[3,2-c]pyridin-7-ol (Reference Example 14) instead of 6-methyl-4,5,6,7-tetrahydrothieno[2,3-c]pyridin-4-ol (Reference Example 6) and was conducted using 1-fluoronaphthalene instead of 1,3-difluorobenzene to give the objective compound.
Colorless powder, MS spectrum: 296[M+H]$^+$

Example 26

5-Cyclopropylmethyl-7-(naphthalen-1-yloxy)-4,5,6,
7-tetrahydrothieno[3,2-c]pyridine hydrochloride The same method as in Example 3 was conducted using 5-cyclopropylmethyl-4,5,6,7-tetrahydrothieno[3,2-c]pyridin-7-ol (Reference Example 15) instead of 6-methyl-4,5,6,7-tetrahydrothieno[2,3-c]pyridin-4-ol (Reference Example 6) and was conducted using 1-fluoronaphthalene instead of 1,3-difluorobenzene to give the objective compound.
Colorless powder, MS spectrum: 336[M+H]$^+$

Example 27

7-(3,4-Dichlorophenyloxy)-5-cyclopropylmethyl-4,
5,6,7-tetrahydrothieno[3,2-c]pyridine The same method as in Example 1 was conducted using 5-cyclopropylmethyl-4,5,6,7-tetrahydrothieno[3,2-c]pyridin-7-ol (Reference Example 15) instead of 6-methyl-4,5,6,7-tetrahydrothieno[2,3-c]pyridin-4-ol (Reference Example 6) and was conducted using 3,4-dichloro-1-fluorobenzene instead of 1-fluoronaphthalene to give the objective compound.
Colorless powder, MS spectrum: 354[M+H]$^+$

Example 28

5-Allyl-7-(naphthalen-1-yloxy)-4,5,6,7-tetrahydrothieno[3,2-c]pyridine hydrochloride The same method as in Example 3 was conducted using 5-allyl-4,5,6,7-tetrahydrothieno[3,2-c]pyridin-7-ol (Reference Example 16) instead of 6-methyl-4,5,6,7-tetrahydrothieno[2,3-c]pyridin-4-ol (Reference Example 6) and was conducted using 1-fluoronaphthalene instead of 1,3-difluorobenzene to give the objective compound.
Colorless powder, MS spectrum: 322[M+H]$^+$

Example 29

5-Allyl-7-(2,3-dichlorophenyloxy)-4,5,6,7-tetrahydrothieno[3,2-c]pyridine hydrochloride The same method as in Example 3 was conducted using 5-allyl-4,5,6,7-tetrahydrothieno[3,2-c]pyridin-7-ol (Reference Example 16) instead of 6-methyl-4,5,6,7-tetrahydrothieno[2,3-c]pyridin-4-ol (Reference Example 6) and was conducted using 2,3-dichloro-1-fluorobenzene instead of 1,3-difluorobenzene to give the objective compound.
Colorless powder, MS spectrum: 340[M+H]$^+$

Example 30

5-Allyl-7-(3,4-dichlorophenyloxy)-4,5,6,7-tetrahydrothieno[3,2-c]pyridine hydrochloride The same method as in Example 3 was conducted using 5-allyl-4,5,6,7-tetrahydrothieno[3,2-c]pyridin-7-ol (Reference Example 16) instead of 6-methyl-4,5,6,7-tetrahydrothieno[2,3-c]pyridin-4-ol (Reference Example 6) and was conducted using 3,4-dichloro-1-fluorobenzene instead of 1,3-difluorobenzene to give the objective compound.
Colorless powder, MS spectrum: 340[M+H]$^+$

Example 31

5-(2-Fluoroethyl)-7-(naphthalen-1-yloxy)-4,5,6,7-tetrahydrothieno[3,2-c]pyridine hydrochloride The same method as in Example 3 was conducted using 5-(2-fluoroethyl)-4,5,6,7-tetrahydrothieno[3,2-c]pyridin-7-ol (Reference Example 17) instead of 6-methyl-4,5,6,7-tetrahydrothieno[2,3-c]pyridin-4-ol (Reference Example 6) and was conducted using 1-fluoronaphthalene instead of 1,3-difluorobenzene to give the objective compound.
Pale yellow liquid, MS spectrum: 328[M+H]$^+$

Example 32

7-(2,3-Dichlorophenyloxy)-5-(2-fluoroethyl)-4,5,6,
7-tetrahydrothieno[3,2-c]pyridine The same method as in Example 1 was conducted using 5-(2-fluoroethyl)-4,5,6,7-tetrahydrothieno[3,2-c]pyridin-7-ol (Reference Example 17) instead of 6-methyl-4,5,6,7-tetrahydrothieno[2,3-c]pyridin-4-ol (Reference Example 6) and was conducted using 2,3-dichloro-1-fluorobenzene instead of 1-fluoronaphthalene to give the objective compound.
Colorless powder, MS spectrum: 346[M+H]$^+$

Example 33

7-(3,4-Dichlorophenyloxy)-5-(2-fluoroethyl)-4,5,6,
7-tetrahydrothieno[3,2-c]pyridine hydrochloride The same method as in Reference Example 3 was conducted using 5-(2-fluoroethyl)-4,5,6,7-tetrahydrothieno[3,2-c]pyridin-7-ol (Reference Example 17) instead of 6-methyl-4,5,6,7-tetrahydrothieno[2,3-c]pyridin-4-ol (Reference Example 6) and was conducted using 3,4-dichloro-1-fluorobenzene instead of 1,3-difluorobenzene to give the objective compound.
Colorless powder, MS spectrum: 346[M+H]$^+$

Example 34

5-Methyl-7-(6-methylnaphthalene-2-yloxy)-4,5,6,7-tetrahydrothieno[3,2-c]pyridine hydrochloride The same method as in Example 3 was conducted using 5-methyl-4,5,6,7-tetrahydrothieno[3,2-c]pyridin-7-ol (Reference Example 14) instead of 6-methyl-4,5,6,7-tetrahydrothieno[2,3-c]pyridin-4-ol (Reference Example 6) and was conducted using 2-fluoro-6-methylnaphthalene instead of 1,3-difluorobenzene to give the objective compound.
Colorless powder, MS spectrum: 310[M+H]$^+$

Example 35

7-(3,4-Dichlorophenyloxy)-4,5,6,7-tetrahydrothieno[3,2-c]pyridine

The same method as in Example 1 was conducted using 4,5,6,7-tetrahydrothieno[3,2-c]pyridin-7-ol (Reference Example 13) instead of 6-methyl-4,5,6,7-tetrahydrothieno[2,3-c]pyridin-4-ol (Reference Example 6) and was conducted using 3,4-dichloro-1-fluorobenzene instead of 1-fluoronaphthalene to give the objective compound.
Colorless powder, MS spectrum: 300[M+H]$^+$

Example 36

7-(Naphthalen-1-yloxy)-4,5,6,7-tetrahydrothieno[3,2-c]pyridine hydrochloride

The same method as in Example 3 was conducted using 4,5,6,7-tetrahydrothieno[3,2-c]pyridin-7-ol (Reference Example 13) instead of 6-methyl-4,5,6,7-tetrahydrothieno[2,3-c]pyridin-4-ol (Reference Example 6) and was conducted using 1-fluoronaphthalene instead of 1,3-difluorobenzene to give the objective compound.

Colorless powder, MS spectrum: 282[M+H]$^+$

Example 37

7-(4-Bromonaphthalen-1-yloxy)-4,5,6,7-tetrahydrothieno[3,2-c]pyridine

The same method as in Example 1 was conducted using 4,5,6,7-tetrahydrothieno[3,2-c]pyridin-7-ol (Reference Example 13) instead of 6-methyl-4,5,6,7-tetrahydrothieno[2,3-c]pyridin-4-ol (Reference Example 6) and was conducted using 1-bromo-4-fluoronaphthalene instead of 1-fluoronaphthalene to give the objective compound.

Colorless powder, MS spectrum: 360[M+H]$^+$

Example 38

6-Methyl-4-(quinolin-8-yloxy)-4,5,6,7-tetrahydrofuro[2,3-c]pyridine

In an argon atmosphere, a solution of 40 mg of 6-methyl-4,5,6,7-tetrahydrofuro[2,3-c]pyridin-4-ol (Reference Example 1), 45.4 mg of 8-hydroxyquinoline and 82.1 mg of triphenyl phosphine in 1 mL of anhydrous THF was prepared. Into this mixed solution was dropped 136 mg of a 40% solution of diethyl azodicarboxylate/toluene in an argon atmosphere followed by stirring at room temperature for 2 hours more. The residue prepared by concentration of the reaction solution in vacuo was purified by silica gel column chromatography to give 15.8 mg of yellow oily product.

Yellow liquid, MS spectrum: 303[M+Na]$^+$

Example 39

4-(3,4-Dichlorophenyloxy)-4,5,6,7-tetrahydrothieno[2,3-c]pyridine

The same method as in Example 1 was conducted using 4,5,6,7-tetrahydrothieno[2,3-c]pyridin-4-ol (Reference Example 5) instead of 6-methyl-4,5,6,7-tetrahydrothieno[2,3-c]pyridin-4-ol (Reference Example 6) and was conducted using 3,4-dichloro-1-fluorobenzene instead of 1-fluoronaphthalene to give the objective compound.

Pale yellow solid, MS spectrum: 300[M+H]$^+$

Example 40

4-(Naphthalen-1-yloxy)-4,5,6,7-tetrahydrothieno[2,3-c]pyridine hydrochloride

The same method as in Example 3 was conducted using 4,5,6,7-tetrahydrothieno[2,3-c]pyridin-4-ol (Reference Example 5) instead of 6-methyl-4,5,6,7-tetrahydrothieno[2,3-c]pyridin-4-ol (Reference Example 6) and was conducted using 1-fluoronaphthalene instead of 1,3-difluorobenzene to give the objective compound.

Colorless powder, MS spectrum: 282[M+H]$^+$

Example 41

4-(4-Bromonaphthalen-1-yloxy)-4,5,6,7-tetrahydrothieno[2,3-c]pyridine

The same method as in Example 1 was conducted using 4,5,6,7-tetrahydrothieno[2,3-c]pyridin-4-ol (Reference Example 5) instead of 6-methyl-4,5,6,7-tetrahydrothieno[2,3-c]pyridin-4-ol (Reference Example 6) and was conducted using 1-bromo-4-fluoronaphthalene instead of 1-fluoronaphthalene to give the objective compound.

Pale yellow powder, MS spectrum: 360[M+H]$^+$

Example 42

4-(3-Cyanophenyloxy)-6-methyl-4,5,6,7-tetrahydrofuro[2,3-c]pyridine

The same method as in Example 1 was conducted using 6-methyl-4,5,6,7-tetrahydrofuro[2,3-c]pyridin-4-ol (Reference Example 1) instead of 6-methyl-4,5,6,7-tetrahydrothieno[2,3-c]pyridin-4-ol (Reference Example 6) and was conducted using 3-fluorobenzonitrile instead of 1-fluoronaphthalene to give the objective compound.

Pale yellow solid, MS spectrum: 255[M+H]$^+$

Example 43

6-Methyl-4-[3-(trifluoromethyl)phenyloxy]-4,5,6,7-tetrahydrofuro[2,3-c]pyridine hydrochloride

The same method as in Example 3 was conducted using 6-methyl-4,5,6,7-tetrahydrofuro[2,3-c]pyridin-4-ol (Reference Example 1) instead of 6-methyl-4,5,6,7-tetrahydrothieno[2,3-c]pyridin-4-ol (Reference Example 6) and was conducted using 3-fluorobenzotrifluoride instead of 1,3-difluorobenzene to give the objective compound.

Yellow powder, MS spectrum: 298[M+H]$^+$

Example 44

6-Methyl-4-(3-nitrophenyloxy)-4,5,6,7-tetrahydrofuro[2,3-c]pyridine hydrochloride

The same method as in Example 3 was conducted using 6-methyl-4,5,6,7-tetrahydrofuro[2,3-c]pyridin-4-ol (Reference Example 1) instead of 6-methyl-4,5,6,7-tetrahydrothieno[2,3-c]pyridin-4-ol (Reference Example 6) and was conducted using 1-fluoro-3-nitrobenzene instead of 1,3-difluorobenzene to give the objective compound.

Yellow powder, MS spectrum: 275[M+H]$^+$

Example 45

6-Methyl-4-(6-methylnaphthalen-2-yloxy)-4,5,6,7-tetrahydrofuro[2,3-c]pyridine hydrochloride

The same method as in Example 3 was conducted using 6-methyl-4,5,6,7-tetrahydrofuro[2,3-c]pyridin-4-ol (Reference Example 1) instead of 6-methyl-4,5,6,7-tetrahydrothieno[2,3-c]pyridin-4-ol (Reference Example 6) and was conducted using 2-fluoro-6-methylnaphthalene instead of 1,3-difluorobenzene to give the objective compound.

Yellow powder, MS spectrum: 294[M+H]$^+$

Example 46

4-(4-Bromophenyloxy)-6-methyl-4,5,6,7-tetrahydrofuro[2,3-c]pyridine hydrochloride

The same method as in Example 3 was conducted using 6-methyl-4,5,6,7-tetrahydrofuro[2,3-c]pyridin-4-ol (Reference Example 1) instead of 6-methyl-4,5,6,7-tetrahydrothieno[2,3-c]pyridin-4-ol (Reference Example 6) and was conducted using 1-bromo-4-fluorobenzene instead of 1,3-difluorobenzene to give the objective compound.

Yellow powder, MS spectrum: 308[M+H]$^+$

Example 47

4-(4-Chloro-3-methylphenyloxy)-6-methyl-4,5,6,7-tetrahydrofuro[2,3-c]pyridine hydrochloride

In an argon atmosphere, a solution of 200 mg of 6-methyl-4,5,6,7-tetrahydrofuro[2,3-c]pyridin-4-ol (Reference Example 1), 223 mg of 4-chloro-3-methylphenol and 514 mg of triphenyl phosphine in 5 mL of anhydrous THF was prepared. Into this mixed solution was dropped 853 mg of a 40% solution of diethyl azodicarboxylate in toluene in an argon atmosphere followed by stirring at room temperature for 2 hours more. The residue prepared by concentration of the reaction solution in vacuo was purified by silica gel column chromatography and the resulting oily product was dissolved in 5 mL of ethyl acetate. Into the resulting ethyl acetate solution was dropped 1 equivalent of a hydrochloric acid/ethyl acetate solution and the mixture was concentrated to give 218 mg of the objective compound.

Colorless powder, MS spectrum: 278[M+H]$^+$

Example 48

4-(4-Isopropylphenyloxy)-6-methyl-4,5,6,7-tetrahydrofuro[2,3-c]pyridine hydrochloride

The same method as in Example 47 was conducted using 4-isopropylphenol instead of 4-chloro-3-methylphenol to give the objective compound.

Colorless powder, MS spectrum: 272[M+H]$^+$

Example 49

2-Bromo-4-(3,4-dichlorophenyloxy)-6-methyl-4,5,6,7-tetrahydrothieno[2,3-c]pyridine hydrochloride

The same method as in Example 3 was conducted using 2-bromo-6-methyl-4,5,6,7-tetrahydrothieno[2,3-c]pyridin-4-ol (Reference Example 12) instead of 6-methyl-4,5,6,7-tetrahydrofuro[2,3-c]pyridin-4-ol (Reference Example 1) and was conducted using 3,4-dichloro-1-fluorobenzene instead of 1,3-difluorobenzene to give the objective compound.

Colorless powder, MS spectrum: 392[M+H]$^+$

Example 50

7-(3,4-Dichlorophenyloxy)-5-methyl-4,5,6,7-tetrahydrofuro[3,2-c]pyridine hydrochloride

The same method as in Example 3 was conducted using 5-methyl-4,5,6,7-tetrahydrofuro[3,2-c]pyridin-7-ol (Reference Example 3) instead of 6-methyl-4,5,6,7-tetrahydrothieno[2,3-c]pyridin-4-ol (Reference Example 6) and was conducted using 3,4-dichloro-1-fluorobenzene instead of 1,3-difluorobenzene to give the objective compound.

Colorless powder, MS spectrum: 298[M+H]$^+$

Example 51

7-(4-Bromonaphthalen-1-yloxy)-5-methyl-4,5,6,7-tetrahydrofuro[3,2-c]pyridine hydrochloride

The same method as in Example 3 was conducted using 5-methyl-4,5,6,7-tetrahydrofuro[3,2-c]pyridin-7-ol (Reference Example 3) instead of 6-methyl-4,5,6,7-tetrahydrothieno[2,3-c]pyridin-4-ol (Reference Example 6) and was conducted using 1-bromo-4-fluoronaphthalene instead of 1,3-difluorobenzene to give the objective compound.

Colorless powder, MS spectrum: 360[M+H]$^+$

Example 52

4-(2,3-Dichlorophenyloxy)-2-methyl-4,5,6,7-tetrahydrothieno[2,3-c]pyridine hydrochloride

The same method as in Example 3 was conducted using 2-methyl-4,5,6,7-tetrahydrothieno[2,3-c]pyridin-4-ol (Reference Example 8) instead of 6-methyl-4,5,6,7-tetrahydrothieno[2,3-c]pyridin-4-ol (Reference Example 6) and was conducted using 2,3-dichloro-1-fluorobenzene instead of 1,3-difluorobenzene to give the objective compound.

Colorless powder, MS spectrum: 314[M+H]$^+$

Example 53

2-Methyl-4-(naphthalen-1-yloxy)-4,5,6,7-tetrahydrothieno[2,3-c]pyridine hydrochloride

The same method as in Example 3 was conducted using 2-methyl-4,5,6,7-tetrahydrothieno[2,3-c]pyridin-4-ol (Reference Example 8) instead of 6-methyl-4,5,6,7-tetrahydrothieno[2,3-c]pyridin-4-ol (Reference Example 6) and was conducted using 1-fluoronaphthalene instead of 1,3-difluorobenzene to give the objective compound.

Pale yellow powder, MS spectrum: 296[M+H]$^+$

Example 54

4-(4-Bromonaphthalen-1-yloxy)-2-methyl-4,5,6,7-tetrahydrothieno[2,3-c]pyridine hydrochloride

The same method as in Example 3 was conducted using 2-methyl-4,5,6,7-tetrahydrothieno[2,3-c]pyridin-4-ol (Reference Example 8) instead of 6-methyl-4,5,6,7-tetrahydrothieno[2,3-c]pyridin-4-ol (Reference Example 6) and was conducted using 1-bromo-4-fluoronaphthalene instead of 1,3-difluorobenzene to give the objective compound.

Pale yellow powder, MS spectrum: 374[M+H]$^+$

Example 55

4-(2,3-Dichlorophenyloxy)-2,6-dimethyl-4,5,6,7-tetrahydrothieno[2,3-c]pyridine hydrochloride

The same method as in Example 3 was conducted using 2,6-dimethyl-4,5,6,7-tetrahydrothieno[2,3-c]pyridin-4-ol (Reference Example 9) instead of 6-methyl-4,5,6,7-tetrahydrothieno[2,3-c]pyridin-4-ol (Reference Example 6) and was

Example 56

4-(3,4-Dimethoxyphenyloxy)-6-methyl-4,5,6,7-tetrahydrofuro[2,3-c]pyridine hydrochloride The same method as in Example 47 was conducted using 4-chloro-3-methylphenol, instead of 3,4-dimethoxyphenol to give the objective compound.
Yellow powder, MS spectrum: 290[M+H]$^+$

Example 57

4-(3,4-Dichlorophenyloxy)-2,6-dimethyl-4,5,6,7-tetrahydrofuro[2,3-c]pyridine hydrochloride The same method as in Example 3 was conducted using 2,6-dimethyl-4,5,6,7-tetrahydrofuro[2,3-c]pyridin-4-ol (Reference Example 2) instead of 6-methyl-4,5,6,7-tetrahydrothieno[2,3-c]pyridin-4-ol (Reference Example 6) and was conducted using 3,4-dichloro-1-fluorobenzene instead of 1,3-difluorobenzene to give the objective compound.
Colorless powder, MS spectrum: 312[M+H]$^+$

Example 58

4-(4-Bromonaphthalen-1-yloxy)-2,6-dimethyl-4,5,6,7-tetrahydrofuro[2,3-c]pyridine hydrochloride The same method as in Example 3 was conducted using 2,6-dimethyl-4,5,6,7-tetrahydrofuro[2,3-c]pyridin-4-ol (Reference Example 2) instead of 6-methyl-4,5,6,7-tetrahydrothieno[2,3-c]pyridin-4-ol (Reference Example 6) and was conducted using 1-bromo-4-fluoronaphthalene instead of 1,3-difluorobenzene to give the objective compound.
Colorless powder, MS spectrum: 372[M+H]$^+$

Example 59

4-[4-Chloro-3-(trifluoromethyl)phenyloxy]-6-methyl-4,5,6,7-tetrahydrofuro[2,3-c]pyridine hydrochloride The same method as in Example 47 was conducted using 4-chloro-3-(trifluoromethyl)phenol instead of 4-chloro-3-methylphenol to give the objective compound.
Colorless powder, MS spectrum: 332[M+H]$^+$

Example 60

4-(3-Bromophenyloxy)-6-methyl-4,5,6,7-tetrahydrofuro[2,3-c]pyridine hydrochloride The same method as in Example 47 was conducted using 3-bromophenol instead of 4-chloro-3-methylphenol to give the objective compound.
Colorless powder, MS spectrum: 308[M+H]$^+$

Example 61

2,6-Dimethyl-4-(naphthalen-1-yloxy)-4,5,6,7-tetrahydrothieno[2,3-c]pyridine hydrochloride The same method as in Example 3 was conducted using 2,6-dimethyl-4,5,6,7-tetrahydrothieno[2,3-c]pyridin-4-ol (Reference Example 9) instead of 6-methyl-4,5,6,7-tetrahydrothieno[2,3-c]pyridin-4-ol (Reference Example 6) and was conducted using 1-fluoronaphthalene instead of 1,3-difluorobenzene to give the objective compound.
Pale yellow powder, MS spectrum: 310[M+H]$^+$

Example 62

4-(4-Bromonaphthalen-1-yloxy)-2,6-dimethyl-4,5,6,7-tetrahydrothieno[2,3-c]pyridine hydrochloride The same method as in Example 3 was conducted using 2,6-dimethyl-4,5,6,7-tetrahydrothieno[2,3-c]pyridin-4-ol (Reference Example 9) instead of 6-methyl-4,5,6,7-tetrahydrothieno[2,3-c]pyridin-4-ol (Reference Example 6) and was conducted using 1-bromo-4-fluoronaphthalene instead of 1,3-difluorobenzene to give the objective compound.
Pale yellow powder, MS spectrum: 388[M+H]$^+$

Example 63

2-Bromo-6-methyl-4-(naphthalen-1-yloxy)-4,5,6,7-tetrahydrothieno[2,3-c]pyridine hydrochloride The same method as in Example 47 was conducted using 2-bromo-6-methyl-4,5,6,7-tetrahydrothieno[2,3-c]pyridin-4-ol (Reference Example 12) instead of 6-methyl-4,5,6,7-tetrahydrofuro[2,3-c]pyridin-4-ol (Reference Example 1) and was conducted using 1-naphthol instead of 4-chloro-3-methylphenol to give the objective compound.
Colorless powder, MS spectrum: 374[M+H]$^+$

Example 64

4-(4-Bromonaphthalen-1-yloxy)-4,5,6,7-tetrahydrothieno[2,3-c]pyridine hydrochloride The same method as in Example 3 was conducted using 4,5,6,7-tetrahydrothieno[2,3-c]pyridin-4-ol (Reference Example 5) instead of 6-methyl-4,5,6,7-tetrahydrothieno[2,3-c]pyridin-4-ol (Reference Example 6) and was conducted using 1-bromo-4-fluoronaphthalene instead of 1,3-difluorobenzene to give the objective compound.
Colorless powder, MS spectrum: 360[M+H]$^+$

Example 65

2-Bromo-7-(3,4-dichlorophenyloxy)-5-methyl-4,5,6,7-tetrahydrothieno[3,2-c]pyridine hydrochloride The same method as in Example 47 was conducted using 2-bromo-5-methyl-4,5,6,7-tetrahydrothieno[3,2-c]pyridin-7-ol (Reference Example 18) instead of 6-methyl-4,5,6,7-tetrahydrofuro[2,3-c]pyridin-4-ol (Reference Example 1) and was conducted using 3,4-dichlorophenol instead of 4-chloro-3-methylphenol to give the objective compound.
Colorless powder, MS spectrum: 392[M+H]$^+$

Example 66

4-(4-Bromo-3-chlorophenyloxy)-6-methyl-4,5,6,7-tetrahydrofuro[2,3-c]pyridine hydrochloride The same method as in Example 3 was conducted using 6-methyl-4,5,6,7-tetrahydrofuro[2,3-c]pyridin-4-ol (Reference Example 1) instead of 6-methyl-4,5,6,7-tetrahydrothieno[2,3-c]pyridin-4-ol (Reference Example 6) and was

--- conducted using 2,3-dichloro-1-fluorobenzene instead of 1,3-difluorobenzene to give the objective compound.
Colorless powder, MS spectrum: 328[M+H]$^+$ conducted using 4-bromo-3-chloro-1-fluorobenzene instead of 1,3-difluorobenzene to give the objective compound.
Pale yellow powder, MS spectrum: 344[M+H]$^+$

Example 67

4-(4-Chloro-3,5-dimethylphenyloxy)-6-methyl-4,5,6,7-tetrahydrofuro[2,3-c]pyridine hydrochloride The same method as in Example 3 was conducted using 6-methyl-4,5,6,7-tetrahydrofuro[2,3-c]pyridin-4-ol (Reference Example 1) instead of 6-methyl-4,5,6,7-tetrahydrothieno[2,3-c]pyridin-4-ol (Reference Example 6) and was conducted using 4-chloro-1-fluoro-3,5-dimethylbenzene instead of 1,3-difluorobenzene to give the objective compound.
Colorless powder, MS spectrum: 292[M+H]$^+$

Example 68

4-(3,4-Difluorophenyloxy)-6-methyl-4,5,6,7-tetrahydrofuro[2,3-c]pyridine hydrochloride The same method as in Example 3 was conducted using 6-methyl-4,5,6,7-tetrahydrofuro[2,3-c]pyridin-4-ol (Reference Example 1) instead of 6-methyl-4,5,6,7-tetrahydrothieno[2,3-c]pyridin-4-ol (Reference Example 6) and was conducted using 1,3,4-trifluorobenzene instead of 1,3-difluorobenzene to give the objective compound.
Colorless powder, MS spectrum: 266[M+H]$^+$

Example 69

4-(4-Bromo-3,5-dimethylphenyloxy)-6-methyl-4,5,6,7-tetrahydrofuro[2,3-c]pyridine hydrochloride The same method as in Example 3 was conducted using 6-methyl-4,5,6,7-tetrahydrofuro[2,3-c]pyridin-4-ol (Reference Example 1) instead of 6-methyl-4,5,6,7-tetrahydrothieno[2,3-c]pyridin-4-ol (Reference Example 6) and was conducted using 4-bromo-1-fluoro-3,5-dimethylbenzene instead of 1,3-difluorobenzene to give the objective compound.
Colorless powder, MS spectrum: 337[M+H]$^+$

Example 70

4-(4-Chlorophenyloxy)-6-methyl-4,5,6,7-tetrahydrofuro[2,3-c]pyridine hydrochloride The same method as in Example 47 was conducted using 4-chloro-phenol instead of 4-chloro-3-methylphenol to give the objective compound.
Pale yellow powder, MS spectrum: 264[M+H]$^+$

Example 71

2-Bromo-5-methyl-7-(naphthalen-1-yloxy)-4,5,6,7-tetrahydrothieno[3,2-c]pyridine hydrochloride The same method as in Example 47 was conducted using 2-bromo-5-methyl-4,5,6,7-tetrahydrothieno[3,2-c]pyridin-7-ol (Reference Example 18) instead of 6-methyl-4,5,6,7-tetrahydrofuro[2,3-c]pyridin-4-ol (Reference Example 1) and was conducted using 1-naphthol instead of 4-chloro-3-methylphenol to give the objective compound.
Colorless powder, MS spectrum: 374[M+H]$^+$

Example 72

4-(3,4-Dichlorophenyloxy)-6-methyl-2-phenyl-4,5,6,7-tetrahydrothieno[2,3-c]pyridine hydrochloride In an argon atmosphere, a mixed solution of 36 mg of 2-bromo-4-(3,4-dichlorophenyloxy)-6-methyl-4,5,6,7-tetrahydro-thieno[2,3-c]pyridine hydrochloride (Example 49), 22 mg of phenylboronic acid, 5 mg of a tetrakis (triphenyl phosphine) palladium catalyst and 19 mg of potassium carbonate in 1 mL of toluene was prepared, tightly closed and stirred at 90° C. overnight. After the reaction solution was cooled, 5 mL of water was added thereto and the mixture was subjected to extraction with ethyl acetate. The organic layer was washed with water and a saturated solution of sodium chloride successively and dried over anhydrous magnesium sulfate and the solvent was evaporated therefrom in vacuo. The residue was purified by silica gel column chromatography and the resulting oily product was dissolved in 2 mL of ethyl acetate. Into the resulting ethyl acetate solution was dropped 1 equivalent of a hydrochloric acid/ethyl acetate solution and the mixture was concentrated to give 20 mg of the objective compound.
Colorless powder, MS spectrum: 390[M+H]$^+$

Example 73

2-Chloro-4-(3,4-dichlorophenyloxy)-6-methyl-4,5,6,7-tetrahydrothieno[2,3-c]pyridine hydrochloride The same method as in Example 47 was conducted using 2-chloro-6-methyl-4,5,6,7-tetrahydrothieno[2,3-c]pyridin-4-ol (Reference Example 11) instead of 6-methyl-4,5,6,7-tetrahydrofuro[2,3-c]pyridin-4-ol (Reference Example 1) and was conducted using 3,4-dichlorophenol instead of 4-chloro-3-methylphenol to give the objective compound.
Colorless powder, MS spectrum: 348[M+H]$^+$

Example 74

2-Cyano-4-(3,4-dichlorophenyloxy)-6-methyl-4,5,6,7-tetrahydrothieno[2,3-c]pyridine hydrochloride In an argon atmosphere, a mixed solution of 57 mg of 2-bromo-4-(3,4-dichlorophenyloxy)-6-methyl-4,5,6,7-tetrahydro-thieno[2,3-c]pyridine hydrochloride (Example 49), 28 mg of zinc cyanide and 25 mg of a tetrakis(triphenyl phosphine) palladium catalyst in 2 mL of DMF was prepared, tightly closed and stirred at 150° C. overnight. After the reaction solution was cooled, 5 mL of a 25% aqueous ammonia was added thereto and the mixture was subjected to extraction with ethyl acetate. The organic layer was washed with water and a saturated solution of sodium chloride successively and dried over anhydrous magnesium sulfate and the solvent was evaporated therefrom in vacuo. The residue was purified by silica gel column chromatography and the resulting oily product was dissolved in 2 mL of ethyl acetate. Into the resulting ethyl acetate solution was dropped 1 equivalent of a hydrochloric acid/ethyl acetate solution and the mixture was concentrated to give 9 mg of the objective compound.
Yellow liquid, MS spectrum: 339[M+H]$^+$

Example 75

4-(3,4-Dibromophenyloxy)-6-methyl-4,5,6,7-tetrahydrofuro[2,3-c]pyridine hydrochloride The same method as in Example 3 was conducted using 6-methyl-4,5,6,7-tetrahydrofuro[2,3-c]pyridin-4-ol (Reference Example 1) instead of 6-methyl-4,5,6,7-tetrahydrothieno[2,3-c]pyridin-4-ol (Reference Example 6) and was conducted using 3,4-dibromo-1-fluorobenzene instead of 1,3-difluorobenzene to give the objective compound.
Colorless powder, MS spectrum: 386[M+H]$^+$

Example 76

4-(2,4-Dichlorophenyloxy)-6-methyl-4,5,6,7-tetrahydrofuro[2,3-c]pyridine hydrochloride The same method as in Example 47 was conducted using 2,4-dichlorophenol instead of 4-chloro-3-methylphenol to give the objective compound.
Pale yellow powder, MS spectrum: 298[M+H]$^+$

Example 77

4-(4-Chloro-3,5-dimethylphenyloxy)-2,6-dimethyl-4,5,6,7-tetrahydrofuro[2,3-c]pyridine hydrochloride The same method as in Example 47 was conducted using 2,6-dimethyl-4,5,6,7-tetrahydrofuro[2,3-c]pyridin-4-ol (Reference Example 2) instead of 6-methyl-4,5,6,7-tetrahydrofuro[2,3-c]pyridin-4-ol (Reference Example 1) and was conducted using 4-chloro-3,5-dimethylphenol instead of 4-chloro-3-methylphenol to give the objective compound.
Colorless powder, MS spectrum: 306[M+H]$^+$

Example 78

4-(4-Bromo-3-chlorophenyloxy)-2,6-dimethyl-4,5,6,7-tetrahydrofuro[2,3-c]pyridine hydrochloride The same method as in Example 47 was conducted using 2,6-dimethyl-4,5,6,7-tetrahydrofuro[2,3-c]pyridin-4-ol (Reference Example 2) instead of 6-methyl-4,5,6,7-tetrahydrofuro[2,3-c]pyridin-4-ol (Reference Example 1) and was conducted using 4-bromo-3-chlorophenol instead of 4-chloro-3-methylphenol to give the objective compound.
Colorless powder, MS spectrum: 356[M+H]$^+$

Example 79

4-(3,4-Dichlorophenyloxy)-2-methyl-4,5,6,7-tetrahydrothieno[2,3-c]pyridine hydrochloride The same method as in Example 3 was conducted using 2-methyl-4,5,6,7-tetrahydrothieno[2,3-c]pyridin-4-ol (Reference Example 8) instead of 6-methyl-4,5,6,7-tetrahydrothieno[2,3-c]pyridin-4-ol (Reference Example 6) and was conducted using 3,4-dichloro-1-fluorobenzene instead of 1,3-difluorobenzene to give the objective compound.
Colorless powder, MS spectrum: 314[M+H]$^+$

Example 80

4-(3,4-Dichlorophenyloxy)-2,6-dimethyl-4,5,6,7-tetrahydrothieno[2,3-c]pyridine hydrochloride The same method as in Example 3 was conducted using 2,6-dimethyl-4,5,6,7-tetrahydrothieno[2,3-c]pyridin-4-ol (Reference Example 9) instead of 6-methyl-4,5,6,7-tetrahydrothieno[2,3-c]pyridin-4-ol (Reference Example 6) and was conducted using 3,4-dichloro-1-fluorobenzene instead of 1,3-difluorobenzene to give the objective compound.
Colorless powder, MS spectrum: 328[M+H]$^+$

Example 81

4-(4-Bromo-3-methylphenyloxy)-6-methyl-4,5,6,7-tetrahydrofuro[2,3-c]pyridine hydrochloride The same method as in Example 3 was conducted using 6-methyl-4,5,6,7-tetrahydrofuro[2,3-c]pyridin-4-ol (Reference Example 1) instead of 6-methyl-4,5,6,7-tetrahydrothieno[2,3-c]pyridin-4-ol (Reference Example 6) and was conducted using 4-bromo-3-methyl-1-fluorobenzene instead of 1,3-difluorobenzene to give the objective compound.
Colorless powder, MS spectrum: 322[M+H]$^+$

Example 82

4-(4-Bromo-3,5-dimethylphenyloxy)-2,6-dimethyl-4,5,6,7-tetrahydrofuro[2,3-c]pyridine hydrochloride The same method as in Example 47 was conducted using 2,6-dimethyl-4,5,6,7-tetrahydrofuro[2,3-c]pyridin-4-ol (Reference Example 2) instead of 6-methyl-4,5,6,7-tetrahydrofuro[2,3-c]pyridin-4-ol (Reference Example 1) and was conducted using 4-bromo-3,5-dimethylphenol instead of 4-chloro-3-methylphenol to give the objective compound.
Colorless powder, MS spectrum: 350[M+H]$^+$

Example 83

4-(4-Chloro-3-ethylphenyloxy)-2,6-dimethyl-4,5,6,7-tetrahydrofuro[2,3-c]pyridine hydrochloride The same method as in Example 47 was conducted using 2,6-dimethyl-4,5,6,7-tetrahydrofuro[2,3-c]pyridin-4-ol (Reference Example 2) instead of 6-methyl-4,5,6,7-tetrahydrofuro[2,3-c]pyridin-4-ol (Reference Example 1) and was conducted using 4-chloro-3-ethylphenol instead of 4-chloro-3-methylphenol to give the objective compound.
Colorless powder, MS spectrum: 306[M+H]$^+$

Example 84

4-(4-Chloronaphthalene-1-yloxy)-2,6-dimethyl-4,5,6,7-tetrahydrofuro[2,3-c]pyridine hydrochloride The same method as in Example 47 was conducted using 2,6-dimethyl-4,5,6,7-tetrahydrofuro[2,3-c]pyridin-4-ol (Reference Example 2) instead of 6-methyl-4,5,6,7-tetrahydrofuro[2,3-c]pyridin-4-ol (Reference Example 1) and was conducted using 4-chloro-1-naphthol instead of 4-chloro-3-methylphenol to give the objective compound.
Colorless powder, MS spectrum: 328[M+H]$^+$

Example 85

4-(4-Chlorophenyloxy)-2,6-dimethyl-4,5,6,7-tetrahydrofuro[2,3-c]pyridine hydrochloride The same method as in Example 47 was conducted using 2,6-dimethyl-4,5,6,7-tetrahydrofuro[2,3-c]pyridin-4-ol (Reference Example 2) instead of 6-methyl-4,5,6,7-tetrahydrofuro[2,3-c]pyridin-4-ol (Reference Example 1) and was conducted using 1-chlorophenol instead of 4-chloro-3-methylphenol to give the objective compound.
Colorless powder, MS spectrum: 378[M+H]$^+$

Example 86

4-(4-Chloro-3-ethylphenyloxy)-6-methyl-4,5,6,7-tetrahydrofuro[2,3-c]pyridine hydrochloride The same method as in Example 47 was conducted using 4-chloro-3-ethylphenol w instead of 4-chloro-3-methylphenol to give the objective compound.
Colorless powder, MS spectrum: 292[M+H]$^+$

Example 87

6-Methyl-4-(quinolin-4-yloxy)-4,5,6,7-tetrahydrofuro[2,3-c]pyridine

The same method as in Example 38 was conducted using 4-hydroxyquinoline instead of 8-hydroxyquinoline to give the objective compound.
Yellow powder, MS spectrum: 281[M+H]$^+$

Example 88

7-Methyl-4-(naphthalen-1-yloxy)-5,6,7,8-tetrahydro-4H-thieno[2,3-c]azepine hydrochloride The same method as in Example 3 was conducted using 7-methyl-5,6,7,8-tetrahydro-4H-thieno[2,3-c]azepin-4-ol (Reference Example 22) instead of 6-methyl-5,6,7,8-tetrahydrothieno[2,3-c]pyridin-4-ol (Reference Example 6) and was conducted using 1-fluoronaphthalene instead of 1,3-difluorobenzene to give the objective compound.
Pale thirst-colored powder, MS spectrum: 310[M+H]$^+$

Example 89

4-(3-Chlorophenyloxy)-6-methyl-4,5,6,7-tetrahydrofuro[2,3-c]pyridine hydrochloride The same method as in Example 47 was conducted using 3-chlorophenol instead of 4-chloro-3-methylphenol to give the objective compound.
Pale yellow powder, MS spectrum: 264[M+H]$^+$

Example 90

4-(Isoquinoline-5-yloxy)-6-methyl-4,5,6,7-tetrahydrofuro[2,3-c]pyridine hydrochloride The same method as in Example 47 was conducted using 5-hydroxyisoquinoline instead of 4-chloro-3-methylphenol to give the objective compound.
Pale yellow powder, MS spectrum: 281[M+H]$^+$

Example 91

4-(3,4-Dimethylphenyloxy)-6-methyl-4,5,6,7-tetrahydrofuro[2,3-c]pyridine hydrochloride The same method as in Example 47 was conducted using 3,4-dimethylphenol instead of 4-chloro-3-methylphenol to give the objective compound.
Colorless powder, MS spectrum: 258[M+H]$^+$

Example 92

4-(2-Methylpyridyl-5-yloxy)-6-methyl-4,5,6,7-tetrahydrofuro[2,3-c]pyridine dihydrochloride The same method as in Example 47 was conducted using 5-hydroxy-2-methylpyridine instead of 4-chloro-3-methylphenol to give the objective compound.
Pale yellow powder, MS spectrum: 245[M+H]$^+$

Example 93

4-(Indan-5-yloxy)-6-methyl-4,5,6,7-tetrahydrofuro[2,3-c]pyridine hydrochloride

The same method as in Example 47 was conducted using 5-hydroxyindan instead of 4-chloro-3-methylphenol to give the objective compound.
Colorless powder, MS spectrum: 270[M+H]$^+$

Example 94

4-(3,4-Methylenedioxyphenyloxy)-6-methyl-4,5,6,7-tetrahydrofuro[2,3-c]pyridine hydrochloride The same method as in Example 47 was conducted using 3,4-methylenedioxyphenol instead of 4-chloro-3-methylphenol to give the objective compound.
Pale yellow powder, MS spectrum: 274[M+H]$^+$

Example 95

4-(3,5-Dimethylphenyloxy)-6-methyl-4,5,6,7-tetrahydrofuro[2,3-c]pyridine hydrochloride The same method as in Example 47 was conducted using 3,5-dimethylphenol instead of 4-chloro-3-methylphenol to give the objective compound.
Colorless powder, MS spectrum: 258[M+H])

Example 96

6-Methyl-4-(4-phenylphenoxy)-4,5,6,7-tetrahydrofuro[2,3-c]pyridine hydrochloride The same method as in Example 47 was conducted using 4-hydroxybiphenyl instead of 4-chloro-3-methylphenol to give the objective compound.
Colorless powder, MS spectrum: 306[M+H]$^+$

Example 97

4-(4-Chloronaphthalen-1-yloxy)-6-methyl-4,5,6,7-tetrahydrofuro[2,3-c]pyridine hydrochloride The same method as in Example 47 was conducted using 4-chloro-1-naphthol instead of 4-chloro-3-methylphenol to give the objective compound.
Colorless powder, MS spectrum: 314[M+H]$^+$

Example 98

4-(3,4-Dibromophenyloxy)-2,6-dimethyl-4,5,6,7-tetrahydrothieno[2,3-c]pyridine hydrochloride The same method as in Example 3 was conducted using 2,6-dimethyl-4,5,6,7-tetrahydrothieno[2,3-c]pyridin-4-ol (Reference Example 9) instead of 6-methyl-4,5,6,7-tetrahydrothieno[2,3-c]pyridin-4-ol (Reference Example 6) and was conducted using 3,4-dibromo-1-fluorobenzene instead of 1,3-difluorobenzene to give the objective compound.
Colorless powder, MS spectrum: 416[M+H]$^+$ Example 99

4-(3,4-Dichlorophenyloxy)-7-methyl-5,6,7,8-tetrahydro-4H-thieno[2,3-c]azepine hydrochloride The same method as in Example 3 was conducted using 7-methyl-5,6,7,8-tetrahydro-4H-thieno[2,3-c]azepin-4-ol (Reference Example 22) instead of 6-methyl-5,6,7,8-tetrahydrothieno[2,3-c]pyridin-4-ol (Reference Example 6) and was conducted using 3,4-dichloro-1-fluorobenzene instead of 1,3-difluorobenzene to give the objective compound.
Pink powder, MS spectrum: 328[M+H]$^+$ Example 100

4-(3,4-Dichlorophenyloxy)-2,7-dimethyl-5,6,7,8-tetrahydro-4H-thieno[2,3-c]azepine hydrochloride The same method as in Example 3 was conducted using 2,7-dimethyl-5,6,7,8-tetrahydro-4H-thieno[2,3-c]azepin-4-ol (Reference Example 23) instead of 6-methyl-4,5,6,7-tetrahydrothieno[2,3-c]pyridin-4-ol (Reference Example 6) and was conducted using 3,4-dichlorofluorobenzene instead of 1,3-difluorobenzene to give the objective compound.
Pink powder, MS spectrum: 342[M+H]$^+$ Example 101

6-Methyl-4-(3,4,5-trimethylphenyloxy)-4,5,6,7-tetrahydrofuro[2,3-c]pyridine hydrochloride The same method as in Example 47 was conducted using 3,4,5-trimethylphenol instead of 4-chloro-3-methylphenol to give the objective compound.
Colorless powder, MS spectrum: 272[M+H]$^+$ Example 102

2,7-Dimethyl-4-(naphthalen-1-yloxy)-5,6,7,8-tetrahydro-4H-thieno[2,3-c]azepine hydrochloride The same method as in Example 3 was conducted using 2,7-dimethyl-5,6,7,8-tetrahydro-4H-thieno[2,3-c]azepin-4-ol (Reference Example 23) instead of 6-methyl-4,5,6,7-tetrahydrothieno[2,3-c]pyridin-4-ol (Reference Example 6) and was conducted using 1-fluoronaphthalene instead of 1,3-difluorobenzene to give the objective compound.
Pink powder, MS spectrum: 324[M+H]$^+$ Example 103

4-(3,4-Dichlorophenyloxy)-6-ethyl-2-methyl-4,5,6,7-tetrahydrothieno[2,3-c]pyridine hydrochloride The same method as in Example 3 was conducted using 6-ethyl-2-methyl-4,5,6,7-tetrahydrothieno[2,3-c]pyridin-4-ol (Reference Example 10) instead of 6-methyl-4,5,6,7-tetrahydrothieno[2,3-c]pyridin-4-ol (Reference Example 6) and was conducted using 3,4-dichloro-1-fluorobenzene instead of 1,3-difluorobenzene to give the objective compound.
Colorless powder, MS spectrum: 342[M+H]$^+$ Example 104

6-Ethyl-2-methyl-4-(naphthalen-1-yloxy)-4,5,6,7-tetrahydrothieno[2,3-c]pyridine hydrochloride The same method as in Example 3 was conducted using 6-ethyl-2-methyl-4,5,6,7-tetrahydrothieno[2,3-c]pyridin-4-ol (Reference Example 10) instead of 6-methyl-4,5,6,7-tetrahydrothieno[2,3-c]pyridin-4-ol (Reference Example 6) and was conducted using 1-fluoronaphthalene instead of 1,3-difluorobenzene to give the objective compound.
Colorless powder, MS spectrum: 324[M+H]$^+$ Example 105

4-(2,3-Dichlorophenyloxy)-6-ethyl-2-methyl-4,5,6,7-tetrahydrothieno[2,3-c]pyridine hydrochloride The same method as in Example 3 was conducted using 6-ethyl-2-methyl-4,5,6,7-tetrahydrothieno[2,3-c]pyridin-4-ol (Reference Example 10) instead of 6-methyl-4,5,6,7-tetrahydrothieno[2,3-c]pyridin-4-ol (Reference Example 6) and was conducted using 2,3-dichloro-1-fluorobenzene instead of 1,3-difluorobenzene to give the objective compound.
Colorless powder, MS spectrum: 342[M+H]$^+$ Example 106

5-Methyl-8-(3,4,5-trimethylphenyloxy)-5,6,7,8-tetrahydro-4H-thieno[3,2-c]azepine hydrochloride The same method as in Example 47 was conducted using 5-methyl-5,6,7,8-tetrahydro-4H-thieno[3,2-c]azepin-8-ol (Reference Example 25) instead of 6-methyl-4,5,6,7-tetrahydrofuro[2,3-c]pyridin-4-ol (Reference Example 1) and was conducted using 3,4,5-trimethylphenol instead of 4-chloro-3-methylphenol to give the objective compound.
Brown liquid, MS spectrum: 302[M+H]$^+$ Example 107

4-(3,4-Dichlorophenyloxy)-2,7-dimethyl-5,6,7,8-tetrahydro-4H-furo[2,3-c]azepine hydrochloride The same method as in Example 3 was conducted using 2,7-dimethyl-5,6,7,8-tetrahydro-4H-furo[2,3-c]azepin-4-ol (Reference Example 20) instead of 6-methyl-4,5,6,7-tetrahydrothieno[2,3-c]pyridin-4-ol (Reference Example 6) and was conducted using 3,4-dichloro-1-fluorobenzene instead of 1,3-difluorobenzene to give the objective compound.
Yellow liquid, MS spectrum: 326[M+H]$^+$ Example 108

8-(3,4-Dichlorophenyloxy)-5-methyl-5,6,7,8-tetrahydro-4H-thieno[3,2-c]azepine hydrochloride The same method as in Example 47 was conducted using 5-methyl-5,6,7,8-tetrahydro-4H-thieno[3,2-c]azepin-8-ol (Reference Example 25) instead of 6-methyl-4,5,6,7-tetrahydrofuro[2,3-c]pyridin-4-ol (Reference Example 1) and was conducted using 3,4-dichlorophenol instead of 4-chloro-3-methylphenol to give the objective compound.
Ecru liquid, MS spectrum: 328[M+H]$^+$

Example 109

6-Methyl-4-(naphthalen-1-yloxy)-5,6,7,8-tetrahydro-4H-thieno[2,3-d]azepine hydrochloride The same method as in Example 3 was conducted using 6-methyl-5,6,7,8-tetrahydro-4H-thieno[2,3-d]azepin-4-ol (Reference Example 28) instead of 6-methyl-4,5,6,7-tetrahydrothieno[2,3-c]pyridin-4-ol (Reference Example 6) and was conducted using 1-fluoronaphthalene instead of 1,3-difluorobenzene to give the objective compound.

Ecru liquid, MS spectrum: 310[M+H]$^+$

Example 110

2-Chloro-4-(3,4-dichlorophenyloxy)-7-methyl-5,6,7,8-tetrahydro-4H-thieno[2,3-c]azepine hydrochloride The same method as in Example 3 was conducted using 2-chloro-7-methyl-5,6,7,8-tetrahydro-4H-thieno[2,3-c]azepin-4-ol (Reference Example 24) instead of 6-methyl-4,5,6,7-tetrahydrothieno[2,3-c]pyridin-4-ol (Reference Example 6) and was conducted using 3,4-dichloro-1-fluorobenzene instead of 1,3-difluorobenzene to give the objective compound.

Pink powder, MS spectrum: 362[M+H]$^+$

Example 111

4-(3,4-Dichlorophenyloxy)-6-methyl-5,6,7,8-tetrahydro-4H-thieno[2,3-d]azepine hydrochloride The same method as in Example 3 was conducted using 6-methyl-5,6,7,8-tetrahydro-4H-thieno[2,3-d]azepin-4-ol (Reference Example 28) instead of 6-methyl-4,5,6,7-tetrahydrothieno[2,3-c]pyridin-4-ol (Reference Example 6) and was conducted using 3,4-dichloro-1-fluorobenzene instead of 1,3-difluorobenzene to give the objective compound.

Ecru liquid, MS spectrum: 328[M+H]$^+$

Example 112

8-(3,4-Dibromophenyloxy)-5-methyl-5,6,7,8-tetrahydro-4H-thieno[3,2-c]azepine hydrochloride The same method as in Example 3 was conducted using 5-methyl-5,6,7,8-tetrahydro-4H-thieno[3,2-c]azepin-8-ol (Reference Example 25) instead of 6-methyl-4,5,6,7-tetrahydrothieno[2,3-c]pyridin-4-ol (Reference Example 6) and was conducted using 3,4-dibromo-1-fluorobenzene instead of 1,3-difluorobenzene to give the objective compound.

Ecru liquid, MS spectrum: 416[M+H]$^+$

Example 113

8-(4-Chloro-3,5-dimethylphenyloxy)-5-methyl-5,6,7,8-tetrahydro-4H-thieno[3,2-c]azepine hydrochloride The same method as in Example 47 was conducted using 5-methyl-5,6,7,8-tetrahydro-4H-thieno[3,2-c]azepin-8-ol (Reference Example 25) instead of 6-methyl-4,5,6,7-tetrahydrofuro[2,3-c]pyridin-4-ol (Reference Example 1) and was conducted using 4-chloro-3,5-dimethylphenol instead of 4-chloro-3-methylphenol to give the objective compound.

Ecru liquid, MS spectrum: 322[M+H]$^+$

Example 114

8-(4-Bromo-3,5-dimethylphenyloxy)-5-methyl-5,6,7,8-tetrahydro-4H-thieno[3,2-c]azepine hydrochloride The same method as in Example 47 was conducted using 5-methyl-5,6,7,8-tetrahydro-4H-thieno[3,2-c]azepin-8-ol (Reference Example 25) instead of 6-methyl-4,5,6,7-tetrahydrofuro[2,3-c]pyridin-4-ol (Reference Example 1) and was conducted using 4-bromo-3,5-dimethylphenol instead of 4-chloro-3-methylphenol to give the objective compound.

Ecru liquid, MS spectrum: 466[M+H]$^+$

Example 115

8-(4-Chloronaphthalen-1-yloxy)-5-methyl-5,6,7,8-tetrahydro-4H-thieno[3,2-c]azepine hydrochloride The same method as in Example 47 was conducted using 5-methyl-5,6,7,8-tetrahydro-4H-thieno[3,2-c]azepin-8-ol (Reference Example 25) instead of 6-methyl-4,5,6,7-tetrahydrofuro[2,3-c]pyridin-4-ol (Reference Example 1) and was conducted using 4-chloro-1-naphthol instead of 4-chloro-3-methylphenol to give the objective compound.

Ecru liquid, MS spectrum: 344[M+H]$^+$

Example 116

4-(3,4-Dicyanophenyloxy)-2,6-dimethyl-4,5,6,7-tetrahydrofuro[2,3-c]pyridine hydrochloride The same method as in Example 3 was conducted using 2,6-dimethyl-4,5,6,7-tetrahydrofuro[2,3-c]pyridin-4-ol (Reference Example 2) instead of 6-methyl-4,5,6,7-tetrahydrofuro[2,3-c]pyridin-4-ol (Reference Example 1) and was conducted using 4-fluorophthalonitrile instead of 1,3-difluorobenzene to give the objective compound.

Colorless powder, MS spectrum: 294[M+H]$^+$

Example 117

4-(4-Carbamoylphenyloxy)-2,7-dimethyl-5,6,7,8-tetrahydro-4H-thieno[2,3-c]azepine The same method as in Example 1 was conducted using 2,7-dimethyl-5,6,7,8-tetrahydro-4H-thieno[2,3-c]azepin-4-ol (Reference Example 23) instead of 6-methyl-4,5,6,7-tetrahydrothieno[2,3-c]pyridin-4-ol (Reference Example 6) and was conducted using 4-fluorobenzamide instead of 1-fluoronaphthalene to give the objective compound.

Pale yellow powder, MS spectrum: 317[M+H]$^+$

Example 118

4-(3-Chloro-4-carbomethoxyphenyloxy)-6-methyl-4,5,6,7-tetrahydrofuro[2,3-c]pyridine hydrochloride The same method as in Example 3 was conducted using 6-methyl-4,5,6,7-tetrahydrofuro[2,3-c]pyridin-4-ol (Reference Example 1) instead of 6-methyl-4,5,6,7-tetrahydrothieno[2,3-c]pyridin-4-ol (Reference Example 6) and was conducted using methyl 2-chloro-4-fluorobenzoate instead of 1,3-difluorobenzene to give the objective compound.

Colorless powder, MS spectrum: 322[M+H]$^+$

Example 119

4-(3,4-Dichlorophenyloxy)-4,5,6,7-tetrahydrofuro[2,3-c]pyridine hydrochloride

The same method as in Example 3 was conducted using 4,5,6,7-tetrahydrofuro[2,3-c]pyridin-4-ol (Reference Example 4) instead of 6-methyl-4,5,6,7-tetrahydrothieno[2,3-c]pyridin-4-ol (Reference Example 6) and was conducted using 3,4-dichloro-1-fluorobenzene instead of 1,3-difluorobenzene to give the objective compound.
Pale yellow solid, MS spectrum: 284[M+H]$^+$

Example 120

4-(4-Bromonaphthalen-1-yloxy)-4,5,6,7-tetrahydrofuro[2,3-c]pyridine hydrochloride The same method as in Example 3 was conducted using 4,5,6,7-tetrahydrofuro[2,3-c]pyridin-4-ol (Reference Example 4) instead of 6-methyl-4,5,6,7-tetrahydrothieno[2,3-c]pyridin-4-ol (Reference Example 6) and was conducted using 1-bromo-4-fluoronaphthalene instead of 1,3-difluorobenzene to give the objective compound.
Pale yellow solid, MS spectrum: 344[M+H]$^+$

Example 121

4-(3,4-Dichlorophenyloxy)-6-methyl-5,6,7,8-tetrahydro-4H-thieno[2,3-d]azepine hydrochloride The same method as in Example 3 was conducted using 5,6,7,8-tetrahydro-4H-thieno[2,3-d]azepin-4-ol (Reference Example 29) instead of 6-methyl-4,5,6,7-tetrahydrothieno[2,3-c]pyridin-4-ol (Reference Example 6) and was conducted using 3,4-dichloro-1-fluorobenzene instead of 1,3-difluorobenzene to give the objective compound.
Colorless powder, MS spectrum: 314[M+H]$^+$

Example 122

4-(3-Chloro-4-methylphenyloxy)-6-methyl-4,5,6,7-tetrahydrofuro[2,3-c]pyridine hydrochloride The same method as in Example 3 was conducted using 6-methyl-4,5,6,7-tetrahydrofuro[2,3-c]pyridin-4-ol (Reference Example 1) instead of 6-methyl-4,5,6,7-tetrahydrothieno[2,3-c]pyridin-4-ol (Reference Example 6) and was conducted using 2-chloro-4-fluoro-1-methylbenzene instead of 1,3-difluorobenzene to give the objective compound.
Pale yellow solid, MS spectrum: 278[M+H]$^+$

Example 123

4-(3,4-Dichlorophenyloxy)-2,6-dimethyl-5,6,7,8-tetrahydro-4H-furo[2,3-d]azepine

The same method as in Example 1 was conducted using 2,6-dimethyl-5,6,7,8-tetrahydro-4H-furo[2,3-d]azepin-4-ol (Reference Example 26) instead of 6-methyl-4,5,6,7-tetrahydrothieno[2,3-c]pyridin-4-ol (Reference Example 6) and was conducted using 3,4-dichloro-1-fluorobenzene instead of 1-fluoronaphthalene to give the objective compound.
Yellow liquid, MS spectrum: 326[M+H]$^+$

Example 124

4-(Dibenzofuran-2-yloxy)-6-methyl-4,5,6,7-tetrahydrofuro[2,3-c]pyridine hydrochloride The same method as in Example 47 was conducted using 2-hydroxydibenzofuran instead of 4-chloro-3-methylphenol to give the objective compound.
Pale yellow powder, MS spectrum: 320[M+H]$^+$

Example 125

2,6-Dimethyl-4-(naphthalen-1-yloxy)-5,6,7,8-tetrahydro-4H-thieno[2,3-d]azepine

The same method as in Example 1 was conducted using 2,6-dimethyl-5,6,7,8-tetrahydro-4H-furo[2,3-d]azepin-4-ol (Reference Example 26) instead of 6-methyl-4,5,6,7-tetrahydrothieno[2,3-c]pyridin-4-ol (Reference Example 6) to give the objective compound.
Yellow liquid, MS spectrum: 308[M+H]$^+$

Example 126

6-Methyl-4-(naphthalen-1-yloxy)-5,6,7,8-tetrahydro-4H-thieno[2,3-d]azepine hydrochloride The same method as in Example 3 was conducted using 5,6,7,8-tetrahydro-4H-thieno[2,3-d]azepin-4-ol (Reference Example 29) instead of 6-methyl-4,5,6,7-tetrahydrothieno[2,3-c]pyridin-4-ol (Reference Example 6) and was conducted using 1-fluoronaphthalene instead of 1,3-difluorobenzene to give the objective compound.
Colorless powder, MS spectrum: 296[M+H]$^+$

Example 127

4-(3,4-Dichlorophenyloxy)-6-methyl-5,6,7,8-tetrahydro-4H-furo[2,3-d]azepine

The same method as in Example 1 was conducted using 6-methyl-5,6,7,8-tetrahydro-4H-furo[2,3-d]azepin-4-ol (Reference Example 27) instead of 6-methyl-4,5,6,7-tetrahydrothieno[2,3-c]pyridin-4-ol (Reference Example 6) and was conducted using 3,4-dichloro-1-fluorobenzene instead of 1-fluoronaphthalene to give the objective compound.
Yellow liquid, MS spectrum: 312[M+H]$^+$

Example 128

6-Methyl-4-[4-(trifluoromethyl)phenyloxy]-5,6,7,8-tetrahydro-4H-thieno[2,3-d]azepine hydrochloride The same method as in Example 47 was conducted using 6-methyl-5,6,7,8-tetrahydro-4H-thieno[2,3-d]azepin-4-ol (Reference Example 28) instead of 6-methyl-4,5,6,7-tetrahydrofuro[2,3-c]pyridin-4-ol (Reference Example 1) and was conducted using 4-(trifluoromethyl)phenol instead of 4-chloro-3-methylphenol to give the objective compound.
Ecru liquid, MS spectrum: 328[M+H]$^+$

Example 129

4-(4-Ethylphenyloxy)-6-methyl-5,6,7,8-tetrahydro-4H-thieno[2,3-d]azepine hydrochloride The same method as in Example 47 was conducted using 6-methyl-5,6,7,8-tetrahydro-4H-thieno[2,3-d]azepin-4-ol

Example 130

4-[2-(1-Methylpropyl)phenyloxy]-4,5,6,7-tetrahydrofuro[2,3-c]pyridine hydrochloride The same method as in Example 47 was conducted using 4,5,6,7-tetrahydrofuro[2,3-c]pyridin-4-ol (Reference Example 4) instead of 6-methyl-4,5,6,7-tetrahydrofuro[2,3-c]pyridin-4-ol (Reference Example 1) and was conducted using 2-(1-methylpropyl)phenol instead of 4-chloro-3-methylphenol to give the objective compound.
Ecru liquid, MS spectrum: 272[M+H]$^+$

Example 131

4-(2-Propylphenyloxy)-4,5,6,7-tetrahydrofuro[2,3-c]pyridine hydrochloride

The same method as in Example 47 was conducted using 4,5,6,7-tetrahydrofuro[2,3-c]pyridin-4-ol (Reference Example 4) instead of 6-methyl-4,5,6,7-tetrahydrofuro[2,3-c]pyridin-4-ol (Reference Example 1) and was conducted using 2-propylphenol instead of 4-chloro-3-methylphenol to give the objective compound.
Ecru powder, MS spectrum: 258[M+H]$^+$

Example 132

4-[4-(Trifluoromethyl)phenyloxy]-4,5,6,7-tetrahydrofuro[2,3-c]pyridine

The same method as in Example 1 was conducted using 4,5,6,7-tetrahydrofuro[2,3-c]pyridin-4-ol (Reference Example 4) instead of 6-methyl-4,5,6,7-tetrahydrothieno[2,3-c]pyridin-4-ol (Reference Example 6) and was conducted using 4-fluorobenzotrifluoride instead of 1-fluoronaphthalene to give the objective compound.
Pale yellow powder, MS spectrum: 284[M+H]$^+$

Example 133

2,7-dimethyl-4-[4-(trifluoromethyl)phenyloxy]-5,6,7,8-tetrahydro-4H-thieno[2,3-c]azepine hydrochloride The same method as in Example 3 was conducted using 2,7-dimethyl-5,6,7,8-tetrahydro-4H-thieno[2,3-c]azepin-4-ol (Reference Example 23) instead of 6-methyl-4,5,6,7-tetrahydrothieno[2,3-c]pyridin-4-ol (Reference Example 6) and was conducted using 4-fluoro benzotrifluoride instead of 1,3-difluorobenzene to give the objective compound.
Pink powder, MS spectrum: 342[M+H]$^+$

Example 134

4-(4-Bromonaphthalen-1-yloxy)-2,7-dimethyl-5,6,7,8-tetrahydro-4H-thieno[2,3-c]azepine hydrochloride The same method as in Example 3 was conducted using 2,7-dimethyl-5,6,7,8-tetrahydro-4H-thieno[2,3-c]azepin-4-ol (Reference Example 23) instead of 6-methyl-4,5,6,7-tetrahydrothieno[2,3-c]pyridin-4-ol (Reference Example 6) and was conducted using 1-bromo-4-fluoronaphthalene instead of 1,3-difluorobenzene to give the objective compound.
Pink powder, MS spectrum: 402[M+H]$^+$

Example 135

4-(3,4-Dibromophenyloxy)-2,7-dimethyl-5,6,7,8-tetrahydro-4H-thieno[2,3-c]azepine hydrochloride The same method as in Example 3 was conducted using 2,7-dimethyl-5,6,7,8-tetrahydro-4H-thieno[2,3-c]azepin-4-ol (Reference Example 23) instead of 6-methyl-4,5,6,7-tetrahydrothieno[2,3-c]pyridin-4-ol (Reference Example 6) and was conducted using 3,4-dibromo-1-fluorobenzene instead of 1,3-difluorobenzene to give the objective compound.
Pink powder, MS spectrum: 430[M+H]$^+$

Example 136

4-(3,4-Dichlorophenyloxy)-6-methyl-5,6,7,8-tetrahydro-4H-thieno[2,3-d]azepine

The same method as in Example 1 was conducted using 6-methyl-5,6,7,8-tetrahydro-4H-thieno[2,3-d]azepin-4-ol (Reference Example 28) instead of 6-methyl-4,5,6,7-tetrahydrothieno[2,3-c]pyridin-4-ol (Reference Example 6) and was conducted using 3,4-dichloro-1-fluorobenzene instead of 1-fluoronaphthalene to give the objective compound.
Pale yellow liquid, MS spectrum: 328[M+H]$^+$

Example 137

7-Methyl-4-(naphthalen-1-yloxy)-5,6,7,8-tetrahydro-4H-furo[2,3-c]azepine

The same method as in Example 1 was conducted using 7-methyl-5,6,7,8-tetrahydro-4H-furo[2,3-c]azepin-4-ol (Reference Example 19) instead of 6-methyl-4,5,6,7-tetrahydrothieno[2,3-c]pyridin-4-ol (Reference Example 6) to give the objective compound.
Ecru liquid, MS spectrum: 294[M+H]$^+$

Example 138

6-(2-Aminoethyl)-4-(3,4-dichlorophenyloxy)-4,5,6,7-tetrahydrofuro[2,3-c]pyridine dihydrochloride

Step 1

6-{2-[(t-Butoxycarbonyl)amino]ethyl}-4-(3,4-dichlorophenyloxy)-4,5,6,7-tetrahydrofuro[2,3-c]pyridine 4-(3,4-Dichlorophenyloxy)-4,5,6,7-tetrahydrofuro-[2,3-c]pyridine hydrochloride (Example 119) (100 mg) was dissolved in 2 mL of DMF and then 256 mg of cesium carbonate and 87 mg of N-(tert-butoxycarbonyl)-2-bromoethylamine were added successively thereto. This reaction solution was heated at 80° C. with stirring overnight and poured over 30 mL of ice water followed by extracting with ethyl acetate. The organic layer was washed with water and dried over anhydrous magnesium sulfate and the solvent was evaporated therefrom in vacuo. The residue was purified by silica gel column chromatography to give 35 mg of the objective product as an oily substance.

---

(Reference Example 28) instead of 6-methyl-4,5,6,7-tetrahydrofuro[2,3-c]pyridin-4-ol (Reference Example 1) and was conducted using 4-ethylphenol instead of 4-chloro-3-methylphenol to give the objective compound.
Ecru liquid, MS spectrum: 288[M+H]$^+$ Step 2

6-(2-Aminoethyl)-4-(3,4-dichlorophenyloxy)-4,5,6,7-tetrahydrofuro[2,3-c]pyridine dihydrochloride 6-(2-[(tert-Butoxycarbonyl)amino]ethyl)-4-(3,4-di-chlorophenyloxy)-4,5,6,7-tetrahydrofuro[2,3-c]pyridine (35 mg) prepared in the step 1 was dissolved in 2 mL of dehydrated methanol, 20 equivalents of a hydrochloric acid/ethyl acetate solution was dropped thereinto and the mixture was stirred at room temperature for 1 hour. The reaction solution was concentrated in vacuo to evaporate the solvent and excess hydrochloric acid. To the resulting residue was added 2 mL of diethyl ether, the mixture was stirred and the solid separated out therefrom was filtered and dried to give 8 mg of the objective compound.

Brown powder, MS spectrum: 327[M+H]$^+$

Example 139

4-(3,4-Dichlorophenyloxy)-6-(2-hydroxyethyl)-4,5,6,7-tetrahydrofuro[2,3-c]pyridine hydrochloride 4-(3,4-Dichlorophenyloxy)-4,5,6,7-tetrahydrofuro-[2,3-c]pyridine hydrochloride (Example 119) (50 mg) was dissolved in 5 mL of dehydrated ethanol and then 220 mg of 2-iodoethanol was dropped thereinto. The reaction solution was heated with stirring at 80° C. overnight and concentrated in vacuo to evaporate the solvent and excess 2-iodoethanol. The residue was purified by silica gel column chromatography and the resulting free substance of the objective compound was dissolved in 5 mL of ethyl acetate. Into this ethyl acetate solution was dropped a solution of one equivalent of hydrochloric acid ethyl acetate and the resulting mixed solution was concentrated to give 18 mg of the objective compound.

Brown liquid, MS spectrum: 328[M+H]$^+$

Example 140

2,7-Dimethyl-4-(naphthalen-1-yloxy)-5,6,7,8-tetrahydro-4H-furo[2,3-c]azepine

The same method as in Example 1 was conducted using 2,7-dimethyl-5,6,7,8-tetrahydro-4H-furo[2,3-c]azepin-4-ol (Reference Example 20) instead of 6-methyl-4,5,6,7-tetrahydrothieno[2,3-c]pyridin-4-ol (Reference Example 6) to give the objective compound.

Yellow liquid, MS spectrum: 308[M+H]$^+$

Example 141

2,7-Dimethyl-4-[4-(trifluoromethyl)phenyloxy]-5,6,7,8-tetrahydro-4H-furo[2,3-c]azepine The same method as in Example 1 was conducted using 2,7-dimethyl-5,6,7,8-tetrahydro-4H-furo[2,3-c]azepin-4-ol (Reference Example 20) instead of 6-methyl-4,5,6,7-tetrahydrothieno[2,3-c]pyridin-4-ol (Reference Example 6) and was conducted using 4-fluoro benzotrifluoride instead of 1-fluoronaphthalene to give the objective compound.

Pale yellow powder, MS spectrum: 326[M+H]$^+$

Example 142

4-(4-Cyanonaphthalen-1-yloxy)-6-methyl-5,6,7,8-tetrahydro-4H-thieno[2,3-d]azepine hydrochloride The same method as in Example 3 was conducted using 6-methyl-5,6,7,8-tetrahydro-4H-thieno[2,3-d]azepin-4-ol (Reference Example 28) instead of 6-methyl-4,5,6,7-tetrahydrothieno[2,3-c]pyridin-4-ol (Reference Example 6) and was conducted using 1-cyano-4-fluoronaphthalene instead of 1,3-difluorobenzene to give the objective compound.

Colorless powder, MS spectrum: 335[M+H]$^+$

Example 143

4-[3-Chloro-4-(trifluoromethyl)phenyloxy]-6-methyl-5,6,7,8-tetrahydro-4H-thien o[2,3-d]azepine hydrochloride The same method as in Example 3 was conducted using 6-methyl-5,6,7,8-tetrahydro-4H-thieno[2,3-d]azepin-4-ol (Reference Example 28) instead of 6-methyl-4,5,6,7-tetrahydrothieno[2,3-c]pyridin-4-ol (Reference Example 6) and was conducted using 2-chloro-4-fluorobenzotrifluoride instead of 1,3-difluorobenzene to give the objective compound.

Colorless powder, MS spectrum: 362[M+H]$^+$

Example 144

4-[3-Chloro-2-(trifluoromethyl)phenyloxy]-6-methyl-5,6,7,8-tetrahydro-4H-thien o[2,3-d]azepine The same method as in Example 1 was conducted using 6-methyl-5,6,7,8-tetrahydro-4H-thieno[2,3-d]azepin-4-ol (Reference Example 28) instead of 6-methyl-4,5,6,7-tetrahydrothieno[2,3-c]pyridin-4-ol (Reference Example 6) and was conducted using 2-chloro-6-fluorobenzotrifluoride instead of 1-fluoronaphthalene to give the objective compound.

Colorless powder, MS spectrum: 362[M+H]$^+$

Example 145

4-(4-Cyanophenyloxy)-4,5,6,7-tetrahydrofuro[2,3-c]pyridine

The same method as in Example 1 was conducted using 4,5,6,7-tetrahydrofuro[2,3-c]pyridin-4-ol (Reference Example 4) instead of 6-methyl-4,5,6,7-tetrahydrothieno[2,3-c]pyridin-4-ol (Reference Example 6) and was conducted using 4-fluorobenzonitrile instead of 1-fluoronaphthalene to give the objective compound.

Colorless liquid, MS spectrum: 241[M+H]$^+$

Example 146

4-[4-Bromo-2-(trifluoromethyl)phenyloxy]-4,5,6,7-tetrahydrofuro[2,3-c]pyridine

The same method as in Example 1 was conducted using 4,5,6,7-tetrahydrofuro[2,3-c]pyridin-4-ol (Reference Example 4) instead of 6-methyl-4,5,6,7-tetrahydrothieno[2,3-c]pyridin-4-ol (Reference Example 6) and was conducted using 5-bromo-2-fluorobenzotrifluoride instead of 1-fluoronaphthalene to give the objective compound.

Ecru liquid, MS spectrum: 362[M+H]$^+$

Example 147

4-(2,3,4-Tribromophenyloxy)-4,5,6,7-tetrahydrofuro[2,3-c]pyridine

The same method as in Example 1 was conducted using 4,5,6,7-tetrahydrofuro[2,3-c]pyridin-4-ol (Reference Example 4) instead of 6-methyl-4,5,6,7-tetrahydrothieno[2, 3-c]pyridin-4-ol (Reference Example 6) and was conducted using 2,3,4-tribromo-1-fluorobenzene instead of 1-fluoronaphthalene 1 to give the objective compound.
Ecru liquid, MS spectrum: 450[M+H]$^+$ Example 148

4-(2,3-Dichlorophenyloxy)-2,7-dimethyl-5,6,7,8-tetrahydro-4H-thieno[2,3-c]azepine hydrochloride The same method as in Example 3 was conducted using 2,7-dimethyl-5,6,7,8-tetrahydro-4H-thieno[2,3-c]azepin-4-ol (Reference Example 23) instead of 6-methyl-4,5,6,7-tetrahydrothieno[2,3-c]pyridin-4-ol (Reference Example 6) and was conducted using 2,3-dichloro-1-fluorobenzene instead of 1,3-difluorobenzene to give the objective compound.
Colorless powder, MS spectrum: 342[M+H]$^+$ Example 149

4-(2,3-Dichlorophenyloxy)-7-methyl-5,6,7,8-tetrahydro-4H-thieno[2,3-c]azepine hydrochloride The same method as in Example 3 was conducted using 7-methyl-5,6,7,8-tetrahydro-4H-thieno[2,3-c]azepin-4-ol (Reference Example 22) instead of 6-methyl-4,5,6,7-tetrahydrothieno[2,3-c]pyridin-4-ol (Reference Example 6) and was conducted using 2,3-dichloro-1-fluorobenzene instead of 1,3-difluorobenzene to give the objective compound.
Colorless powder, MS spectrum: 328[M+H]$^+$ Example 150

7-Methyl-4-[4-(trifluoromethyl)phenyloxy]-5,6,7,8-tetrahydro-4H-thieno[2,3-c]azepine hydrochloride The same method as in Example 3 was conducted using 7-methyl-5,6,7,8-tetrahydro-4H-thieno[2,3-c]azepin-4-ol (Reference Example 22) instead of 6-methyl-4,5,6,7-tetrahydrothieno[2,3-c]pyridin-4-ol (Reference Example 6) and was conducted using 4-fluoro benzotrifluoride instead of 1,3-difluorobenzene to give the objective compound.
Colorless powder, MS spectrum: 328[M+H]$^+$ Example 151

2,7-Dimethyl-4-(naphthalen-2-yloxy)-5,6,7,8-tetrahydro-4H-thieno[2,3-c]azepine

The same method as in Example 1 was conducted using 2,7-dimethyl-5,6,7,8-tetrahydro-4H-thieno[2,3-c]azepin-4-ol (Reference Example 23) instead of 6-methyl-4,5,6,7-tetrahydrothieno[2,3-c]pyridin-4-ol (Reference Example 6) and was conducted using 2-fluoronaphthalene instead of 1-fluoronaphthalene to give the objective compound.
Yellow liquid, MS spectrum: 324[M+H]$^+$ Example 152

6-Methyl-4-(naphthalen-2-yloxy)-4,5,6,7-tetrahydrofuro[2,3-c]pyridine hydrochloride The same method as in Example 3 was conducted using 6-methyl-4,5,6,7-tetrahydrofuro[2,3-c]pyridin-4-ol (Reference Example 1) instead of 6-methyl-4,5,6,7-tetrahydrothieno[2,3-c]pyridin-4-ol (Reference Example 6) and was conducted using 2-fluoronaphthalene instead of 1,3-difluorobenzene to give the objective compound.
Pale yellow powder, MS spectrum: 280[M+H]$^+$ Example 153

4-(3-Bromo-2-chlorophenyloxy)-6-methyl-4,5,6,7-tetrahydrofuro[2,3-c]pyridine hydrochloride The same method as in Example 1 was conducted using 6-methyl-4,5,6,7-tetrahydrofuro[2,3-c]pyridin-4-ol (Reference Example 1) instead of 6-methyl-4,5,6,7-tetrahydrothieno[2,3-c]pyridin-4-ol (Reference Example 6) and was conducted using 1-bromo-2-chloro-3-fluorobenzene instead of 1-fluoronaphthalene to give the objective compound.
Colorless powder, MS spectrum: 342[M+H]$^+$ Example 154

4-(3-Acetyl-2,4-dichlorophenyloxy)-6-methyl-4,5,6,7-tetrahydrofuro[2,3-c]pyridine hydrochloride The same method as in Example 3 was conducted using 6-methyl-4,5,6,7-tetrahydrofuro[2,3-c]pyridin-4-ol (Reference Example 1) instead of 6-methyl-4,5,6,7-tetrahydrothieno[2,3-c]pyridin-4-ol (Reference Example 6) and was conducted using 2,6-dichloro-3-fluoroacetophenone instead of 1,3-difluorobenzene to give the objective compound.
Colorless powder, MS spectrum: 340[M+H]$^+$ Example 155

4-(3-Chloro-2-methylphenyloxy)-6-methyl-4,5,6,7-tetrahydrofuro[2,3-c]pyridine hydrochloride The same method as in Example 3 was conducted using 6-methyl-4,5,6,7-tetrahydrofuro[2,3-c]pyridin-4-ol (Reference Example 1) instead of 6-methyl-4,5,6,7-tetrahydrothieno[2,3-c]pyridin-4-ol (Reference Example 6) and was conducted using 2-chloro-6-fluorotoluene instead of 1,3-difluorobenzene to give the objective compound.
Colorless powder, MS spectrum: 278[M+H]$^+$ Example 156

4-(3,4-Dichlorophenyloxy)-7-methyl-5,6,7,8-tetrahydro-4H-furo[2,3-c]azepine

The same method as in Example 1 was conducted using 7-methyl-5,6,7,8-tetrahydro-4H-furo[2,3-c]azepin-4-ol (Reference Example 19) instead of 6-methyl-4,5,6,7-tetrahydrothieno[2,3-c]pyridin-4-ol (Reference Example 6) and was conducted using 3,4-dichloro-1-fluorobenzene instead of 1-fluoronaphthalene to give the objective compound.
Pale yellow liquid, MS spectrum: 312[M+H]$^+$ Example 157

5-Methyl-8-(naphthalen-1-yloxy)-5,6,7,8-tetrahydro-4H-furo[3,2-c]azepine

The same method as in Example 1 was conducted using 5-methyl-5,6,7,8-tetrahydro-4H-furo[3,2-c]azepin-8-ol (Reference Example 21) instead of 6-methyl-4,5,6,7-tetrahydrothieno[2,3-c]pyridin-4-ol (Reference Example 6) to give the objective compound.
Pale yellow liquid,
MS spectrum: 294[M+H]$^+$

Example 158

8-(3,4-Dichlorophenyloxy)-5-methyl-5,6,7,8-tetrahydro-4H-furo[3,2-c]azepine

The same method as in Example 1 was conducted using 5-methyl-5,6,7,8-tetrahydro-4H-furo[3,2-c]azepin-8-ol (Reference Example 21) instead of 6-methyl-4,5,6,7-tetrahydrothieno[2,3-c]pyridin-4-ol (Reference Example 6) and was conducted using 3,4-dichloro-1-fluorobenzene instead of 1-fluoronaphthalene to give the objective compound.
Pale yellow liquid, MS spectrum: 312[M+H]$^+$

Example 159

8-(3,4-Dibromophenyloxy)-5-methyl-5,6,7,8-tetrahydro-4H-furo[3,2-c]azepine

The same method as in Example 1 was conducted using 5-methyl-5,6,7,8-tetrahydro-4H-furo[3,2-c]azepin-8-ol (Reference Example 21) instead of 6-methyl-4,5,6,7-tetrahydrothieno[2,3-c]pyridin-4-ol (Reference Example 6) and was conducted using 3,4-dibromo-1-fluorobenzene instead of 1-fluoronaphthalene to give the objective compound.
Pale yellow liquid, MS spectrum: 400[M+H]$^+$

Example 160

8-(4-Bromonaphthalen-1-yloxy)-5-methyl-5,6,7,8-tetrahydro-4H-furo[3,2-c]azepine

The same method as in Example 1 was conducted using 5-methyl-5,6,7,8-tetrahydro-4H-furo[3,2-c]azepin-8-ol (Reference Example 21) instead of 6-methyl-4,5,6,7-tetrahydrothieno[2,3-c]pyridin-4-ol (Reference Example 6) and was conducted using 1-bromo-4-fluoronaphthalene instead of 1-fluoronaphthalene to give the objective compound.
Ecru powder, MS spectrum: 372[M+H]$^+$

Example 161

6-Methyl-4-(quinolin-8-yloxy)-4,5,6,7-tetrahydrofuro[2,3-c]pyridine

The same method as in Example 38 was conducted using 5-hydroxyquinoline instead of 8-hydroxyquinoline to give the objective compound.
Yellow liquid, MS spectrum: 281[M+H]$^+$

Example 162

6-(2-Aminoethyl)-4-(3,4-dichlorophenyloxy)-5,6,7,8-tetrahydro-4H-thieno[2,3-d]azepine dhydrochloride The same method as in Example 138 was conducted using 4-(3,4-dichlorophenyloxy)-6-methyl-5,6,7,8-tetrahydro-4H-thieno[2,3-d]azepine hydrochloride (Example 121) instead of 4-(3,4-dichlorophenyloxy)-4,5,6,7-tetrahydrofuro[2,3-c]pyridine hydrochloride (Example 119) to give the objective compound.
Pale yellow powder, MS spectrum: 357[M+H]$^+$

Example 163

4-(2,3-Dichlorophenyloxy)-2,7-dimethyl-5,6,7,8-tetrahydro-4H-furo[2,3-c]azepine

The same method as in Example 1 was conducted using 2,7-dimethyl-5,6,7,8-tetrahydro-4H-furo[2,3-c]azepin-4-ol (Reference Example 20) instead of 6-methyl-4,5,6,7-tetrahydrothieno[2,3-c]pyridin-4-ol (Reference Example 6) and was conducted using 2,3-dichloro-1-fluorobenzene instead of 1-fluoronaphthalene to give the objective compound.
Brown solid, MS spectrum: 326[M+H]$^+$

Example 164

6-Methyl-4-(5,6,7,8-tetrahydronaphthalen-1-yloxy)-4,5,6,7-tetrahydrofuro[2,3-c]pyridine hydrochloride The same method as in Example 47 was conducted using 5,6,7,8-tetrahydro-1-naphthol instead of 4-chloro-3-methylphenol to give the objective compound.
Pale yellow powder, MS spectrum: 284[M+H]$^+$

Example 165

6-Methyl-4-(2,4,5-trichlorophenyloxy)-4,5,6,7-tetrahydrofuro[2,3-c]pyridine

The same method as in Example 38 was conducted using 2,4,5-trichlorophenol instead of 8-hydroxyquinoline to give the objective compound.
Colorless powder, MS spectrum: 332[M+H]$^+$

Example 166

4-(1-Bromonaphthalen-2-yloxy)-6-methyl-4,5,6,7-tetrahydrofuro[2,3-c]pyridine hydrochloride The same method as in Example 47 was conducted using 1-bromo-2-naphthol instead of 4-chloro-3-methylphenol to give the objective compound.
Pale yellow powder, MS spectrum: 358[M+H]$^+$

Example 167

5-Methyl-8-[4-(trifluoromethyl)phenyloxy]-5,6,7,8-tetrahydro-4H-furo[3,2-c]azepine The same method as in Example 1 was conducted using 5-methyl-5,6,7,8-tetrahydro-4H-furo[3,2-c]azepin-8-ol (Reference Example 21) instead of 6-methyl-4,5,6,7-tetrahydrothieno[2,3-c]pyridin-4-ol (Reference Example 6) and was conducted using 4-fluorobenzotrifluoride instead of 1-fluoronaphthalene to give the objective compound.
Colorless powder, MS spectrum: 312[M+H]$^+$

Example 168

8-(2,3-Dichlorophenyloxy)-5-methyl-5,6,7,8-tetrahydro-4H-furo[3,2-c]azepine

The same method as in Example 1 was conducted using 5-methyl-5,6,7,8-tetrahydro-4H-furo[3,2-c]azepin-8-ol (Reference Example 21) instead of 6-methyl-4,5,6,7-tetrahydrothieno[2,3-c]pyridin-4-ol (Reference Example 6) and was conducted using 2,3-dichloro-1-fluorobenzene instead of 1-fluoronaphthalene to give the objective compound.
Ecru powder, MS spectrum: 312[M+H]$^+$

Example 169

4-(2,3-Dichlorophenyloxy)-7-methyl-5,6,7,8-tetrahydro-4H-furo[2,3-c]azepine

The same method as in Example 1 was conducted using 7-methyl-5,6,7,8-tetrahydro-4H-furo[2,3-c]azepin-4-ol (Reference Example 19) instead of 6-methyl-4,5,6,7-tetrahydrothieno[2,3-c]pyridin-4-ol (Reference Example 6) and was conducted using 2,3-dichloro-1-fluorobenzene instead of 1-fluoronaphthalene to give the objective compound.
Pale yellow liquid, MS spectrum: 312[M+H]$^+$ Example 170

4-(4-Bromonaphthalen-1-yloxy)-7-methyl-5,6,7,8-tetrahydro-4H-furo[2,3-c]azepine

The same method as in Example 1 was conducted using 7-methyl-5,6,7,8-tetrahydro-4H-furo[2,3-c]azepin-4-ol (Reference Example 19) instead of 6-methyl-4,5,6,7-tetrahydrothieno[2,3-c]pyridin-4-ol (Reference Example 6) and was conducted using 1-bromo-4-fluoronaphthalene instead of 1-fluoronaphthalene to give the objective compound.
Yellow liquid, MS spectrum: 372[M+H]$^+$ Example 171

4-(3,4-Dibromophenyloxy)-7-methyl-5,6,7,8-tetrahydro-4H-furo[2,3-c]azepine

The same method as in Example 1 was conducted using 7-methyl-5,6,7,8-tetrahydro-4H-furo[2,3-c]azepin-4-ol (Reference Example 19) instead of 6-methyl-4,5,6,7-tetrahydrothieno[2,3-c]pyridin-4-ol (Reference Example 6) and was conducted using 3,4-dibromo-1-fluorobenzene instead of 1-fluoronaphthalene to give the objective compound.
Pale yellow liquid, MS spectrum: 400[M+H]$^+$ Example 172

7-Methyl-4-(naphthalen-2-yloxy)-5,6,7,8-tetrahydro-4H-furo[2,3-c]azepine

The same method as in Example 1 was conducted using 7-methyl-5,6,7,8-tetrahydro-4H-furo[2,3-c]azepin-4-ol (Reference Example 19) instead of 6-methyl-4,5,6,7-tetrahydrothieno[2,3-c]pyridin-4-ol (Reference Example 6) and was conducted using 2-fluoronaphthalene instead of 1-fluoronaphthalene to give the objective compound.
Brown liquid, MS spectrum: 294[M+H]$^+$ Example 173

7-Methyl-4-[4-(trifluoromethyl)phenyloxy]-5,6,7,8-tetrahydro-4H-furo[2,3-c]azepine The same method as in Example 1 was conducted using 7-methyl-5,6,7,8-tetrahydro-4H-furo[2,3-c]azepin-4-ol (Reference Example 19) instead of 6-methyl-4,5,6,7-tetrahydrothieno[2,3-c]pyridin-4-ol (Reference Example 6) and was conducted using 4-fluorobenzotrifluoride instead of 1-fluoronaphthalene to give the objective compound.
Colorless powder, MS spectrum: 312[M+H]$^+$ Example 174

4-(4-Chloro-3-nitrophenyloxy)-6-methyl-4,5,6,7-tetrahydrofuro[2,3-c]pyridine

The same method as in Example 1 was conducted using 6-methyl-4,5,6,7-tetrahydrofuro[2,3-c]pyridin-4-ol (Reference Example 1) instead of 6-methyl-4,5,6,7-tetrahydrothieno[2,3-c]pyridin-4-ol (Reference Example 6) and was conducted using 2-chloro-5-fluoronitrobenzene instead of 1-fluoronaphthalene to give the objective compound.
Pale yellow powder, MS spectrum: 309[M+H]$^+$ Example 175

6-Methyl-4-(5,6,7,8-tetrahydronaphthalen-2-yloxy)-4,5,6,7-tetrahydrofuro[2,3-c]pyridine hydrochloride The same method as in Example 47 was conducted using 5,6,7,8-tetrahydro-2-naphthol instead of 4-chloro-3-methylphenol to give the objective compound.
Pale yellow powder, MS spectrum: 284[M+H]$^+$ Example 176

5-Methyl-8-(naphthalen-2-yloxy)-5,6,7,8-tetrahydro-4H-furo[3,2-c]azepine

The same method as in Example 1 was conducted using 5-methyl-5,6,7,8-tetrahydro-4H-furo[3,2-c]azepin-8-ol (Reference Example 21) instead of 6-methyl-4,5,6,7-tetrahydrothieno[2,3-c]pyridin-4-ol (Reference Example 6) and was conducted using 2-fluoronaphthalene instead of 1-fluoronaphthalene to give the objective compound.
Brown liquid, MS spectrum: 294[M+H]$^+$ Example 177

4-(3-Bromo-2-chlorophenyloxy)-7-methyl-5,6,7,8-tetrahydro-4H-furo[2,3-c]azepine

The same method as in Example 1 was conducted using 7-methyl-5,6,7,8-tetrahydro-4H-furo[2,3-c]azepin-4-ol (Reference Example 19) instead of 6-methyl-4,5,6,7-tetrahydrothieno[2,3-c]pyridin-4-ol (Reference Example 6) and was conducted using 3-bromo-2-chloro-1-fluorobenzene instead of 1-fluoronaphthalene to give the objective compound.
Yellow liquid, MS spectrum: 356[M+H]$^+$ Example 178

4-[3-Chloro-2-(trifluoromethyl)phenyloxy]-7-methyl-5,6,7,8-tetrahydro-4H-furo[2,3-c]azepine The same method as in Example 1 was conducted using 7-methyl-5,6,7,8-tetrahydro-4H-furo[2,3-c]azepin-4-ol (Reference Example 19) instead of 6-methyl-4,5,6,7-tetrahydrothieno[2,3-c]pyridin-4-ol (Reference Example 6) and was conducted using 2-chloro-6-fluorobenzotrifluoride instead of 1-fluoronaphthalene to give the objective compound.
Yellow liquid, MS spectrum: 346[M+H]$^+$ Example 179

7-Methyl-4-(naphthalen-1-yloxy)-5,6,7,8-tetrahydro-4H-furo[2,3-c]azepine hydrochloride The same method as in Example 3 was conducted using 7-methyl-5,6,7,8-tetrahydro-4H-furo[2,3-c]azepin-4-ol (Reference Example 19) instead of 6-methyl-4,5,6,7-tetrahydrothieno[2,3-c]pyridin-4-ol (Reference Example 6) and was conducted using 1-fluoronaphthalene instead of 1,3-difluorobenzene to give the objective compound.
Colorless powder, MS spectrum: 294[M+H]$^+$

Example 180

2,7-Dimethyl-4-(naphthalen-2-yloxy)-5,6,7,8-tetrahydro-4H-furo[2,3-c]azepine hydrochloride The same method as in Example 3 was conducted using 2,7-dimethyl-5,6,7,8-tetrahydro-4H-furo[2,3-c]azepin-4-ol (Reference Example 20) instead of 6-methyl-4,5,6,7-tetrahydrothieno[2,3-c]pyridin-4-ol (Reference Example 6) and was conducted using 2-fluoronaphthalene instead of 1,3-difluorobenzene to give the objective compound.
Pale yellow powder, MS spectrum: 308[M+H]$^+$

Example 181

4-(3,4-Dibromophenyloxy)-2,7-dimethyl-5,6,7,8-tetrahydro-4H-furo[2,3-c]azepine hydrochloride The same method as in Example 3 was conducted using 2,7-dimethyl-5,6,7,8-tetrahydro-4H-furo[2,3-c]azepin-4-ol (Reference Example 20) instead of 6-methyl-4,5,6,7-tetrahydrothieno[2,3-c]pyridin-4-ol (Reference Example 6) and was conducted using 3,4-dibromo-1-fluorobenzene instead of 1,3-difluorobenzene to give the objective compound.
Pale yellow powder, MS spectrum: 416[M+H]$^+$

Example 182

4-(4-Bromonaphthalen-1-yloxy)-2,7-dimethyl-5,6,7,8-tetrahydro-4H-furo[2,3-c]azepine hydrochloride The same method as in Example 3 was conducted using 2,7-dimethyl-5,6,7,8-tetrahydro-4H-furo[2,3-c]azepin-4-ol (Reference Example 20) instead of 6-methyl-4,5,6,7-tetrahydrothieno[2,3-c]pyridin-4-ol (Reference Example 6) and was conducted using 1-bromo-4-fluoronaphthalene instead of 1,3-difluorobenzene to give the objective compound.
Pale yellow powder, MS spectrum: 386[M+H]$^+$

Example 183

4-(1-Bromonaphthalen-2-yloxy)-2,7-dimethyl-5,6,7,8-tetrahydro-4H-furo[2,3-c]azepine hydrochloride The same method as in Example 47 was conducted using 2,7-dimethyl-5,6,7,8-tetrahydro-4H-furo[2,3-c]azepin-4-ol (Reference Example 20) instead of 6-methyl-4,5,6,7-tetrahydrofuro[2,3-c]pyridin-4-ol (Reference Example 1) and was conducted using 1-bromo-2-naphthol instead of 4-chloro-3-methylphenol to give the objective compound.
Pale yellow powder, MS spectrum: 386[M+H]$^+$

Example 184

4-(2,3-Dimethoxyphenyloxy)-6-methyl-4,5,6,7-tetrahydrofuro[2,3-c]pyridine hydrochloride The same method as in Example 47 was conducted using 2,3-dimethoxy-1-phenol instead of 4-chloro-3-methylphenol to give the objective compound.
Colorless powder, MS spectrum: 290[M+H]$^+$

Example 185

4-[3-Chloro-4-(trifluoromethyl)-phenyloxy]-6-methyl-4,5,6,7-tetrahydrofuro[2,3-c]pyridine The same method as in Example 1 was conducted using 2-chloro-4-fluorobenzotrifluoride instead of 1-fluoronaphthalene to give the objective compound.
Pale yellow powder, MS spectrum: 332[M+H]$^+$

Example 186

4-(2-Acetyl-3-chlorophenyloxy)-6-methyl-4,5,6,7-tetrahydrofuro[2,3-c]pyridine hydrochloride The same method as in Example 3 was conducted using 6-methyl-4,5,6,7-tetrahydrofuro[2,3-c]pyridin-4-ol (Reference Example 1) instead of 6-methyl-4,5,6,7-tetrahydrothieno[2,3-c]pyridin-4-ol (Reference Example 6) and was conducted using 2-chloro-6-fluoroacetophenone instead of 1,3-difluorobenzene to give the objective compound.
Colorless powder, MS spectrum: 306[M+H]$^+$

Example 187

4-(3,4-Dibromophenyloxy)-2,6-dimethyl-4,5,6,7-tetrahydrofuro[2,3-c]pyridine hydrochloride The same method as in Example 3 was conducted using 2,6-dimethyl-4,5,6,7-tetrahydrofuro[2,3-c]pyridin-4-ol (Reference Example 2) instead of 6-methyl-4,5,6,7-tetrahydrothieno[2,3-c]pyridin-4-ol (Reference Example 6) and was conducted using 3,4-dibromo-1-fluorobenzene instead of 1,3-difluorobenzene to give the objective compound.
Colorless powder, MS spectrum: 400[M+H]$^+$

Example 188

2,6-Dimethyl-4-(naphthalen-1-yloxy)-4,5,6,7-tetrahydrofuro[2,3-c]pyridine hydrochloride The same method as in Example 3 was conducted using 2,6-dimethyl-4,5,6,7-tetrahydrofuro[2,3-c]pyridin-4-ol (Reference Example 2) instead of 6-methyl-4,5,6,7-tetrahydrothieno[2,3-c]pyridin-4-ol (Reference Example 6) and was conducted using 1-fluoronaphthalene instead of 1,3-difluorobenzene to give the objective compound.
Pale yellow powder, MS spectrum: 294[M+H]$^+$

Example 189

2,6-Dimethyl-4-[4-(trifluoromethyl)phenyloxy]-4,5,6,7-tetrahydrofuro[2,3-c]pyridine The same method as in Example 1 was conducted using 2,6-dimethyl-4,5,6,7-tetrahydrofuro[2,3-c]pyridin-4-ol (Reference Example 2) instead of 6-methyl-4,5,6,7-tetrahydrothieno[2,3-c]pyridin-4-ol (Reference Example 6) and was conducted using 4-fluorobenzotrifluoride instead of 1-fluoronaphthalene to give the objective compound.
Colorless powder, MS spectrum: 312[M+H]$^+$

Example 190

2,6-Dimethyl-4-(naphthalen-2-yloxy)-4,5,6,7-tetrahydrofuro[2,3-c]pyridine hydrochloride The same method as in Example 3 was conducted using 2,6-dimethyl-4,5,6,7-tetrahydrofuro[2,3-c]pyridin-4-ol (Reference Example 2) instead of 6-methyl-4,5,6,7-tetrahydrothieno[2,3-c]pyridin-4-ol (Reference Example 6) and was conducted using 2-fluoronaphthalene instead of 1,3-difluorobenzene to give the objective compound.
Pale yellow powder, MS spectrum: 294[M+H]$^+$

Example 191

4-(1-Bromonaphthalen-2-yloxy)-2,6-dimethyl-4,5,6,7-tetrahydrofuro[2,3-c]pyridine hydrochloride The same method as in Example 47 was conducted using 2,6-dimethyl-4,5,6,7-tetrahydrofuro[2,3-c]pyridin-4-ol (Reference Example 2) instead of 6-methyl-4,5,6,7-tetrahydrofuro[2,3-c]pyridin-4-ol (Reference Example 1) and was conducted using 1-bromo-2-naphthol instead of 4-chloro-3-methylphenol to give the objective compound.
Pale yellow powder, MS spectrum: 372[M+H]+

Example 192

6-Methyl-4-[4-(benzyloxycarbonyl)phenyloxy-4,5,6,7-tetrahydrofuro[2,3-c]pyridine hydrochloride The same method as in Example 47 was conducted using 4-hydroxybenzylbenzoate instead of 4-chloro-3-methylphenol to give the objective compound.
Colorless powder, MS spectrum: 364[M+H]+

Example 193

6-Methyl-4-[4-(hydroxycarbonyl)phenyloxy-4,5,6,7-tetrahydrofuro[2,3-c]pyridine

In an argon atmosphere, 55 mg of 6-methyl-4-[4-(benzyloxycarbonyl)phenyloxy]-4,5,6,7-tetra-hydrofuro[2,3-c]pyridine hydrochloride (Example 192) was dissolved in 5 mL of ethyl acetate and 10 mg of a 10% palladium-carbon catalyst was added thereto. The mixture was subjected to a reducing reaction in a hydrogen atmosphere using an ordinary-pressure reduction apparatus. The catalyst was removed by filtering the reaction solution, the filtrate was concentrated and the resulting residue was purified by silica gel column chromatography to give 30 mg of the objective compound.
Colorless powder, MS spectrum: 274[M+H]+

Example 194

4-(3-Bromo-2-chlorophenyloxy)-7-methyl-5,6,7,8-tetrahydro-4H-furo[2,3-c]azepine hydrochloride The same method as in Example 3 was conducted using 7-methyl-5,6,7,8-tetrahydro-4H-furo[2,3-c]azepin-4-ol (Reference Example 19) instead of 6-methyl-4,5,6,7-tetrahydrofuro[2,3-c]pyridin-4-ol (Reference Example 6) and 3-bromo-2-chloro-1-fluorobenzene instead of 1,3-difluorobenzene to give the objective compound.
Colorless powder, MS spectrum: 358[M+H]+

Example 195

4-(Phenyloxy)-6-methyl-4,5,6,7-tetrahydrofuro[2,3-c]pyridine hydrochloride

The same method as in Example 47 was conducted using phenol instead of 4-chloro-3-methylphenol to give the objective compound.
Colorless powder, MS spectrum: 230[M+H]+

Example 196

2,7-Dimethyl-4-(naphthalen-2-yloxy)-5,6,7,8-tetrahydro-4H-furo[2,3-c]azepine

The same method as in Example 1 was conducted using 2,7-dimethyl-5,6,7,8-tetrahydro-4H-furo[2,3-c]azepin-4-ol (Reference Example 20) instead of 6-methyl-4,5,6,7-tetrahydrothieno[2,3-c]pyridin-4-ol (Reference Example 6) and was conducted using 2-fluoronaphthalene instead of 1-fluoronaphthalene to give the objective compound.
Pale yellow liquid, MS spectrum: 308[M+H]+

Example 197

4-(3,4-Dibromophenyloxy)-2,7-dimethyl-5,6,7,8-tetrahydro-4H-furo[2,3-c]azepine

The same method as in Example 1 was conducted using 2,7-dimethyl-5,6,7,8-tetrahydro-4H-furo[2,3-c]azepin-4-ol (Reference Example 20) instead of 6-methyl-4,5,6,7-tetrahydrothieno[2,3-c]pyridin-4-ol (Reference Example 6) and was conducted using 3,4-dibromo-1-fluorobenzene instead of 1-fluoronaphthalene to give the objective compound.
Pale yellow liquid, MS spectrum: 414[M+H]+

Example 198

4-(4-Bromonaphthalen-1-yloxy)-2,7-dimethyl-5,6,7,8-tetrahydro-4H-furo[2,3-c]azepine The same method as in Example 1 was conducted using 2,7-dimethyl-5,6,7,8-tetrahydro-4H-furo[2,3-c]azepin-4-ol (Reference Example 20) instead of 6-methyl-4,5,6,7-tetrahydrothieno[2,3-c]pyridin-4-ol (Reference Example 6) and was conducted using 1-bromo-4-fluoronaphthalene instead of 1-fluoronaphthalene to give the objective compound.
Pale yellow liquid, MS spectrum: 386[M+H]+

Example 199

4-(1-Bromonaphthalen-2-yloxy)-2,7-dimethyl-5,6,7,8-tetrahydro-4H-furo[2,3-c]azepine The same method as in Example 38 was conducted using 2,7-dimethyl-5,6,7,8-tetrahydro-4H-furo[2,3-c]azepin-4-ol (Reference Example 20) instead of 6-methyl-4,5,6,7-tetrahydrofuro[2,3-c]pyridin-4-ol (Reference Example 1) and was conducted using 1-bromo-2-naphthol instead of 8-hydroxyquinoline to give the objective compound.
Pale yellow liquid, MS spectrum: 386[M+H]+

Example 200

4-(3-Bromo-2-chlorophenyloxy)-2,7-dimethyl-5,6,7,8-tetrahydro-4H-furo[2,3-c]azepine The same method as in Example 1 was conducted using 2,7-dimethyl-5,6,7,8-tetrahydro-4H-furo[2,3-c]azepin-4-ol (Reference Example 20) instead of 6-methyl-4,5,6,7-tetrahydrothieno[2,3-c]pyridin-4-ol (Reference Example 6) and was conducted using 3-bromo-2-chloro-1-fluorobenzene instead of 1-fluoronaphthalene to give the objective compound.
Yellow liquid, MS spectrum: 370[M+H]+

Example 201

4-(2,5-Dichlorophenyloxy)-7-methyl-5,6,7,8-tetrahydro-4H-furo[2,3-c]azepine hydrochloride The same method as in Example 3 was conducted using 7-methyl-5,6,7,8-tetrahydro-4H-furo[2,3-c]azepin-4-ol (Reference Example 19) instead of 6-methyl-4,5,6,7-tetrahydrothieno[2,3-c]pyridin-4-ol (Reference Example 6) and was

Example 202

4-(4-Acetylamino-phenyloxy)-6-methyl-4,5,6,7-tetrahydrofuro[2,3-c]pyridine hydrochloride The same method as in Example 47 was conducted using 4-acetylaminophenol instead of 4-chloro-3-methylphenol to give the objective compound.
Colorless powder, MS spectrum: 287[M+H]$^+$

Example 203

4-(2,3-Dichlorophenyloxy)-2,6-dimethyl-4,5,6,7-tetrahydrofuro[2,3-c]pyridine hydrochloride The same method as in Example 3 was conducted using 2,6-dimethyl-4,5,6,7-tetrahydrofuro[2,3-c]pyridin-4-ol (Reference Example 2) instead of 6-methyl-4,5,6,7-tetrahydrothieno[2,3-c]pyridin-4-ol (Reference Example 6) and was conducted using 2,3-dichloro-1-fluorobenzene instead of 1,3-difluorobenzene to give the objective compound.
Colorless powder, MS spectrum: 312[M+H]$^+$

Example 204

6-Methyl-4-(4-phthalimidephenyloxy)-4,5,6,7-tetrahydrofuro[2,3-c]pyridine

The same method as in Example 38 was conducted using 4-phthalimide phenol instead of 8-hydroxyquinoline to give the objective compound.
Colorless powder, MS spectrum: 375[M+H]$^+$

Example 205

4-(4-Aminophenyloxy)-6-methyl-4,5,6,7-tetrahydrofuro[2,3-c]pyridine dihydrochloride The same method as in Example 3 was conducted using 6-methyl-4,5,6,7-tetrahydrofuro[2,3-c]pyridin-4-ol (Reference Example 1) instead of 6-methyl-4,5,6,7-tetrahydrothieno[2,3-c]pyridin-4-ol (Reference Example 6) and 4-aminophenol instead of 1,3-difluorobenzene to give the objective compound.
Colorless powder, MS spectrum: 245[M+H]$^+$

Example 206

4-(4-Methoxyphenyloxy)-6-methyl-4,5,6,7-tetrahydrofuro[2,3-c]pyridine hydrochloride The same method as in Example 47 was conducted using 4-methoxyphenol instead of 4-chloro-3-methylphenol to give the objective compound.
Colorless powder, MS spectrum: 260[M+H]$^+$

Example 207

4-(2,3-Dichlorophenyloxy)-2,7-dimethyl-5,6,7,8-tetrahydro-4H-furo[2,3-c]azepine hydrochloride The same method as in Example 3 was conducted using 2,7-dimethyl-5,6,7,8-tetrahydro-4H-furo[2,3-c]azepin-4-ol (Reference Example 20) instead of 6-methyl-4,5,6,7-tetrahydrothieno[2,3-c]pyridin-4-ol (Reference Example 6) and was conducted using 2,3-dichloro-1-fluorobenzene instead of 1,3-difluorobenzene to give the objective compound.
Pale yellow powder, MS spectrum: 326[M+H]$^+$

Example 208

4-(3-Bromo-2-chlorophenyloxy)-2,7-dimethyl-5,6,7,8-tetrahydro-4H-furo[2,3-c]azepine hydrochloride The same method as in Example 3 was conducted using 2,7-dimethy-5,6,7,8-tetrahydro-4H-furo[2,3-c]azepin-4-ol (Reference Example 20) instead of 6-methyl-4,5,6,7-tetrahydrothieno[2,3-c]pyridin-4-ol (Reference Example 6) and was conducted using 3-bromo-2-chloro-1-fluorobenzene instead of 1,3-difluorobenzene to give the objective compound.
Pale yellow powder, MS spectrum: 370[M+H]$^+$

Example 209

4-(3-Bromo-2-chlorophenyloxy)-2-methyl-5,6,7,8-tetrahydro-4H-furo[2,3-c]azepine hydrochloride The same method as in Example 3 was conducted using 2-methyl-5,6,7,8-tetrahydro-4H-furo[2,3-c]azepin-4-ol (Reference Example 44) instead of 6-methyl-4,5,6,7-tetrahydrothieno[2,3-c]pyridin-4-ol (Reference Example 6) and was conducted using 3-bromo-2-chloro-1-fluorobenzene instead of 1,3-difluorobenzene to give the objective compound.
Pale yellow powder, MS spectrum: 356[M+H]$^+$

Example 210

2,7-Dimethyl-4-(naphthalen-1-yloxy)-5,6,7,8-tetrahydro-4H-furo[2,3-c]azepine L-tartrate The free body of 2,7-dimethyl-4-(naphthalen-1-yloxy)-5,6,7,8-tetrahydro-4H-furo[2,3c]azepine provided with Example 140 was dissolved in methanol, and then into the resulting methanol solution was added 1 equivalent of L-tartaric acid and was stirred for 1 hour. The mixture was concentrated to give the objective compound.
Red-brown powder, MS spectrum: 308[M+H]$^+$

Example 211

2,7-Dimethyl-4-(naphthalen-1-yloxy)-5,6,7,8-tetrahydro-4H-furo[2,3-c]azepine D-tartrate The free body of 2,7-dimethyl-4-(naphthalen-1-yloxy)-5,6,7,8-tetrahydro-4H-furo[2,3-c]azepine provided with Example 140 was dissolved in methanol, and then into the resulting methanol solution was added 1 equivalent of D-tartaric acid and was stirred for 1 hour. The mixture was concentrated to give the objective compound.
Red-brown powder, MS spectrum: 308[M+H]$^+$

Example 212

4-(Carbazol-2-yloxy)-6-methyl-4,5,6,7-tetrahydrofuro[2,3-c]pyridine

The same method as in Example 47 was conducted using carbazol-2-ol instead of 4-chloro-3-methylphenol to give the objective compound.
Colorless powder, MS spectrum: 319[M+H]$^+$

Example 213

4-(2,3-Dichlorophenyloxy)-7-methyl-5,6,7,8-tetrahydro-4H-furo[2,3-c]azepine hydrochloride The same method as in Example 3 was conducted using 7-methyl-5,6,7,8-tetrahydro-4H-furo[2,3-c]azepin-4-ol (Reference Example 19) instead of 6-methyl-4,5,6,7-tetrahydrothieno[2,3-c]pyridin-4-ol (Reference Example 6) and was conducted using 2,3-dichloro-1-fluorobenzene instead of 1,3-difluorobenzene to give the objective compound.
Colorless powder, MS spectrum: 312[M+H]$^+$

Example 214

4-(4-Methanesulphonylphenyloxy)-2,6-dimethyl-4,5,6,7-tetrahydrofuro[2,3-c]pyridine hydrochloride The same method as in Example 47 was conducted using 2,6-dimethyl-4,5,6,7-tetrahydrofuro[2,3-c]pyridin-4-ol (Reference Example 2) instead of 6-methyl-4,5,6,7-tetrahydrofuro[2,3-c]pyridin-4-ol (Reference Example 1) and was conducted using 4-methanesulfonylphenol instead of 4-chloro-3-methylphenol to give the objective compound.
Colorless powder, MS spectrum: 322[M+H]$^+$

Example 215

4-(3,5-Bis(methoxycarbonyl)-phenyloxy)-2,6-dimethyl-4,5,6,7-tetrahydrofuro[2,3-c]pyridine hydrochloride The same method as in Example 47 was conducted using 2,6-dimethyl-4,5,6,7-tetrahydrofuro[2,3-c]pyridin-4-ol (Reference Example 2) instead of 6-methyl-4,5,6,7-tetrahydrofuro[2,3-c]pyridin-4-ol (Reference Example 1) and was conducted using 3,5-bis(methoxycarbonyl)phenol instead of 4-chloro-3-methylphenol to give the objective compound.
Pale yellow powder, MS spectrum: 360[M+H]$^+$

Example 216

4-(2,4-Difluorophenyloxy)-2,6-dimethyl-4,5,6,7-tetrahydrofuro[2,3-c]pyridine hydrochloride The same method as in Example 47 was conducted using 2,6-dimethyl-4,5,6,7-tetrahydrofuro[2,3-c]pyridin-4-ol (Reference Example 2) instead of 6-methyl-4,5,6,7-tetrahydrofuro[2,3-c]pyridin-4-ol (Reference Example 1) and was conducted using 2,4-difluorophenol instead of 4-chloro-3-methylphenol to give the objective compound.
Colorless powder, MS spectrum: 280[M+H]$^+$

Example 217

5-Methyl-8-(naphthalen-1-yloxy)-5,6,7,8-tetrahydro-4H-furo[3,2-c]azepine hydrochloride The same method as in Example 3 was conducted using 5-methyl-5,6,7,8-tetrahydro-4H-furo[3,2-c]azepin-8-ol (Reference Example 21) instead of 6-methyl-4,5,6,7-tetrahydrothieno[2,3-c]pyridin-4-ol (Reference Example 6) and was conducted using 1-fluoronaphthalene instead of 1,3-difluorobenzene to give the objective compound.
Colorless powder, MS spectrum: 294[M+H]$^+$

Example 218

5-Methyl-8-(naphthalen-1-yloxy)-5,6,7,8-tetrahydro-4H-furo[3,2-c]azepine citrate The free body of 5-methyl-8-(naphthalen-1-yloxy)-5,6,7,8-tetrahydro-4H-furo[3,2-c]azepine provided with Example 157 was dissolved in methanol, and then into the resulting methanol solution was added 1 equivalent of citric acid and was stirred for 1 hour.
The mixture was concentrated to give the objective compound. Colorless powder, MS spectrum: 294[M+H]$^+$

Example 219

8-(3,4-Dichlorophenyloxy)-5-methyl-5,6,7,8-tetrahydro-4H-furo[3,2-c]azepine citrate The free body of 8-(3,4-dichlorophenyloxy)-5-methyl-5,6,7,8-tetrahydro-4H-furo[3,2-c]azepine provided with Example 158 was dissolved in methanol, and then into the resulting methanol solution was added 1 equivalent of citric acid and was stirred for 1 hour. The mixture was concentrated to give the objective compound.
Colorless powder, MS spectrum: 312[M+H]$^+$

Example 220

4-(5-Chloropyridin-2-yloxy)-2,6-dimethyl-4,5,6,7-tetrahydrofuro[2,3-c]pyridine hydrochloride Into 1 mL of DMF was suspended 18 mg of 60% sodium hydride, then 50 mg of 2,6-dimethyl-4,5,6,7-tetrahydrofuro[2,3-c]-pyridin-4-ol (Reference Example 2) was added thereto, the mixture was stirred at room temperature for 10 minutes and 0.13 g of 2,5-dichloropyridine was added thereto followed by stirring at 90° C. for 15 hours. The reaction solution was cooled, a saturated aqueous solution of sodium hydrogen carbonate was added thereto and the mixture was subjected to extraction with ethyl acetate. The organic layer was washed with a saturated solution of sodium chloride and dried over anhydrous magnesium sulfate and the solvent was evaporated therefrom in vacuo. The residue was purified by silica gel column chromatography to give 65 mg of a free substance of the objective compound.
The resulting free substance was dissolved in ethyl acetate, a hydrochloric acid/ethyl acetate solution was dropped thereinto and the powder separated out therefrom was filtered and dried to give 55 mg of the objective compound.
Pale yellow powder, MS spectrum: 279[M+H]$^+$

Example 221

4-(4-Nitrophenyloxy)-6-methyl-4,5,6,7-tetrahydrofuro[2,3-c]pyridine

The same method as in Example 38 was conducted using 4-nitrophenol instead of 8-hydroxyquinoline to give the objective compound.
Colorless powder, MS spectrum: 275[M+H]$^+$

Example 222

2,7-Dimethyl-4-(naphthalen-1-yloxy)-5,6,7,8-tetrahydro-4H-furo[2,3-c]azepine hydrochloride The same method as in Example 3 was conducted using 2,7-dimethyl-5,6,7,8-tetrahydro-4H-furo[2,3-c]azepin-4-ol (Reference Example 20) instead of 6-methyl-4,5,6,7-tetrahydrothieno[2,3-c]pyridin-4-ol (Reference Example 6) and was conducted using 1-fluoronaphthalene instead of 1,3-difluorobenzene to give the objective compound.
Pink powder, MS spectrum: 308[M+H]$^+$ Example 223

4-(2-Chloro-4-cyanophenyloxy)-7-methyl-5,6,7,8-tetrahydro-4H-furo[2,3-c]azepine hydrochloride The same method as in Example 3 was conducted using 7-methyl-5,6,7,8-tetrahydro-4H-furo[2,3-c]azepin-4-ol (Reference Example 19) instead of 6-methyl-4,5,6,7-tetrahydrothieno[2,3-c]pyridin-4-ol (Reference Example 6) and was conducted using 3-chloro-4-fluorobenzonitrile instead of 1,3-difluorobenzene to give the objective compound.
Pink powder, MS spectrum: 303[M+H]$^+$ Example 224

4-(2,4-Dichlorophenyloxy)-7-methyl-5,6,7,8-tetrahydro-4H-furo[2,3-c]azepine hydrochloride The same method as in Example 3 was conducted using 7-methyl-5,6,7,8-tetrahydro-4H-furo[2,3-c]azepin-4-ol (Reference Example 19) instead of 6-methyl-4,5,6,7-tetrahydrothieno[2,3-c]pyridin-4-ol (Reference Example 6) and was conducted using 2,4-dichloro-1-fluorobenzene instead of 1,3-difluorobenzene to give the objective compound.
Colorless powder, MS spectrum: 312[M+H]$^+$ Example 225

4-(2-Chloro-4-carbamoylphenyloxy)-7-methyl-5,6,7,8-tetrahydro-4H-furo[2,3-c]azepine hydrochloride The same method as in Example 3 was conducted using 7-methyl-5,6,7,8-tetrahydro-4H-furo[2,3-c]azepin-4-ol (Reference Example 19) instead of 6-methyl-4,5,6,7-tetrahydrothieno[2,3-c]pyridin-4-ol (Reference Example 6) and was conducted using 4-carbamoyl-2-chloro-1-fluorobenzene instead of 1,3-difluorobenzene to give the objective compound.
Pale yellow powder, MS spectrum: 321[M+H]$^+$ Example 226

4-(Isoquinolin-1-yloxy)-2,6-dimethyl-4,5,6,7-tetrahydrofuro[2,3-c]pyridine dihydrochloride The same method as in Example 220 was conducted using 1-chloroisoquinoline instead of 2,5-dichloropyridine to give the objective compound.
Ecru powder, MS spectrum: 295[M+H]$^+$ Example 227

4-(4-Methylphenyloxy)-6-methyl-4,5,6,7-tetrahydrofuro[2,3-c]pyridine hydrochloride The same method as in Example 47 was conducted using 4-methylphenol instead of 4-chloro-3-methylphenol to give the objective compound.
Pale yellow powder, MS spectrum: 244[M+H]$^+$ Example 228

4-(4-Carbamoylphenyloxy)-6-methyl-4,5,6,7-tetrahydrofuro[2,3-c]pyridine hydrochloride The same method as in Example 47 was conducted using 4-carbamoylphenol instead of 4-chloro-3-methylphenol to give the objective compound.
Colorless powder, MS spectrum: 273[M+H]$^+$ Example 229

4-(Indol-4-yloxy)-6-methyl-4,5,6,7-tetrahydrofuro[2,3-c]pyridine hydrochloride

The same method as in Example 47 was conducted using 4-hydroxyindole instead of 4-chloro-3-methylphenol to give the objective compound.
Colorless powder, MS spectrum: 269[M+H]$^+$ Example 230

4-[(4-Hydroxymethyl)phenyloxy]-6-methyl-4,5,6,7-tetrahydrofuro[2,3-c]pyridine hydrochloride The same method as in Example 47 was conducted using 4-hydroxymethylphenol instead of 4-chloro-3-methylphenol to give the objective compound.
Colorless powder, MS spectrum: 260[M+H]$^+$ Example 231

4-(3-Amino-4-chlorophenyloxy)-6-methyl-4,5,6,7-tetrahydrofuro[2,3-c]pyridine dihydrochloride The same method as in Example 3 was conducted using 6-methyl-4,5,6,7-tetrahydrofuro[2,3-c]pyridin-4-ol (Reference Example 1) instead of 6-methyl-4,5,6,7-tetrahydrothieno[2,3-c]pyridin-4-ol (Reference Example 6) and was conducted using 3-amino-4-chlorophenol instead of 1,3-difluorobenzene to give the objective compound.
Pale yellow powder, MS spectrum: 279[M+H]$^+$ Example 232

4-(4-Cyanonaphthalen-1-yloxy)-7-methyl-5,6,7,8-tetrahydro-4H-furo[2,3-c]azepine hydrochloride The same method as in Example 3 was conducted using 7-methyl-5,6,7,8-tetrahydro-4H-furo[2,3-c]azepin-4-ol (Reference Example 19) instead of 6-methyl-4,5,6,7-tetrahydrothieno[2,3-c]pyridin-4-ol (Reference Example 6) and was conducted using 1-cyano-4-fluoronaphthalene instead of 1,3-difluorobenzene to give the objective compound.
Pale yellow powder, MS spectrum: 319[M+H]$^+$ Example 233

4-(4-Carbamoylnaphthalen-1-yloxy)-7-methyl-5,6,7,8-tetrahydro-4H-furo[2,3-c]azepine hydrochloride The same method as in Example 3 was conducted using 7-methyl-5,6,7,8-tetrahydro-4H-furo[2,3-c]azepin-4-ol (Reference Example 19) instead of 6-methyl-4,5,6,7-tetrahydrothieno[2,3-c]pyridin-4-ol (Reference Example 6) and was conducted using 1-carbamoyl-4-fluoronaphthalene instead of 1,3-difluorobenzene to give the objective compound.
Pale yellow powder, MS spectrum: 337[M+H]$^+$

Example 234

4-(2-Chlorophenyloxy)-7-methyl-5,6,7,8-tetrahydro-4H-furo[2,3-c]azepine hydrochloride The same method as in Example 3 was conducted using 7-methyl-5,6,7,8-tetrahydro-4H-furo[2,3-c]azepin-4-ol (Reference Example 19) instead of 6-methyl-4,5,6,7-tetrahydrothieno[2,3-c]pyridin-4-ol (Reference Example 6) and was conducted using 1-chloro-2-fluorobenzene instead of 1,3-difluorobenzene to give the objective compound.

White powder, MS spectrum: 278[M+H]$^+$

Example 235

4-(2-Bromophenyloxy)-7-methyl-5,6,7,8-tetrahydro-4H-furo[2,3-c]azepine hydrochloride The same method as in Example 3 was conducted using 7-methyl-5,6,7,8-tetrahydro-4H-furo[2,3-c]azepin-4-ol (Reference Example 19) instead of 6-methyl-4,5,6,7-tetrahydrothieno[2,3-c]pyridin-4-ol (Reference Example 6) and was conducted using 1-bromo-2-fluorobenzene instead of 1,3-difluorobenzene to give the objective compound.

White powder, MS spectrum: 322[M+H]$^+$

Example 236

4-(2-Bromo-4-acetylphenyloxy)-7-methyl-5,6,7,8-tetrahydro-4H-furo[2,3-c]azepine hydrochloride The same method as in Example 3 was conducted using 7-methyl-5,6,7,8-tetrahydro-4H-furo[2,3-c]azepin-4-ol (Reference Example 19) instead of 6-methyl-4,5,6,7-tetrahydrothieno[2,3-c]pyridin-4-ol (Reference Example 6) and was conducted using 1-acetyl-3-bromo-4-fluorobenzene instead of 1,3-difluorobenzene to give the objective compound.

Pale yellow powder, MS spectrum: 364[M+H]$^+$

Example 237

4-(2-Bromo-4-carbamoylphenyloxy)-7-methyl-5,6,7,8-tetrahydro-4H-furo[2,3-c]azepine hydrochloride The same method as in Example 3 was conducted using 7-methyl-5,6,7,8-tetrahydro-4H-furo[2,3-c]azepin-4-ol (Reference Example 19) instead of 6-methyl-4,5,6,7-tetrahydrothieno[2,3-c]pyridin-4-ol (Reference Example 6) and was conducted using 2-bromo-4-carbamoyl-1-fluorobenzene instead of 1,3-difluorobenzene to give the objective compound.

White powder, MS spectrum: 365[M+H]$^+$

Example 238

4-(Benzothiophen-7-yloxy)-2,6-dimethyl-4,5,6,7-tetrahydrofuro[2,3-c]pyridine hydrochloride The same method as in Example 47 was conducted using 7-hydroxybenzothiophene instead of 4-chloro-3-methylphenol to give the objective compound.

Colorless powder, MS spectrum: 300[M+H]$^+$

Example 239

4-(3-Carbamoyl-4-chlorophenyloxy)-2,6-dimethyl-4,5,6,7-tetrahydrofuro[2,3-c]pyridine hydrochloride The same method as in Example 3 was conducted using 2,6-dimethyl-4,5,6,7-tetrahydrofuro[2,3-c]pyridin-4-ol (Reference Example 2) instead of 6-methyl-4,5,6,7-tetrahydrofuro[2,3-c]pyridin-4-ol (Reference Example 1) and was conducted using 3-carbamoyl-4-chloro-1-fluorobenzene instead of 1,3-difluorobenzene to give the objective compound.

White powder, MS spectrum: 321[M+H]$^+$

Example 240

4-(4-Carbamoyl-3-chlorophenyloxy)-2,6-dimethyl-4,5,6,7-tetrahydrofuro[2,3-c]pyridine hydrochloride The same method as in Example 3 was conducted using 2,6-dimethyl-4,5,6,7-tetrahydrofuro[2,3-c]pyridin-4-ol (Reference Example 2) instead of 6-methyl-4,5,6,7-tetrahydrofuro[2,3-c]pyridin-4-ol (Reference Example 1) and was conducted using 4-carbamoyl-3-chloro-1-fluorobenzene instead of 1,3-difluorobenzene to give the objective compound.

White powder, MS spectrum: 321[M+H]$^+$

Example 241

4-(4-Carbamoylnaphthalen-1-yloxy)-2,6-dimethyl-4,5,6,7-tetrahydrofuro[2,3-c]pyridine hydrochloride The same method as in Example 3 was conducted using 2,6-dimethyl-4,5,6,7-tetrahydrofuro[2,3-c]pyridin-4-ol (Reference Example 2) instead of 6-methyl-4,5,6,7-tetrahydrofuro[2,3-c]pyridin-4-ol (Reference Example 1) and was conducted using 4-carbamoyl-1-fluoronaphthalene instead of 1,3-difluorobenzene to give the objective compound.

White powder, MS spectrum: 337[M+H]$^+$

Example 242

4-(2-Carbamoylphenyloxy)-2,6-dimethyl-4,5,6,7-tetrahydrofuro[2,3-c]pyridine hydrochloride The same method as in Example 3 was conducted using 2,6-dimethyl-4,5,6,7-tetrahydrofuro[2,3-c]pyridin-4-ol (Reference Example 2) instead of 6-methyl-4,5,6,7-tetrahydrofuro[2,3-c]pyridin-4-ol (Reference Example 1) and was conducted using 2-carbamoyl-1-fluorobenzene instead of 1,3-difluorobenzene to give the objective compound.

White powder, MS spectrum: 287[M+H]$^+$

Example 243

4-(4-Carbamoyl-2-chlorophenyloxy)-7-methyl-5,6,7,8-tetrahydro-4H-thieno[2,3-c]azepine hydrochloride The same method as in Example 3 was conducted using 7-methyl-5,6,7,8-tetrahydro-4H-thieno[2,3-c]azepin-4-ol (Reference Example 22) instead of 6-methyl-4,5,6,7-tetrahydrothieno[2,3-c]pyridin-4-ol (Reference Example 6) and was conducted using 4-carbamoyl-2-chloro-1-fluorobenzene instead of 1,3-difluorobenzene to give the objective compound.

Pale yellow powder, MS spectrum: 337[M+H]$^+$

Example 244

4-[4-Carbamoyl-2-(trifluoromethyl)phenyloxy]-7-methyl-5,6,7,8-tetrahydro-4H-furo[2,3-c]azepine hydrochloride The same method as in Example 3 was conducted using 7-methyl-5,6,7,8-tetrahydro-4H-furo[2,3-c]azepin-4-ol

Example 245

4-(3-Bromophenyloxy)-7-methyl-5,6,7,8-tetrahydro-4H-furo[2,3-c]azepine hydrochloride The same method as in Example 3 was conducted using 7-methyl-5,6,7,8-tetrahydro-4H-furo[2,3-c]azepin-4-ol (Reference Example 19) instead of 6-methyl-4,5,6,7-tetrahydrothieno[2,3-c]pyridin-4-ol (Reference Example 6) and was conducted using 3-bromo-1-fluorobenzene instead of 1,3-difluorobenzene to give the objective compound.
Colorless powder, MS spectrum: 322[M+H]$^+$

Example 246

4-(4-Carbamoyl-2-chlorophenyloxy)-2,7-dimethyl-5,6,7,8-tetrahydro-4H-furo[2,3-c]azepine hydrochloride The same method as in Example 3 was conducted using 2,7-dimethyl-5,6,7,8-tetrahydro-4H-furo[2,3-c]azepin-4-ol (Reference Example 20) instead of 6-methyl-4,5,6,7-tetrahydrothieno[2,3-c]pyridin-4-ol (Reference Example 6) and conducted using 4-carbamoyl-2-chloro-1-fluorobenzene instead of 1,3-difluorobenzene to give the objective compound.
Pale yellow powder, MS spectrum: 335[M+H]$^+$

Example 247

4-(2-Bromophenyloxy)-2,7-dimethyl-5,6,7,8-tetrahydro-4H-furo[2,3-c]azepine hydrochloride The same method as in Example 3 was conducted using 2,7-dimethyl-5,6,7,8-tetrahydro-4H-furo[2,3-c]azepin-4-ol (Reference Example 20) instead of 6-methyl-4,5,6,7-tetrahydrothieno[2,3-c]pyridin-4-ol (Reference Example 6) and was conducted using 2-bromo-1-fluorobenzene instead of 1,3-difluorobenzene to give the objective compound.
Pale yellow powder, MS spectrum: 336[M+H]$^+$

Example 248

4-(4-Bromophenyloxy)-7-methyl-5,6,7,8-tetrahydro-4H-furo[2,3-c]azepine hydrochloride The same method as in Example 3 was conducted using 7-methyl-5,6,7,8-tetrahydro-4H-furo[2,3-c]azepin-4-ol (Reference Example 19) instead of 6-methyl-4,5,6,7-tetrahydrothieno[2,3-c]pyridin-4-ol (Reference Example 6) and was conducted using 4-bromo-1-fluorobenzene instead of 1,3-difluorobenzene to give the objective compound.
Colorless powder, MS spectrum: 322[M+H]$^+$

Example 249

4-(3-Carbamoylphenyloxy)-2,6-dimethyl-4,5,6,7-tetrahydrofuro[2,3-c]pyridine hydrochloride The same method as in Example 3 was conducted using 2,6-dimethyl-4,5,6,7-tetrahydrofuro[2,3-c]pyridin-4-ol (Reference Example 2) instead of 6-methyl-4,5,6,7-tetrahydrofuro[2,3-c]pyridin-4-ol (Reference Example 1) and was conducted using 3-carbamoyl-1-fluorobenzene instead of 1,3-difluorobenzene to give the objective compound.
Colorless powder, MS spectrum: 287[M+H]$^+$

Example 250

4-(4-Ethylcarbamoyl-2-chlorophenyloxy)-2,7-dimethyl-5,6,7,8-tetrahydro-4H-furo[2,3-c]azepine hydrochloride The same method as in Example 3 was conducted using 2,7-dimethyl-5,6,7,8-tetrahydro-4H-furo[2,3-c]azepin-4-ol (Reference Example 20) instead of 6-methyl-4,5,6,7-tetrahydrothieno[2,3-c]pyridin-4-ol (Reference Example 6) and was conducted using 4-ethylcarbamoyl-2-chloro-1-fluorobenzene instead of 1,3-difluorobenzene to give the objective compound.
Colorless powder, MS spectrum: 363[M+H]$^+$

Example 251

4-(2-Carbamoylphenyloxy)-7-methyl-5,6,7,8-tetrahydro-4H-furo[2,3-c]azepine hydrochloride The same method as in Example 3 was conducted using 7-methyl-5,6,7,8-tetrahydro-4H-furo[2,3-c]azepin-4-ol (Reference Example 19) instead of 6-methyl-4,5,6,7-tetrahydrothieno[2,3-c]pyridin-4-ol (Reference Example 6) and was conducted using 2-carbamoyl-1-fluorobenzene instead of 1,3-difluorobenzene to give the objective compound.
Colorless powder, MS spectrum: 287[M+H]$^+$

Example 252

4-(4-Methylcarbamoyl-2-chlorophenyloxy)-7-methyl-5,6,7,8-tetrahydro-4H-furo[2,3-c]azepine hydrochloride The same method as in Example 3 was conducted using 7-methyl-5,6,7,8-tetrahydro-4H-furo[2,3-c]azepin-4-ol (Reference Example 19) instead of 6-methyl-4,5,6,7-tetrahydrothieno[2,3-c]pyridin-4-ol (Reference Example 6) and was conducted using 4-methyl carbamoyl-2-chloro-1-fluorobenzene instead of 1,3-difluorobenzene to give the objective compound.
White powder, MS spectrum: 335[M+H]$^+$

Example 253

4-(4-Isopropylcarbamoyl-2-chlorophenyloxy)-7-methyl-5,6,7,8-tetrahydro-4H-furo[2,3-c]azepine hydrochloride The same method as in Example 3 was conducted using 7-methyl-5,6,7,8-tetrahydro-4H-furo[2,3-c]azepin-4-ol (Reference Example 19) instead of 6-methyl-4,5,6,7-tetrahydrothieno[2,3-c]pyridin-4-ol (Reference Example 6) and was conducted using 4-isopropyl carbamoyl-2-chloro-1-fluorobenzene instead of 1,3-difluorobenzene to give the objective compound.
White powder, MS spectrum: 363[M+H]$^+$

---

(Reference Example 19) instead of 6-methyl-4,5,6,7-tetrahydrothieno[2,3-c]pyridin-4-ol (Reference Example 6) and was conducted using 2-fluoro-5-carbamoylbenzotrifluoride instead of 1,3-difluorobenzene to give the objective compound.
Pale yellow powder, MS spectrum: 355[M+H]$^+$

Example 254

4-(2-Bromophenyloxy)-2,6-dimethyl-4,5,6,7-tetrahydrofuro[2,3-c]pyridine hydrochloride The same method as in Example 3 was conducted using 2,6-dimethyl-4,5,6,7-tetrahydrofuro[2,3-c]pyridin-4-ol (Reference Example 2) instead of 6-methyl-4,5,6,7-tetrahydrofuro[2,3-c]pyridin-4-ol (Reference Example 1) and was conducted using 2-bromo-1-fluorobenzene instead of 1,3-difluorobenzene to give the objective compound.

Pale yellow powder, MS spectrum: 322[M+H]$^+$

Example 255

4-(Benzothiophen-7-yloxy)-7-methyl-5,6,7,8-tetrahydro-4H-furo[2,3-c]azepine hydrochloride The same method as in Example 47 was conducted using 2-methyl-5,6,7,8-tetrahydro-4H-furo[2,3-c]azepin-4-ol (Reference Example 19) instead of 6-methyl-4,5,6,7-tetrahydrofuro[2,3-c]pyridin-4-ol (Reference Example 1) and was conducted using 7-hydroxybenzothiophene instead of 4-chloro-3-methylphenol to give the objective compound.

Pale yellow powder, MS spectrum: 300[M+H]$^+$

Example 256

4-(2-Methoxyphenyloxy)-7-methyl-5,6,7,8-tetrahydro-4H-furo[2,3-c]azepine hydrochloride The same method as in Example 3 was conducted using 7-methyl-5,6,7,8-tetrahydro-4H-furo[2,3-c]azepin-4-ol (Reference Example 19) instead of 6-methyl-4,5,6,7-tetrahydrothieno[2,3-c]pyridin-4-ol (Reference Example 6) and was conducted using 2-methoxy-1-fluorobenzene instead of 1,3-difluorobenzene to give the objective compound.

Pale yellow powder, MS spectrum: 274[M+H]$^+$

Example 257

4-(4-Dibutylcarbamoyl-2-chlorophenyloxy)-7-methyl-5,6,7,8-tetrahydro-4H-furo[2,3-c]azepine hydrochloride The same method as in Example 3 was conducted using 7-methyl-5,6,7,8-tetrahydro-4H-furo[2,3-c]azepin-4-ol (Reference Example 19) instead of 6-methyl-4,5,6,7-tetrahydrothieno[2,3-c]pyridin-4-ol (Reference Example 6) and was conducted using 4-dibutyl carbamoyl-2-chloro-1-fluorobenzene instead of 1,3-difluorobenzene to give the objective compound.

Pale yellow powder, MS spectrum: 433[M+H]$^+$

Example 258

4-(2-Trifluoromethoxyphenyloxy)-7-methyl-5,6,7,8-tetrahydro-4H-furo[2,3-c]azepine hydrochloride The same method as in Example 3 was conducted using 7-methyl-5,6,7,8-tetrahydro-4H-furo[2,3-c]azepin-4-ol (Reference Example 19) instead of 6-methyl-4,5,6,7-tetrahydrothieno[2,3-c]pyridin-4-ol (Reference Example 6) and was conducted using 1-fluoro-2-trifluoromethoxybenzene instead of 1,3-difluorobenzene to give the objective compound.

White powder, MS spectrum: 328[M+H]$^+$

Example 259

4-(Benzothiophen-4-yloxy)-2,6-dimethyl-4,5,6,7-tetrahydrofuro[2,3-c]pyridine hydrochloride The same method as in Example 47 was conducted using 2,6-dimethyl-4,5,6,7-tetrahydrofuro[2,3-c]pyridin-4-ol (Reference Example 2) instead of 6-methyl-4,5,6,7-tetrahydrofuro[2,3-c]pyridin-4-ol (Reference Example 1) and was conducted using 4-hydroxybenzothiophene instead of 4-chloro-3-methylphenol to give the objective compound.

White powder, MS spectrum: 300[M+H]$^+$

Example 260

4-(Benzofuran-4-yloxy)-2,6-dimethyl-4,5,6,7-tetrahydrofuro[2,3-c]pyridine hydrochloride The same method as in Example 47 was conducted using 2,6-dimethyl-4,5,6,7-tetrahydrofuro[2,3-c]pyridin-4-ol (Reference Example 2) instead of 6-methyl-4,5,6,7-tetrahydrofuro[2,3-c]pyridin-4-ol (Reference Example 1) and was conducted using 4-hydroxybenzofuran instead of 4-chloro-3-methylphenol to give the objective compound.

White powder, MS spectrum: 284[M+H]$^+$

Example 261

4-(Benzothiophen-4-yloxy)-6-methyl-4,5,6,7-tetrahydrofuro[2,3-c]pyridine hydrochloride The same method as in Example 47 was conducted using 4-hydroxybenzothiophene instead of 4-chloro-3-methylphenol to give the objective compound.

White powder, MS spectrum: 286[M+H]$^+$

Example 262

4-(Benzofuran-4-yloxy)-6-methyl-4,5,6,7-tetrahydrofuro[2,3-c]pyridine hydrochloride The same method as in Example 47 was conducted using 4-hydroxybenzofuran instead of 4-chloro-3-methylphenol to give the objective compound.

Pale yellow powder, MS spectrum: 270[M+H]$^+$

Example 263

4-(3-Methylcarbamoyl-2-chlorophenyloxy)-7-methyl-5,6,7,8-tetrahydro-4H-furo[2,3-c]azepine hydrochloride The same method as in Example 3 was conducted using 7-methyl-5,6,7,8-tetrahydro-4H-furo[2,3-c]azepin-4-ol (Reference Example 19) instead of 6-methyl-4,5,6,7-tetrahydrothieno[2,3-c]pyridin-4-ol (Reference Example 6) and was conducted using 3-methylcarbamoyl-2-chloro-1-fluorobenzene instead of 1,3-difluorobenzene to give the objective compound.

Pale yellow powder, MS spectrum: 335[M+H]$^+$

Example 264

4-(3-Dimethylcarbamoyl-2-chlorophenyloxy)-7-methyl-5,6,7,8-tetrahydro-4H-furo[2,3-c]azepine hydrochloride The same method as in Example 3 was conducted using 7-methyl-5,6,7,8-tetrahydro-4H-furo[2,3-c]azepin-4-ol (Reference Example 19) instead of 6-methyl-4,5,6,7-tetrahydrothieno[2,3-c]pyridin-4-ol (Reference Example 6) and was conducted using 3-dimethylcarbamoyl-2-chloro-1-fluorobenzene instead of 1,3-difluorobenzene to give the objective compound.

White powder, MS spectrum: 349[M+H]$^+$

Example 265

4-(3-Trifluoromethoxyphenyloxy)-7-methyl-5,6,7,8-tetrahydro-4H-furo[2,3-c]azepine hydrochloride The same method as in Example 3 was conducted using 7-methyl-5,6,7,8-tetrahydro-4H-furo[2,3-c]azepin-4-ol (Reference Example 19) instead of 6-methyl-4,5,6,7-tetrahydrothieno[2,3-c]pyridin-4-ol (Reference Example 6) and was conducted using 3-trifluoromethoxy-1-fluorobenzene instead of 1,3-difluorobenzene to give the objective compound.

White powder, MS spectrum: 328[M+H]$^+$

Example 266

4-(4-Acetylaminophenyloxy)-7-methyl-5,6,7,8-tetrahydro-4H-furo[2,3-c]azepine hydrochloride The same method as in Example 47 was conducted using 7-methyl-5,6,7,8-tetrahydro-4H-furo[2,3-c]azepin-4-ol (Reference Example 19) instead of 6-methyl-4,5,6,7-tetrahydrofuro[2,3-c]pyridin-4-ol (Reference Example 1) and was conducted using 4-acetylaminophenyloxy-1-phenol instead of 4-chloro-3-methylphenol to give the objective compound.

Pale yellow powder, MS spectrum: 301[M+H]$^+$

Example 267

4-(4-Acetylaminophenyloxy)-7-methyl-5,6,7,8-tetrahydro-4H-furo[2,3-c]azepine hydrochloride The same method as in Example 47 was conducted using 7-methyl-5,6,7,8-tetrahydro-4H-furo[2,3-c]azepin-4-ol (Reference Example 19) instead of 6-methyl-4,5,6,7-tetrahydrofuro[2,3-c]pyridin-4-ol (Reference Example 1) and was conducted using 3-acetylaminophenyloxy-1-phenol instead of 4-chloro-3-methylphenol to give the objective compound.

Pale yellow powder, MS spectrum: 301[M+H]$^+$

Example 268

4-(5-Fluorobenzothiophen-4-yloxy)-2,6-dimethyl-4,5,6,7-tetrahydrofuro[2,3-c]pyridine hydrochloride The same method as in Example 47 was conducted using 2,6-dimethyl-4,5,6,7-tetrahydrofuro[2,3-c]pyridin-4-ol (Reference Example 2) instead of 6-methyl-4,5,6,7-tetrahydrofuro[2,3-c]pyridin-4-ol (Reference Example 1) and was conducted using 5-fluoro-4-hydroxybenzothiophene instead of 4-chloro-3-methylphenol to give the objective compound.

White powder, MS spectrum: 318[M+H]$^+$

Example 269

4-(5-Fluorobenzothiophen-4-yloxy)-6-methyl-4,5,6,7-tetrahydrofuro[2,3-c]pyridine hydrochloride The same method as in Example 47 was conducted using 5-fluoro-4-hydroxybenzothiophene instead of 4-chloro-3-methylphenol to give the objective compound.

Pale yellow powder, MS spectrum: 304[M+H]$^+$

Example 270

4-(4-Carbamoyl-2-chlorophenyloxy)-7-(2,2,2-trifluoroethyl)-5,6,7,8-tetrahydro-4H-furo[2,3-c]azepine hydrochloride The same method as in Example 3 was conducted using 7-(2,2,2-trifluoroethyl)-5,6,7,8-tetrahydro-4H-furo[2,3-c]azepin-4-ol (Reference Example 38) instead of 6-methyl-4,5,6,7-tetrahydrothieno[2,3-c]pyridin-4-ol (Reference Example 6) and was conducted using 4-carbamoyl-2-chloro-1-fluorobenzene instead of 1,3-difluorobenzene to give the objective compound.

Yellow amorphous, MS spectrum: 389[M+H]$^+$

Example 271

4-(4-Trifluoromethoxyphenyloxy)-7-methyl-5,6,7,8-tetrahydro-4H-furo[2,3-c]azepine hydrochloride The same method as in Example 3 was conducted using 7-methyl-5,6,7,8-tetrahydro-4H-furo[2,3-c]azepin-4-ol (Reference Example 19) instead of 6-methyl-4,5,6,7-tetrahydrothieno[2,3-c]pyridin-4-ol (Reference Example 6) and was conducted using 4-trifluoromethoxy-1-fluorobenzene instead of 1,3-difluorobenzene to give the objective compound.

Pale yellow powder, MS spectrum: 328[M+H]$^+$

Example 272

4-(2,4-Difluorophenyloxy)-7-methyl-5,6,7,8-tetrahydro-4H-furo[2,3-c]azepine hydrochloride The same method as in Example 47 was conducted using 7-methyl-5,6,7,8-tetrahydro-4H-furo[2,3-c]azepin-4-ol (Reference Example 19) instead of 6-methyl-4,5,6,7-tetrahydrofuro[2,3-c]pyridin-4-ol (Reference Example 1) and was conducted using 2,4-difluorophenol instead of 4-chloro-3-methylphenol to give the objective compound.

Pale yellow powder, MS spectrum: 279[M+H]$^+$

Example 273

4-(2,3-Difluorophenyloxy)-7-methyl-5,6,7,8-tetrahydro-4H-furo[2,3-c]azepine hydrochloride The same method as in Example 47 was conducted using 7-methyl-5,6,7,8-tetrahydro-4H-furo[2,3-c]azepin-4-ol (Reference Example 19) instead of 6-methyl-4,5,6,7-tetrahydrofuro[2,3-c]pyridin-4-ol (Reference Example 1) and was conducted using 2,3-difluorophenol instead of 4-chloro-3-methylphenol to give the objective compound.

Pale yellow powder, MS spectrum: 279[M+H]$^+$

Example 274

4-(3,4-Difluorophenyloxy)-7-methyl-5,6,7,8-tetrahydro-4H-furo[2,3-c]azepine hydrochloride The same method as in Example 47 was conducted using 7-methyl-5,6,7,8-tetrahydro-4H-furo[2,3-c]azepin-4-ol (Reference Example 19) instead of 6-methyl-4,5,6,7-tetrahydrofuro[2,3-c]pyridin-4-ol (Reference Example 1) and was conducted using 3,4-difluorophenol instead of 4-chloro-3-methylphenol to give the objective compound.
White powder, MS spectrum: 279[M+H]$^+$

Example 275

4-(4-Carbamoyl-2-chlorophenyloxy)-7-cyclopropylmethyl-5,6,7,8-tetrahydro-4H-furo[2,3-c]azepine hydrochloride The same method as in Example 3 was conducted using 7-cyclopropylmethyl-5,6,7,8-tetrahydro-4H-furo[2,3-c]azepin-4-ol (Reference Example 39) instead of 6-methyl-4,5,6,7-tetrahydrothieno[2,3-c]pyridin-4-ol (Reference Example 6) and was conducted using 4-carbamoyl-2-chloro-1-fluorobenzene instead of 1,3-difluorobenzene to give the objective compound.
White powder, MS spectrum: 361[M+H]$^+$

Example 276

4-(2-Chloro-6-fluorophenyloxy)-7-methyl-5,6,7,8-tetrahydro-4H-furo[2,3-c]azepine hydrochloride The same method as in Example 47 was conducted using 7-methyl-5,6,7,8-tetrahydro-4H-furo[2,3-c]azepin-4-ol (Reference Example 19) instead of 6-methyl-4,5,6,7-tetrahydrofuro[2,3-c]pyridin-4-ol (Reference Example 1) and was conducted using 2-chloro-6-fluorophenol instead of 4-chloro-3-methylphenol to give the objective compound.
Pale yellow amorphous, MS spectrum: 296[M+H]$^+$

Example 277

4-(3-Bromo-2-chlorophenyloxy)-2-chloro-7-methyl-5,6,7,8-tetrahydro-4H-thieno[2,3-c]azepine hydrochloride The same method as in Example 3 was conducted using 2-chloro-7-methyl-5,6,7,8-tetrahydro-4H-thieno[2,3-c]azepin-4-ol (Reference Example 24) instead of 6-methyl-4,5,6,7-tetrahydrothieno[2,3-c]pyridin-4-ol (Reference Example 6) and was conducted using 3-bromo-2-chloro-1-fluorobenzene instead of 1,3-difluorobenzene to give the objective compound.
Pale yellow amorphous, MS spectrum: 408[M+H]$^+$

Example 278

4-(2,6-Dichlorophenyloxy)-7-methyl-5,6,7,8-tetrahydro-4H-furo[2,3-c]azepine hydrochloride The same method as in Example 3 was conducted using 7-methyl-5,6,7,8-tetrahydro-4H-furo[2,3-c]azepin-4-ol (Reference Example 19) instead of 6-methyl-4,5,6,7-tetrahydrothieno[2,3-c]pyridin-4-ol (Reference Example 6) and was conducted using 2,6-dichloro-1-fluorobenzene instead of 1,3-difluorobenzene to give the objective compound.
Pale yellow powder, MS spectrum: 312[M+H]$^+$

Example 279

4-(4-Carbamoyl-2-chlorophenyloxy)-2-chloro-7-methyl-5,6,7,8-tetrahydro-4H-thieno[2,3-c]azepine hydrochloride The same method as in Example 3 was conducted using 2-chloro-7-methyl-5,6,7,8-tetrahydro-4H-thieno[2,3-c]azepin-4-ol (Reference Example 24) instead of 6-methyl-4,5,6,7-tetrahydrothieno[2,3-c]pyridin-4-ol (Reference Example 6) and was conducted using 4-carbamoyl-2-chloro-1-fluorobenzene instead of 1,3-difluorobenzene to give the objective compound.
White powder, MS spectrum: 371[M+H]$^+$

Example 280

4-(3-Bromo-2-chlorophenyloxy)-7-(two-methoxy-1-ethyl)-5,6,7,8-tetrahydro-4H-furo[2,3-c]azepine hydrochloride The same method as in Example 3 was conducted using 7-(2-methoxy-1-ethyl)-5,6,7,8-tetrahydro-4H-furo[2,3-c]azepin-4-ol (Reference Example 40) instead of 6-methyl-4,5,6,7-tetrahydrothieno[2,3-c]pyridin-4-ol (Reference Example 6) and was conducted using 3-bromo-2-chloro-1-fluorobenzene instead of 1,3-difluorobenzene to give the objective compound.
White powder, MS spectrum: 400[M+H]$^+$

Example 281

4-(3-Bromo-2-chlorophenyloxy)-7-cyanomethyl-5,6,7,8-tetrahydro-4H-furo[2,3-c]azepine hydrochloride The same method as in Example 3 was conducted using 7-cyanomethyl-5,6,7,8-tetrahydro-4H-furo[2,3-c]azepin-4-ol (Reference Example 41) instead of 6-methyl-4,5,6,7-tetrahydrothieno[2,3-c]pyridin-4-ol (Reference Example 6) and was conducted using 3-bromo-2-chloro-1-fluorobenzene instead of 1,3-difluorobenzene to give the objective compound.
Brown liquid, MS spectrum: 381[M+H]$^+$

Example 282

4-(3-Bromo-2-chlorophenyloxy)-7-ethoxycarbonylmethyl-5,6,7,8-tetrahydro-4H-furo[2,3-c]azepine hydrochloride The same method as in Example 3 was conducted using 7-ethoxycarbonylmethyl-5,6,7,8-tetrahydro-4H-furo[2,3-c]azepin-4-ol (Reference Example 42) instead of 6-methyl-4,5,6,7-tetrahydrothieno[2,3-c]pyridin-4-ol (Reference Example 6) and was conducted using 3-bromo-2-chloro-1-fluorobenzene instead of 1,3-difluorobenzene to give the objective compound.
White powder, MS spectrum: 428[M+H]$^+$

Example 283

4-(3-Bromo-2-chlorophenyloxy)-7-(2-hydroxy-2-methyl-1-propyl)-5,6,7,8-tetrahydro-4H-furo[2,3-c]azepine hydrochloride The same method as in Example 3 was conducted using 7-(2-hydroxy-2-methyl-1-propyl)-5,6,7,8-tetrahydro-4H- furo[2,3-c]azepin-4-ol (Reference Example 43) instead of 6-methyl-4,5,6,7-tetrahydrothieno[2,3-c]pyridin-4-ol (Reference Example 6) and was conducted using 3-bromo-2-chloro-1-fluorobenzene instead of 1,3-difluorobenzene to give the objective compound.

Pale yellow liquid, MS spectrum: 414[M+H]$^+$

Example 284

4-(Naphthalen-1-yloxy)-2-methyl-5,6,7,8-tetrahydro-4H-furo[2,3-c]azepine hydrochloride The same method as in Example 3 was conducted using 2-methyl-5,6,7,8-tetrahydro-4H-furo[2,3-c]azepin-4-ol (Reference Example 44) instead of 6-methyl-4,5,6,7-tetrahydrothieno[2,3-c]pyridin-4-ol (Reference Example 6) and was conducted using 1-fluoronaphthalene instead of 1,3-difluorobenzene to give the objective compound.

Pale brown powder, MS spectrum: 294[M+H]$^+$

Example 285

4-(2-Bromophenyloxy)-5,6,7,8-tetrahydro-4H-furo[2,3-c]azepine hydrochloride

The same method as in Example 3 was conducted using 5,6,7,8-tetrahydro-4H-furo[2,3-c]azepin-4-ol (Reference Example 37) instead of 6-methyl-4,5,6,7-tetrahydrothieno[2,3-c]pyridin-4-ol (Reference Example 6) and was conducted using 2-bromo-1-fluorobenzene instead of 1,3-difluorobenzene to give the objective compound.

Brown amorphous, MS spectrum: 308[M+H]$^+$

Example 286

4-(3-Bromophenyloxy)-5,6,7,8-tetrahydro-4H-furo[2,3-c]azepine hydrochloride

The same method as in Example 3 was conducted using 5,6,7,8-tetrahydro-4H-furo[2,3-c]azepin-4-ol (Reference Example 37) instead of 6-methyl-4,5,6,7-tetrahydrothieno[2,3-c]pyridin-4-ol (Reference Example 6) and was conducted using 3-bromo-1-fluorobenzene instead of 1,3-difluorobenzene to give the objective compound.

Brown amorphous, MS spectrum: 308[M+H]$^+$

Example 287

4-(4-Cyanonaphthalen-1-yloxy)-5,6,7,8-tetrahydro-4H-furo[2,3-c]azepine hydrochloride The same method as in Example 3 was conducted using 5,6,7,8-tetrahydro-4H-furo[2,3-c]azepin-4-ol (Reference Example 37) instead of 6-methyl-4,5,6,7-tetrahydrothieno[2,3-c]pyridin-4-ol (Reference Example 6) and was conducted using 4-cyano-1-fluoronaphthalene instead of 1,3-difluorobenzene to give the objective compound.

Brown amorphous, MS spectrum: 305[M+H]$^+$

Example 288

4-(4-Bromonaphthalen-1-yloxy)-5,6,7,8-tetrahydro-4H-furo[2,3-c]azepine hydrochloride The same method as in Example 3 was conducted using 5,6,7,8-tetrahydro-4H-furo[2,3-c]azepin-4-ol (Reference Example 37) instead of 6-methyl-4,5,6,7-tetrahydrothieno[2,3-c]pyridin-4-ol (Reference Example 6) and was conducted using 1-bromo-4-fluoronaphthalene instead of 1,3-difluorobenzene to give the objective compound.

Pale yellow powder, MS spectrum: 358[M+H]$^+$

Example 289

4-(4-Carbamoylnaphthalen-1-yloxy)-5,6,7,8-tetrahydro-4H-furo[2,3-c]azepine hydrochloride The same method as in Example 3 was conducted using 5,6,7,8-tetrahydro-4H-furo[2,3-c]azepin-4-ol (Reference Example 37) instead of 6-methyl-4,5,6,7-tetrahydrothieno[2,3-c]pyridin-4-ol (Reference Example 6) and was conducted using 1-carbamoyl-4-fluoronaphthalene instead of 1,3-difluorobenzene to give the objective compound.

Pale yellow powder, MS spectrum: 323[M+H]$^+$

Example 290

4-(4-Bromonaphthalen-1-yloxy)-2-methyl-5,6,7,8-tetrahydro-4H-furo[2,3-c]azepine hydrochloride The same method as in Example 3 was conducted using 2-methyl-5,6,7,8-tetrahydro-4H-furo[2,3-c]azepin-4-ol (Reference Example 44) instead of 6-methyl-4,5,6,7-tetrahydrothieno[2,3-c]pyridin-4-ol (Reference Example 6) and was conducted using 1-bromo-4-fluoronaphthalene instead of 1,3-difluorobenzene to give the objective compound.

Pale yellow powder, MS spectrum: 372[M+H]$^+$

Example 291

4-(2,3-Dichlorophenyloxy)-2-methyl-5,6,7,8-tetrahydro-4H-furo[2,3-c]azepine hydrochloride The same method as in Example 3 was conducted using 2-methyl-5,6,7,8-tetrahydro-4H-furo[2,3-c]azepin-4-ol (Reference Example 44) instead of 6-methyl-4,5,6,7-tetrahydrothieno[2,3-c]pyridin-4-ol (Reference Example 6) and was conducted using 2,3-dichloro-1-fluorobenzene instead of 1,3-difluorobenzene to give the objective compound.

Brown powder, MS spectrum: 312[M+H]$^+$

Example 292

(+)-4-(3-Bromo-2,5-dichlorophenyloxy)-7-methyl-5,6,7,8-tetrahydro-4H-furo[2,3-c]azepine hydrochloride The same method as in Example 3 was conducted using (+)-7-methyl-5,6,7,8-tetrahydro-4H-furo[2,3-c]azepin-4-ol (Reference Example 52) instead of 6-methyl-4,5,6,7-tetrahydrothieno[2,3-c]pyridin-4-ol (Reference Example 6) and was conducted using 3-bromo-2,5-dichloro-1-fluorobenzene instead of 1,3-difluorobenzene to give the objective compound.

Pale yellow powder, MS spectrum: 392[M+H]$^+$, 99.0% ee
Specific rotation $[\alpha]_D$=+114.4° (25° C., c=1.00, MeOH)

Example 293

4-(2-Bromophenyloxy)-2-methyl-5,6,7,8-tetrahydro-4H-furo[2,3-c]azepine hydrochloride The same method as in Example 3 was conducted using 2-methyl-5,6,7,8-tetrahydro-4H-furo[2,3-c]azepin-4-ol (Reference Example 44) instead of 6-methyl-4,5,6,7-tetrahydrothieno[2,3-c]pyridin-4-ol (Reference Example 6) and was conducted using 2-bromo-1-fluorobenzene instead of 1,3-difluorobenzene to give the objective compound.
Pale yellow powder, MS spectrum: 322[M+H]$^+$ Example 294

4-(3-Bromophenyloxy)-2-methyl-5,6,7,8-tetrahydro-4H-furo[2,3-c]azepine hydrochloride The same method as in Example 3 was conducted using 2-methyl-5,6,7,8-tetrahydro-4H-furo[2,3-c]azepin-4-ol (Reference Example 44) instead of 6-methyl-4,5,6,7-tetrahydrothieno[2,3-c]pyridin-4-ol (Reference Example 6) and was conducted using 3-bromo-1-fluorobenzene instead of 1,3-difluorobenzene to give the objective compound.
Pale yellow powder, MS spectrum: 322[M+H]$^+$ Example 295

4-(4-Carbamoyl-2-chlorophenyloxy)-5,6,7,8-tetrahydro-4H-furo[2,3-c]azepine hydrochloride The same method as in Example 3 was conducted using 5,6,7,8-tetrahydro-4H-furo[2,3-c]azepin-4-ol (Reference Example 37) instead of 6-methyl-4,5,6,7-tetrahydrothieno[2,3-c]pyridin-4-ol (Reference Example 6) and was conducted using 4-carbamoyl-2-chloro-1-fluorobenzene instead of 1,3-difluorobenzene to give the objective compound.
Brown amorphous, MS spectrum: 307[M+H]$^+$ Example 296

4-(Benzothiophen-7-yloxy)-5,6,7,8-tetrahydro-4H-furo[2,3-c]azepine hydrochloride The same method as in Example 3 was conducted using 5,6,7,8-tetrahydro-4H-furo[2,3-c]azepin-4-ol (Reference Example 37) instead of 6-methyl-4,5,6,7-tetrahydrothieno[2,3-c]pyridin-4-ol (Reference Example 6) and was conducted using 7-fluorobenzothiophene instead of 1,3-difluorobenzene to give the objective compound.
Brown amorphous, MS spectrum: 286[M+H]$^+$ Example 297

4-[4-Bromo-2-(trifluoromethyl)phenyloxy]-5,6,7,8-tetrahydro-4H-furo[2,3-c]azepine hydrochloride The same method as in Example 3 was conducted using 5,6,7,8-tetrahydro-4H-furo[2,3-c]azepin-4-ol (Reference Example 37) instead of 6-methyl-4,5,6,7-tetrahydrothieno[2,3-c]pyridin-4-ol (Reference Example 6) and was conducted using 4-bromo-1-fluoro-2-benzotrifluoride instead of 1,3-difluorobenzene to give the objective compound.
Pale yellow powder, MS spectrum: 378[M+H]$^+$ Example 298

4-(4-Methylnaphthalen-1-yloxy)-2-methyl-5,6,7,8-tetrahydro-4H-furo[2,3-c]azepine hydrochloride The same method as in Example 3 was conducted using 2-methyl-5,6,7,8-tetrahydro-4H-furo[2,3-c]azepin-4-ol (Reference Example 44) instead of 6-methyl-4,5,6,7-tetrahydrothieno[2,3-c]pyridin-4-ol (Reference Example 6) and was conducted using 4-methyl-1-fluoronaphthalene instead of 1,3-difluorobenzene to give the objective compound.
Yellow powder, MS spectrum: 308[M+H]$^+$ Example 299

4-(2,3-Dichlorophenyloxy)-5,6,7,8-tetrahydro-4H-thieno[2,3-c]azepine hydrochloride The same method as in Example 3 was conducted using 5,6,7,8-tetrahydro-4H-thieno[2,3-c]azepin-4-ol (Reference Example 35) instead of 6-methyl-4,5,6,7-tetrahydrothieno[2,3-c]pyridin-4-ol (Reference Example 6) and was conducted using 2,3-dichloro-1-fluorobenzene instead of 1,3-difluorobenzene to give the objective compound.
Colorless powder, MS spectrum: 314[M+H]$^+$ Example 300

4-(3-Bromo-2-chlorophenyloxy)-5,6,7,8-tetrahydro-4H-thieno[2,3-c]azepine hydrochloride The same method as in Example 3 was conducted using 5,6,7,8-tetrahydro-4H-thieno[2,3-c]azepin-4-ol (Reference Example 35) instead of 6-methyl-4,5,6,7-tetrahydrothieno[2,3-c]pyridin-4-ol (Reference Example 6) and was conducted using 3-bromo-2-chloro-1-fluorobenzene instead of 1,3-difluorobenzene to give the objective compound.
Colorless powder, MS spectrum: 358[M+H]$^+$ Example 301

4-(Naphthalen-1-yloxy)-5,6,7,8-tetrahydro-4H-thieno[2,3-c]azepine hydrochloride

The same method as in Example 3 was conducted using 5,6,7,8-tetrahydro-4H-thieno[2,3-c]azepin-4-ol (Reference Example 35) instead of 6-methyl-4,5,6,7-tetrahydrothieno[2,3-c]pyridin-4-ol (Reference Example 6) and was conducted using 1-fluoronaphthalene instead of 1,3-difluorobenzene to give the objective compound.
Colorless powder, MS spectrum: 296[M+H]$^+$ Example 302

4-(4-Cyanonaphthalen-1-yloxy)-2-methyl-5,6,7,8-tetrahydro-4H-furo[2,3-c]azepine hydrochloride The same method as in Example 3 was conducted using 2-methyl-5,6,7,8-tetrahydro-4H-furo[2,3-c]azepin-4-ol (Reference Example 44) instead of 6-methyl-4,5,6,7-tetrahydrothieno[2,3-c]pyridin-4-ol (Reference Example 6) and was conducted using 4-cyano-1-fluoronaphthalene instead of 1,3-difluorobenzene to give the objective compound.
White powder, MS spectrum: 319[M+H]$^+$ Example 303

4-(3-Bromo-2,5-dichlorophenyloxy)-2-methyl-5,6,7,8-tetrahydro-4H-furo[2,3-c]azepine hydrochloride The same method as in Example 3 was conducted using 2-methyl-5,6,7,8-tetrahydro-4H-furo[2,3-c]azepin-4-ol (Reference Example 44) instead of 6-methyl-4,5,6,7-tetrahydrothieno[2,3-c]pyridin-4-ol (Reference Example 6) and was conducted using 3-bromo-2,5-dichloro-1-fluorobenzene instead of 1,3-difluorobenzene to give the objective compound.

Pale yellow powder, MS spectrum: 394[M+H]$^+$

Example 304

(+)-4-(5-Bromo-2-chlorophenyloxy)-7-methyl-5,6,7,8-tetrahydro-4H-furo[2,3-c]azepine hydrochloride The same method as in Example 3 was conducted using (+)-7-methyl-5,6,7,8-tetrahydro-4H-furo[2,3-c]azepin-4-ol (Reference Example 52) instead of 6-methyl-4,5,6,7-tetrahydrothieno[2,3-c]pyridin-4-ol (Reference Example 6) and was conducted using 5-bromo-2-chloro-1-fluorobenzene instead of 1,3-difluorobenzene to give the objective compound.

Pale yellow powder, MS spectrum: 358[M+H]$^+$, 99.0% ee

Specific rotation $[\alpha]_D$=+297.60 (25° C., c=1.00, MeOH)

Example 305

(+)-4-(4-Bromo-3-chlorophenyloxy)-7-methyl-5,6,7,8-tetrahydro-4H-furo[2,3-c]azepine hydrochloride The same method as in Example 3 was conducted using (+)-7-methyl-5,6,7,8-tetrahydro-4H-furo[2,3-c]azepin-4-ol (Reference Example 52) instead of 6-methyl-4,5,6,7-tetrahydrothieno[2,3-c]pyridin-4-ol (Reference Example 6) and was conducted using 4-bromo-3-chloro-1-fluorobenzene instead of 1,3-difluorobenzene to give the objective compound.

Pale yellow powder, MS spectrum: 358[M+H]$^+$, 99.0% ee

Specific rotation $[\alpha]_D$=+123.0° (25° C., c=1.00, MeOH)

Example 306

4-(Naphthalen-1-yloxy)-2-methyl-7-(pyridin-3-ylmethyl)-5,6,7,8-tetrahydro-4H-furo[2,3-c]azepine dihydrochloride Step 1

4-(Naphthalen-1-yloxy)-2-methyl-7-(3-pyridylcarbonyl)-5,6,7,8-tetrahydro-4H-furo[2,3-c]azepine 4-(Naphthalen-1-yloxy)-2-methyl-5,6,7,8-tetrahydro-4H-furo[2,3-c]azepine hydrochloride (50 mg) prepared in Example 284 and 47 mg of triethylamine were dissolved in 1 mL of methylene chloride, then 39 mg of 1-ethyl-3-(3-dimethyl-aminopropyl)carbodiimidehydrochloride (WSCD.HCl), 25 mg of nicotinic acid and 27 mg of 1-hydroxybenzotriazole were dropped thereinto successively and the mixture was stirred at room temperature for 6 hours. The reaction solution was poured over 2 mL of water and the mixture was subjected to extraction with methylene chloride. The organic layer was washed with water and a saturated solution of sodium chloride successively and dried over anhydrous magnesium sulfate and the solvent was evaporated therefrom in vacuo. The resulting residue was purified by silica gel column chromatography to give 70 mg of 4-(naphthalen-1-yloxy)-2-methyl-7-(3-pyridylcarbonyl)-5,6,7,8-tetrahydro-4H-furo[2,3-c]azepine MS spectrum: 398[M+H]$^+$.

Step 2

4-(Naphthalen-1-yloxy)-2-methyl-7-(pyridin-3-ylmethyl)-5,6,7,8-tetrahydro-4H-furo[2,3-c]azepine dihydrochloride Lithium aluminum hydride (7.6 mg) was slowly added, under ice-cooling with stirring, to a solution of 40 mg of 4-(naphthalen-1-yloxy)-2-methyl-7-(3-pyridylcarbonyl)-5,6,7,8-tetrahydro-4H-furo[2,3-c]azepine prepared in the step 1 in 2 mL of THF and the mixture was stirred at room temperature for 2 hours followed by heating to reflux for 3 hours more. The reaction solution was cooled, 2 mL of water was poured thereon and the mixture was subjected to extraction with ethyl acetate. The organic layer was washed with water and a saturated solution of sodium chloride successively and dried over anhydrous magnesium sulfate and the solvent was evaporated therefrom in vacuo. The resulting residue was purified by silica gel column chromatography to give 28 mg of a free substance.

The resulting free substance was dissolved in 3 mL of ethyl acetate, a one equivalent hydrochloric acid/ethyl acetate solution was dropped thereinto and the mixture was stirred for 30 minutes. This mixture was concentrated to give 27 mg of the objective compound.

White powder, MS spectrum: 383[M+H]$^+$

Example 307

4-(2,3-Dibromophenyloxy)-7-methyl-5,6,7,8-tetrahydro-4H-furo[2,3-c]azepine hydrochloride The same method as in Example 47 was conducted using 7-methyl-5,6,7,8-tetrahydro-4H-furo[2,3-c]azepin-4-ol (Reference Example 19) instead of 6-methyl-4,5,6,7-tetrahydrofuro[2,3-c]pyridin-4-ol (Reference Example 1) and was conducted using 2,3-dibromophenol instead of 4-chloro-3-methylphenol to give the objective compound.

White powder, MS spectrum: 400[M+H]$^+$

Example 308

4-(4-Benzyloxy-3-bromo-2-chlorophenyloxy)-5,6,7,8-tetrahydro-4H-furo[2,3-c]azepine hydrochloride The same method as in Example 3 was conducted using 5,6,7,8-tetrahydro-4H-furo[2,3-c]azepin-4-ol (Reference Example 37) instead of 6-methyl-4,5,6,7-tetrahydrothieno[2,3-c]pyridin-4-ol (Reference Example 6) and was conducted using 4-benzyloxy-3-bromo-2-chloro-1-fluorobenzene instead of 1,3-difluorobenzene to give the objective compound.

Pale yellow powder, MS spectrum: 448[M+H]$^+$

Example 309

4-(3-Bromo-2-chlorophenyloxy)-7-(2-dimethylaminoacetyl)-2-methyl-5,6,7,8-tetrahydro-4H-furo[2,3-c]azepine hydrochloride The same method as in Example 306 (step 1) was conducted using 4-(bromo-2-chlorophenyloxy)-2-methyl-5,6,7,8-tetrahydro-4H-furo[2,3-c]azepine hydrochloride (Reference Example 209) instead of 4-(naphthalen-1-yloxy)-2- methyl-5,6,7,8-tetrahydro-4H-furo[2,3-c]azepine hydrochloride (Reference Example 284) to give the objective compound.

Brown powder, MS spectrum: 441[M+H]$^+$

Example 310

4-(3-Bromo-2-chlorophenyloxy)-7-{2-(dimethylamino)ethyl}-2-methyl-5,6,7,8-tetrahydro-4H-furo[2,3-c]azepine dihydrochloride The same method as in Example 306 (step 2) was conducted using 4-(3-bromo-2-chlorophenyloxy)-7-(2-dimethylaminoacetyl)-2-methyl-5,6,7,8-tetrahydro-4H-furo[2,3-c]azepine (Reference Example 309) instead of 4-(naphthalen-1-yloxy)-2-methyl-5,6,7,8-tetrahydro-4H-furo[2,3-c]azepine to give the objective compound.

Brown powder, MS spectrum: 427[M+H]$^+$

Example 311

4-(Naphthalen-1-yloxy)-7-{2-(dimethylamino)ethyl}-2-methyl-5,6,7,8-tetrahydro-4H-furo[2,3-c]azepine dihydrochloride The same method as in Example 306 was conducted using N,N-dimethylglycine instead of nicotinic acid to give the objective compound.

Brown powder, MS spectrum: 365[M+H]$^+$

Example 312

7-(3,4-Dichlorophenyloxy)-2-methyl-4,5,6,7-tetrahydrothieno[3,2-c]pyridine

The same method as in Example 1 was conducted using 2-methyl-4,5,6,7-tetrahydrothieno[3,2-c]pyridin-7-ol (Reference Example 30) instead of 6-methyl-4,5,6,7-tetrahydrothieno[2,3-c]pyridin-4-ol (Reference Example 6) and was conducted using 3,4-dichloro-1-fluorobenzene instead of 1-fluoronaphthalene to give the objective compound.

Brown powder, MS spectrum: 314[M+H]$^+$

Example 313

7-(3-Bromo-2-chlorophenyloxy)-2-methyl-4,5,6,7-tetrahydrothieno[3,2-c]pyridine

The same method as in Example 1 was conducted using 2-methyl-4,5,6,7-tetrahydrothieno[3,2-c]pyridin-7-ol (Reference Example 30) instead of 6-methyl-4,5,6,7-tetrahydrothieno[2,3-c]pyridin-4-ol (Reference Example 6) and was conducted using 3-bromo-2-chloro-1-fluorobenzene instead of 1-fluoronaphthalene to give the objective compound.

Brown powder, MS spectrum: 358[M+H]$^+$

Example 314

7-(2-Bromophenyloxy)-2-methyl-4,5,6,7-tetrahydrothieno[3,2-c]pyridine

The same method as in Example 1 was conducted using 2-methyl-4,5,6,7-tetrahydrothieno[3,2-c]pyridin-7-ol (Reference Example 30) instead of 6-methyl-4,5,6,7-tetrahydrothieno[2,3-c]pyridin-4-ol (Reference Example 6) and was conducted using 2-bromo-1-fluorobenzene instead of 1-fluoronaphthalene to give the objective compound.

Brown powder, MS spectrum: 324[M+H]$^+$

Example 315

7-(4-Carbamoyl-2-chlorophenyloxy)-2-methyl-4,5,6,7-tetrahydrothieno[3,2-c]pyridine The same method as in Example 1 was conducted using 2-methyl-4,5,6,7-tetrahydrothieno[3,2-c]pyridin-7-ol (Reference Example 30) instead of 6-methyl-4,5,6,7-tetrahydrothieno[2,3-c]pyridin-4-ol (Reference Example 6) and was conducted using 4-carbamoyl-2-chloro-1-fluorobenzene instead of 1-fluoronaphthalene to give the objective compound.

Brown powder, MS spectrum: 322[M+H]$^+$

Example 316

7-(Naphthalen-1-yloxy)-2-methyl-4,5,6,7-tetrahydrothieno[3,2-c]pyridine

The same method as in Example 1 was conducted using 2-methyl-4,5,6,7-tetrahydrothieno[3,2-c]pyridin-7-ol (Reference Example 30) instead of 6-methyl-4,5,6,7-tetrahydrothieno[2,3-c]pyridin-4-ol (Reference Example 6), and the objective compound was prepared.

Brown powder, MS spectrum: 295[M+H]$^+$

Example 317

7-(4-Cyanonaphthalen-1-yloxy)-2-methyl-4,5,6,7-tetrahydrothieno[3,2-c]pyridine

The same method as in Example 1 was conducted using 2-methyl-4,5,6,7-tetrahydrothieno[3,2-c]pyridin-7-ol (Reference Example 30) instead of 6-methyl-4,5,6,7-tetrahydrothieno[2,3-c]pyridin-4-ol (Reference Example 6) and was conducted using 4-cyano-1-fluoronaphthalene instead of 1-fluoronaphthalene to give the objective compound.

Brown powder, MS spectrum: 320[M+H]$^+$

Example 318

7-(3,4-Dichlorophenyloxy)-2,5-dimethyl-4,5,6,7-tetrahydrothieno[3,2-c]pyridine

The same method as in Example 1 was conducted using 2,5-dimethyl-4,5,6,7-tetrahydrothieno[3,2-c]pyridin-7-ol (Reference Example 31) instead of 6-methyl-4,5,6,7-tetrahydrothieno[2,3-c]pyridin-4-ol (Reference Example 6) and was conducted using 3,4-dichloro-1-fluorobenzene instead of 1-fluoronaphthalene to give the objective compound.

Brown powder, MS spectrum: 328[M+H]$^+$

Example 319

7-(3-Bromo-2-chlorophenyloxy)-2,5-dimethyl-4,5,6,7-tetrahydrothieno[3,2-c]pyridine The same method as in Example 1 was conducted using 2,5-dimethyl-4,5,6,7-tetrahydrothieno[3,2-c]pyridin-7-ol (Reference Example 31) instead of 6-methyl-4,5,6,7-tetrahydrothieno[2,3-c]pyridin-4-ol (Reference Example 6) and was conducted using 3-bromo-2-chloro-1-fluorobenzene instead of 1-fluoronaphthalene to give the objective compound.

Brown powder, MS spectrum: 372[M+H]$^+$

Example 320

7-(2-Bromophenyloxy)-2,5-dimethyl-4,5,6,7-tetrahydrothieno[3,2-c]pyridine

The same method as in Example 1 was conducted using 2,5-dimethyl-4,5,6,7-tetrahydrothieno[3,2-c]pyridin-7-ol (Reference Example 31) instead of 6-methyl-4,5,6,7-tetrahydrothieno[2,3-c]pyridin-4-ol (Reference Example 6) and was conducted using 2-bromo-1-fluorobenzene instead of 1-fluoronaphthalene to give the objective compound.

Brown powder, MS spectrum: 338[M+H]$^+$

Example 321

7-(4-Carbamoyl-2-chlorophenyloxy)-2,5-dimethyl-4,5,6,7-tetrahydrothieno[3,2-c]pyridine The same method as in Example 1 was conducted using 2,5-dimethyl-4,5,6,7-tetrahydrothieno[3,2-c]pyridin-7-ol (Reference Example 31) instead of 6-methyl-4,5,6,7-tetrahydrothieno[2,3-c]pyridin-4-ol (Reference Example 6) and was conducted using 4-carbamoyl-2-chloro-1-fluorobenzene instead of 1-fluoronaphthalene to give the objective compound.

Brown powder, MS spectrum: 336[M+H]$^+$

Example 322

7-(Naphthalen-1-yloxy)-2,5-dimethyl-4,5,6,7-tetrahydrothieno[3,2-c]pyridine

The same method as in Example 1 was conducted using 2,5-dimethyl-4,5,6,7-tetrahydrothieno[3,2-c]pyridin-7-ol (Reference Example 31) instead of 6-methyl-4,5,6,7-tetrahydrothieno[2,3-c]pyridin-4-ol (Reference Example 6) to give the objective compound.

Brown powder, MS spectrum: 309[M+H]$^+$

Example 323

7-(4-Cyanonaphthalen-1-yloxy)-2,5-dimethyl-4,5,6,7-tetrahydrothieno[3,2-c]pyridine The same method as in Example 1 was conducted using 2,5-dimethyl-4,5,6,7-tetrahydrothieno[3,2-c]pyridin-7-ol (Reference Example 31) instead of 6-methyl-4,5,6,7-tetrahydrothieno[2,3-c]pyridin-4-ol (Reference Example 6) and was conducted using 4-cyano-1-fluoronaphthalene instead of 1-fluoronaphthalene to give the objective compound.

Brown powder, MS spectrum: 334[M+H]$^+$

Example 324

7-(3,4-Dichlorophenyloxy)-5-ethyl-2-methyl-4,5,6,7-tetrahydrothieno[3,2-c]pyridine The same method as in Example 1 was conducted using 5-ethyl-2-methyl-4,5,6,7-tetrahydrothieno[3,2-c]pyridin-7-ol (Reference Example 32) instead of 6-methyl-4,5,6,7-tetrahydrothieno[2,3-c]pyridin-4-ol (Reference Example 6) and was conducted using 3,4-dichloro-1-fluorobenzene instead of 1-fluoronaphthalene to give the objective compound.

Brown powder, MS spectrum: 342[M+H]$^+$

Example 325

7-(3-Bromo-2-chlorophenyloxy)-5-ethyl-2-methyl-4,5,6,7-tetrahydrothieno[3,2-c]pyridine The same method as in Example 1 was conducted using 5-ethyl-2-methyl-4,5,6,7-tetrahydrothieno[3,2-c]pyridin-7-ol (Reference Example 32) instead of 6-methyl-4,5,6,7-tetrahydrothieno[2,3-c]pyridin-4-ol (Reference Example 6) and was conducted using 3-bromo-2-chloro-1-fluorobenzene instead of 1-fluoronaphthalene to give the objective compound.

Brown powder, MS spectrum: 386[M+H]$^+$

Example 326

7-(2-Bromophenyloxy)-5-ethyl-2-methyl-4,5,6,7-tetrahydrothieno[3,2-c]pyridine

The same method as in Example 1 was conducted using 5-ethyl-2-methyl-4,5,6,7-tetrahydrothieno[3,2-c]pyridin-7-ol (Reference Example 32) instead of 6-methyl-4,5,6,7-tetrahydrothieno[2,3-c]pyridin-4-ol (Reference Example 6) and was conducted using 2-bromo-1-fluorobenzene instead of 1-fluoronaphthalene to give the objective compound.

Brown powder, MS spectrum: 352[M+H]$^+$

Example 327

7-(4-Carbamoyl-2-chlorophenyloxy)-5-ethyl-2-methyl-4,5,6,7-tetrahydrothieno[3,2-c]pyridine The same method as in Example 1 was conducted using 5-ethyl-2-methyl-4,5,6,7-tetrahydrothieno[3,2-c]pyridin-7-ol (Reference Example 32) instead of 6-methyl-4,5,6,7-tetrahydrothieno[2,3-c]pyridin-4-ol (Reference Example 6) and was conducted using 4-carbamoyl-2-chloro-1-fluorobenzene instead of 1-fluoronaphthalene to give the objective compound.

Brown powder, MS spectrum: 350[M+H]$^+$

Example 328

7-(Naphthalen-1-yloxy)-5-ethyl-2-methyl-4,5,6,7-tetrahydrothieno[3,2-c]pyridine

The same method as in Example 1 was conducted using 5-ethyl-2-methyl-4,5,6,7-tetrahydrothieno[3,2-c]pyridin-7-ol (Reference Example 32) instead of 6-methyl-4,5,6,7-tetrahydrothieno[2,3-c]pyridin-4-ol (Reference Example 6) to give the objective compound.

Brown powder, MS spectrum: 323[M+H]$^+$

Example 329

7-(4-Cyanonaphthalen-1-yloxy)-5-ethyl-2-methyl-4,5,6,7-tetrahydrothieno[3,2-c]pyridine The same method as in Example 1 was conducted using 5-ethyl-2-methyl-4,5,6,7-tetrahydrothieno[3,2-c]pyridin-7-ol (Reference Example 32) instead of 6-methyl-4,5,6,7-tetrahydrothieno[2,3-c]pyridin-4-ol (Reference Example 6) and was conducted using 4-cyano-1-fluoronaphthalene instead of 1-fluoronaphthalene to give the objective compound.

Brown powder, MS spectrum: 348[M+H]$^+$

Example 330

8-(3,4-Dichlorophenyloxy)-2,5-dimethyl-5,6,7,8-tetrahydro-4H-thieno[3,2-c]azepine

The same method as in Example 1 was conducted using 2,5-dimethyl-5,6,7,8-tetrahydro-4H-thieno[3,2-c]azepin-4-ol (Reference Example 36) instead of 6-methyl-4,5,6,7-tetrahydrothieno[2,3-c]pyridin-4-ol (Reference Example 6) and was conducted using 3,4-dichloro-1-fluorobenzene instead of 1-fluoronaphthalene to give the objective compound.
Brown powder, MS spectrum: 342[M+H]$^+$

Example 331

8-(3-Bromo-2-chlorophenyloxy)-2,5-dimethyl-5,6,7,8-tetrahydro-4H-thieno[3,2-c]azepine

The same method as in Example 1 was conducted using 2,5-dimethyl-5,6,7,8-tetrahydro-4H-thieno[3,2-c]azepin-4-ol (Reference Example 36) instead of 6 methyl-4,5,6,7-tetrahydrothieno[2,3-c]pyridin-4-ol (Reference Example 6) and was conducted using 3-bromo-2-chloro-1-fluorobenzene instead of 1-fluoronaphthalene to give the objective compound.
Brown powder, MS spectrum: 386[M+H]$^+$

Example 332

8-(2-Bromophenyloxy)-2,5-dimethyl-5,6,7,8-tetrahydro-4H-thieno[3,2-c]azepine

The same method as in Example 1 was conducted using 2,5-dimethyl-5,6,7,8-tetrahydro-4H-thieno[3,2-c]azepin-4-ol (Reference Example 36) instead of 6-methyl-4,5,6,7-tetrahydrothieno[2,3-c]pyridin-4-ol (Reference Example 6) and was conducted using 2-bromo-1-fluorobenzene instead of 1-fluoronaphthalene to give the objective compound.
Brown powder, MS spectrum: 352[M+H]$^+$

Example 333

8-(4-Carbamoyl-2-chlorophenyloxy)-2,5-dimethyl-5,6,7,8-tetrahydro-4H-thieno[3,2-c]azepine

The same method as in Example 1 was conducted using 2,5-dimethyl-5,6,7,8-tetrahydro-4H-thieno[3,2-c]azepin-4-ol (Reference Example 36) instead of 6-methyl-4,5,6,7-tetrahydrothieno[2,3-c]pyridin-4-ol (Reference Example 6) and was conducted using 4-carbamoyl-2-chloro-1-fluorobenzene instead of 1-fluoronaphthalene to give the objective compound.
Brown powder, MS spectrum: 350[M+H]$^+$

Example 334

8-(Naphthalen-1-yloxy)-2,5-dimethyl-5,6,7,8-tetrahydro-4H-thieno[3,2-c]azepine

The same method as in Example 1 was conducted using 2,5-dimethyl-5,6,7,8-tetrahydro-4H-thieno[3,2-c]azepin-4-ol (Reference Example 36) instead of 6-methyl-4,5,6,7-tetrahydrothieno[2,3-c]pyridin-4-ol (Reference Example 6) to give the objective compound.
Brown powder, MS spectrum: 323[M+H]$^+$

Example 335

8-(4-Cyanonaphthalen-1-yloxy)-2,5-dimethyl-5,6,7,8-tetrahydro-4H-thieno[3,2-c]azepine

The same method as in Example 1 was conducted using 2,5-dimethyl-5,6,7,8-tetrahydro-4H-thieno[3,2-c]azepin-4-ol (Reference Example 36) instead of 6-methyl-4,5,6,7-tetrahydrothieno[2,3-c]pyridin-4-ol (Reference Example 6) and was conducted using 4-cyano-1-fluoronaphthalene instead of 1-fluoronaphthalene to give the objective compound.
Brown powder, MS spectrum: 348[M+H]$^+$

Example 336

8-(3,4-Dichlorophenyloxy)-5,6,7,8-tetrahydro-4H-thieno[3,2-d]azepine

The same method as in Example 1 was conducted using 5,6,7,8-tetrahydro-4H-thieno[3,2-d]azepin-4-ol (Reference Example 46) instead of 6-methyl-4,5,6,7-tetrahydrothieno[2,3-c]pyridin-4-ol (Reference Example 6) and was conducted using 3,4-dichloro-1-fluorobenzene instead of 1-fluoronaphthalene to give the objective compound.
Brown powder, MS spectrum: 314[M+H]$^+$

Example 337

8-(3-Bromo-2-chlorophenyloxy)-5,6,7,8-tetrahydro-4H-thieno[3,2-d]azepine

The same method as in Example 1 was conducted using 5,6,7,8-tetrahydro-4H-thieno[3,2-d]azepin-4-ol (Reference Example 46) instead of 6-methyl-4,5,6,7-tetrahydrothieno[2,3-c]pyridin-4-ol (Reference Example 6) and was conducted using 3-bromo-2-chloro-1-fluorobenzene instead of 1-fluoronaphthalene to give the objective compound.
Brown powder, MS spectrum: 358[M+H]$^+$

Example 338

8-(2-Bromophenyloxy)-5,6,7,8-tetrahydro-4H-thieno[3,2-d]azepine

The same method as in Example 1 was conducted using 5,6,7,8-tetrahydro-4H-thieno[3,2-d]azepin-4-ol (Reference Example 46) instead of 6-methyl-4,5,6,7-tetrahydrothieno[2,3-c]pyridin-4-ol (Reference Example 6) and was conducted using 2-bromo-1-fluorobenzene instead of 1-fluoronaphthalene to give the objective compound.
Brown powder, MS spectrum: 324[M+H]$^+$

Example 339

8-(4-Carbamoyl-2-chlorophenyloxy)-5,6,7,8-tetrahydro-4H-thieno[3,2-d]azepine

The same method as in Example 1 was conducted using 5,6,7,8-tetrahydro-4H-thieno[3,2-d]azepin-4-ol (Reference Example 46) instead of 6-methyl-4,5,6,7-tetrahydrothieno[2,3-c]pyridin-4-ol (Reference Example 6) and was conducted using 4-carbamoyl-2-chloro-1-fluorobenzene instead of 1-fluoronaphthalene to give the objective compound.
Brown powder, MS spectrum: 322[M+H]$^+$

Example 340

8-(Naphthalen-1-yloxy)-5,6,7,8-tetrahydro-4H-thieno[3,2-d]azepine

The same method as in Example 1 was conducted using 5,6,7,8-tetrahydro-4H-thieno[3,2-d]azepin-4-ol (Reference Example 46) instead of 6-methyl-4,5,6,7-tetrahydrothieno[2,3-c]pyridin-4-ol (Reference Example 6) to give the objective compound.

Brown powder, MS spectrum: 295[M+H]$^+$

Example 341

8-(4-Cyanonaphthalen-1-yloxy)-5,6,7,8-tetrahydro-4H-thieno[3,2-d]azepine hydrochloride The same method as in Example 3 was conducted using 5,6,7,8-tetrahydro-4H-thieno[3,2-d]azepin-4-ol (Reference Example 46) instead of 6-methyl-4,5,6,7-tetrahydrothieno[2,3-c]pyridin-4-ol (Reference Example 6) and was conducted using 4-cyano-1-fluoronaphthalene instead of 1,3-difluorobenzene to give the objective compound.

Brown powder, MS spectrum: 321[M+H]$^+$

Example 342

8-(3,4-Dichlorophenyloxy)-6-methyl-5,6,7,8-tetrahydro-4H-thieno[3,2-d]azepine The same method as in Example 1 was conducted using 6-methyl-5,6,7,8-tetrahydro-4H-thieno[3,2-d]azepin-4-ol (Reference Example 47) instead of 6-methyl-4,5,6,7-tetrahydrothieno[2,3-c]pyridin-4-ol (Reference Example 6) and was conducted using 3,4-dichloro-1-fluorobenzene instead of 1-fluoronaphthalene to give the objective compound.

Brown powder, MS spectrum: 328[M+H]$^+$

Example 343

8-(3-Bromo-2-chlorophenyloxy)-6-methyl-5,6,7,8-tetrahydro-4H-thieno[3,2-d]azepine The same method as in Example 1 was conducted using 6-methyl-5,6,7,8-tetrahydro-4H-thieno[3,2-d]azepin-4-ol (Reference Example 47) instead of 6-methyl-4,5,6,7-tetrahydrothieno[2,3-c]pyridin-4-ol (Reference Example 6) and was conducted using 3-bromo-2-chloro-1-fluorobenzene instead of 1-fluoronaphthalene to give the objective compound.

Brown powder, MS spectrum: 372[M+H]$^+$

Example 344

8-(2-Bromophenyloxy)-6-methyl-5,6,7,8-tetrahydro-4H-thieno[3,2-d]azepine

The same method as in Example 1 was conducted using 6-methyl-5,6,7,8-tetrahydro-4H-thieno[3,2-d]azepin-4-ol (Reference Example 47) instead of 6-methyl-4,5,6,7-tetrahydrothieno[2,3-c]pyridin-4-ol (Reference Example 6) and was conducted using 2-bromo-1-fluorobenzene instead of 1-fluoronaphthalene to give the objective compound.

Brown powder, MS spectrum: 338[M+H]$^+$

Example 345

8-(4-Carbamoyl-2-chlorophenyloxy)-6-methyl-5,6,7,8-tetrahydro-4H-thieno[3,2-d]azepine The same method as in Example 1 was conducted using 6-methyl-5,6,7,8-tetrahydro-4H-thieno[3,2-d]azepin-4-ol (Reference Example 47) instead of 6-methyl-4,5,6,7-tetrahydrothieno[2,3-c]pyridin-4-ol (Reference Example 6) and was conducted using 4-carbamoyl-2-chloro-1-fluorobenzene instead of 1-fluoronaphthalene to give the objective compound.

Brown powder, MS spectrum: 336[M+H]$^+$

Example 346

8-(Naphthalen-1-yloxy)-6-methyl-5,6,7,8-tetrahydro-4H-thieno[3,2-d]azepine

The same method as in Example 1 was conducted using 6-methyl-5,6,7,8-tetrahydro-4H-thieno[3,2-d]azepin-4-ol (Reference Example 47) instead of 6-methyl-4,5,6,7-tetrahydrothieno[2,3-c]pyridin-4-ol (Reference Example 6) to give the objective compound.

Brown powder, MS spectrum: 309[M+H]$^+$

Example 347

8-(4-Cyanonaphthalen-1-yloxy)-6-methyl-5,6,7,8-tetrahydro-4H-thieno[3,2-d]azepine The same method as in Example 1 was conducted using 6-methyl-5,6,7,8-tetrahydro-4H-thieno[3,2-d]azepin-4-ol (Reference Example 47) instead of 6-methyl-4,5,6,7-tetrahydrothieno[2,3-c]pyridin-4-ol (Reference Example 6) and was conducted using 4-cyano-1-fluoronaphthalene instead of 1-fluoronaphthalene to give the objective compound.

Brown powder, MS spectrum: 334[M+H]$^+$

Example 348

8-(3,4-Dichlorophenyloxy)-6-ethyl-5,6,7,8-tetrahydro-4H-thieno[3,2-d]azepine The same method as in Example 1 was conducted using 6-ethyl-5,6,7,8-tetrahydro-4H-thieno[3,2-d]azepin-4-ol (Reference Example 48) instead of 6-methyl-4,5,6,7-tetrahydrothieno[2,3-c]pyridin-4-ol (Reference Example 6) and was conducted using 3,4-dichloro-1-fluorobenzene instead of 1-fluoronaphthalene to give the objective compound.

Brown powder, MS spectrum: 342[M+H]$^+$

Example 349

8-(3-Bromo-2-chlorophenyloxy)-6-ethyl-5,6,7,8-tetrahydro-4H-thieno[3,2-d]azepine The same method as in Example 1 was conducted using 6-ethyl-5,6,7,8-tetrahydro-4H-thieno[3,2-d]azepin-4-ol (Reference Example 48) instead of 6-methyl-4,5,6,7-tetrahydrothieno[2,3-c]pyridin-4-ol (Reference Example 6) and was conducted using 3-bromo-2-chloro-1-fluorobenzene instead of 1-fluoronaphthalene to give the objective compound.

Brown powder, MS spectrum: 386[M+H]$^+$

Example 350

8-(2-Bromophenyloxy)-6-ethyl-5,6,7,8-tetrahydro-4H-thieno[3,2-d]azepine

The same method as in Example 1 was conducted using 6-ethyl-5,6,7,8-tetrahydro-4H-thieno[3,2-d]azepin-4-ol (Reference Example 48) instead of 6-methyl-4,5,6,7-tetrahydrothieno[2,3-c]pyridin-4-ol (Reference Example 6) and was conducted using 2-bromo-1-fluorobenzene instead of 1-fluoronaphthalene to give the objective compound.

Brown powder, MS spectrum: 352[M+H]$^+$

Example 351

8-(4-Carbamoyl-2-chlorophenyloxy)-6-ethyl-5,6,7,8-tetrahydro-4H-thieno[3,2-d]azepine The same method as in Example 1 was conducted using 6-ethyl-5,6,7,8-tetrahydro-4H-thieno[3,2-d]azepin-4-ol (Reference Example 48) instead of 6-methyl-4,5,6,7-tetrahydrothieno[2,3-c]pyridin-4-ol (Reference Example 6) and was conducted using 4-carbamoyl-2-chloro-1-fluorobenzene instead of 1-fluoronaphthalene to give the objective compound.

Brown powder, MS spectrum: 351[M+H]$^+$

Example 352

8-(Naphthalen-1-yloxy)-6-ethyl-5,6,7,8-tetrahydro-4H-thieno[3,2-d]azepine

The same method as in Example 1 was conducted using 6-ethyl-5,6,7,8-tetrahydro-4H-thieno[3,2-d]azepin-4-ol (Reference Example 48) instead of 6-methyl-4,5,6,7-tetrahydrothieno[2,3-c]pyridin-4-ol (Reference Example 6) to give the objective compound.

Brown powder, MS spectrum: 324[M+H]$^+$

Example 353

8-(4-Cyanonaphthalen-1-yloxy)-6-ethyl-5,6,7,8-tetrahydro-4H-thieno[3,2-d]azepine The same method as in Example 1 was conducted using 6-ethyl-5,6,7,8-tetrahydro-4H-thieno[3,2-d]azepin-4-ol (Reference Example 48) instead of 6-methyl-4,5,6,7-tetrahydrothieno[2,3-c]pyridin-4-ol (Reference Example 6) and was conducted using 4-cyano-1-fluoronaphthalene instead of 1-fluoronaphthalene to give the objective compound.

Brown powder, MS spectrum: 349[M+H]$^+$

Example 354

4-(3,4-Dichlorophenyloxy)-2,7-dimethyl-5,6,7,8-tetrahydro-4H-thieno[2,3-c]azepine The same method as in Example 1 was conducted using 2,7-dimethyl-5,6,7,8-tetrahydro-4H-thieno[2,3-c]azepin-4-ol (Reference Example 23) instead of 6-methyl-4,5,6,7-tetrahydrothieno[2,3-c]pyridin-4-ol (Reference Example 6) and was conducted using 3,4-dichloro-1-fluorobenzene instead of 1-fluoronaphthalene to give the objective compound.

Brown powder, MS spectrum: 342[M+H]$^+$

Example 355

4-(3-Bromo-2-chlorophenyloxy)-2,7-dimethyl-5,6,7,8-tetrahydro-4H-thieno[2,3-c]azepine The same method as in Example 1 was conducted using 2,7-dimethyl-5,6,7,8-tetrahydro-4H-thieno[2,3-c]azepin-4-ol (Reference Example 23) instead of 6-methyl-4,5,6,7-tetrahydrothieno[2,3-c]pyridin-4-ol (Reference Example 6) and was conducted using 3-bromo-2-chloro-1-fluorobenzene instead of 1-fluoronaphthalene to give the objective compound.

Brown powder, MS spectrum: 386[M+H]$^+$

Example 356

4-(2-Bromophenyloxy)-2,7-dimethyl-5,6,7,8-tetrahydro-4H-thieno[2,3-c]azepine The same method as in Example 1 was conducted using 2,7-dimethyl-5,6,7,8-tetrahydro-4H-thieno[2,3-c]azepin-4-ol (Reference Example 23) instead of 6-methyl-4,5,6,7-tetrahydrothieno[2,3-c]pyridin-4-ol (Reference Example 6) and was conducted using 2-bromo-1-fluorobenzene instead of 1-fluoronaphthalene to give the objective compound.

Brown powder, MS spectrum: 352[M+H]$^+$

Example 357

4-(4-Carbamoyl-2-chlorophenyloxy)-2,7-dimethyl-5,6,7,8-tetrahydro-4H-thieno[2,3-c]azepine The same method as in Example 1 was conducted using 2,7-dimethyl-5,6,7,8-tetrahydro-4H-thieno[2,3-c]azepin-4-ol (Reference Example 23) instead of 6-methyl-4,5,6,7-tetrahydrothieno[2,3-c]pyridin-4-ol (Reference Example 6) and was conducted using 4-carbamoyl-2-chloro-1-fluorobenzene instead of 1-fluoronaphthalene to give the objective compound.

Brown powder, MS spectrum: 351[M+H]$^+$

Example 358

4-(Naphthalen-1-yloxy)-2,7-dimethyl-5,6,7,8-tetrahydro-4H-thieno[2,3-c]azepine The same method as in Example 1 was conducted using 2,7-dimethyl-5,6,7,8-tetrahydro-4H-thieno[2,3-c]azepin-4-ol (Reference Example 23) instead of 6-methyl-4,5,6,7-tetrahydrothieno[2,3-c]pyridin-4-ol (Reference Example 6) to give the objective compound.

Brown powder, MS spectrum: 324[M+H]$^+$

Example 359

4-(4-Cyanonaphthalen-1-yloxy)-2,7-dimethyl-5,6,7,8-tetrahydro-4H-thieno[2,3-c]azepine The same method as in Example 1 was conducted using 2,7-dimethyl-5,6,7,8-tetrahydro-4H-thieno[2,3-c]azepin-4-ol (Reference Example 23) instead of 6-methyl-4,5,6,7-tetrahydrothieno[2,3-c]pyridin-4-ol (Reference Example 6) and was conducted using 4-cyano-1-fluoronaphthalene instead of 1-fluoronaphthalene to give the objective compound.

Brown powder, MS spectrum: 349[M+H]$^+$

Example 360

4-(3,4-Dichlorophenyloxy)-5,6,7,8-tetrahydro-4H-thieno[2,3-d]azepine hydrochloride The same method as in Example 3 was conducted using 5,6,7,8-tetrahydro-4H-thieno[2,3-d]azepin-4-ol (Reference Example 29) instead of 6-methyl-4,5,6,7-tetrahydrothieno[2,3-c]pyridin-4-ol (Reference Example 6) and was conducted using 3,4-dichloro-1-fluorobenzene instead of 1,3-difluorobenzene to give the objective compound.
Brown powder, MS spectrum: 314[M+H]$^+$

Example 361

4-(3-Bromo-2-chlorophenyloxy)-5,6,7,8-tetrahydro-4H-thieno[2,3-d]azepine hydrochloride The same method as in Example 3 was conducted using 5,6,7,8-tetrahydro-4H-thieno[2,3-d]azepin-4-ol (Reference Example 29) instead of 6-methyl-4,5,6,7-tetrahydrothieno[2,3-c]pyridin-4-ol (Reference Example 6) and was conducted using 3-bromo-2-chloro-1-fluorobenzene instead of 1,3-difluorobenzene to give the objective compound.
Brown powder, MS spectrum: 358[M+H]$^+$

Example 362

4-(2-Bromophenyloxy)-5,6,7,8-tetrahydro-4H-thieno[2,3-d]azepine hydrochloride

The same method as in Example 3 was conducted using 5,6,7,8-tetrahydro-4H-thieno[2,3-d]azepin-4-ol (Reference Example 29) instead of 6-methyl-4,5,6,7-tetrahydrothieno[2,3-c]pyridin-4-ol (Reference Example 6) and 2-bromo-1-fluorobenzene instead of 1,3-difluorobenzene to give the objective compound.
Brown powder, MS spectrum: 324[M+H]$^+$

Example 363

4-(4-Carbamoyl-2-chlorophenyloxy)-5,6,7,8-tetrahydro-4H-thieno[2,3-d]azepine

The same method as in Example 1 was conducted using 5,6,7,8-tetrahydro-4H-thieno[2,3-d]azepin-4-ol (Reference Example 29) instead of 6-methyl-4,5,6,7-tetrahydrothieno[2,3-c]pyridin-4-ol (Reference Example 6) and was conducted using 4-cyano-1-fluoronaphthalene instead of 1-fluoronaphthalene to give the objective compound.
Brown powder, MS spectrum: 323[M+H]$^+$

Example 364

4-(Naphthalen-1-yloxy)-5,6,7,8-tetrahydro-4H-thieno[2,3-d]azepine

The same method as in Example 1 was conducted using 5,6,7,8-tetrahydro-4H-thieno[2,3-d]azepin-4-ol (Reference Example 29) instead of 6-methyl-4,5,6,7-tetrahydrothieno[2,3-c]pyridin-4-ol (Reference Example 6) to give the objective compound.
Brown powder, MS spectrum: 296[M+H]$^+$

Example 365

4-(4-Cyanonaphthalen-1-yloxy)-5,6,7,8-tetrahydro-4H-thieno[2,3-d]azepine hydrochloride The same method as in Example 3 was conducted using 5,6,7,8-tetrahydro-4H-thieno[2,3-d]azepin-4-ol (Reference Example 29) instead of 6-methyl-4,5,6,7-tetrahydrothieno[2,3-c]pyridin-4-ol (Reference Example 6) and was conducted using 4-cyano-1-fluoronaphthalene instead of 1,3-difluorobenzene to give the objective compound.
Brown powder, MS spectrum: 321[M+H]$^+$

Example 366

4-(3,4-Dichlorophenyloxy)-6-methyl-5,6,7,8-tetrahydro-4H-thieno[2,3-d]azepine hydrochloride The same method as in Example 3 was conducted using 6-methyl-5,6,7,8-tetrahydro-4H-thieno[2,3-d]azepin-4-ol (Reference Example 28) instead of 6-methyl-4,5,6,7-tetrahydrothieno[2,3-c]pyridin-4-ol (Reference Example 6) and was conducted using 3,4-dichloro-1-fluorobenzene instead of 1,3-difluorobenzene to give the objective compound.
Brown powder, MS spectrum: 328[M+H]$^+$

Example 367

4-(3-Bromo-2-chlorophenyloxy)-6-methyl-5,6,7,8-tetrahydro-4H-thieno[2,3-d]azepine The same method as in Example 1 was conducted using 6-methyl-5,6,7,8-tetrahydro-4H-thieno[2,3-d]azepin-4-ol (Reference Example 28) instead of 6-methyl-4,5,6,7-tetrahydrothieno[2,3-c]pyridin-4-ol (Reference Example 6) and was conducted using 3-bromo-2-chloro-1-fluorobenzene instead of 1-fluoronaphthalene to give the objective compound.
Brown powder, MS spectrum: 372[M+H]$^+$

Example 368

4-(2-Bromophenyloxy)-6-methyl-5,6,7,8-tetrahydro-4H-thieno[2,3-d]azepine

The same method as in Example 1 was conducted using 6-methyl-5,6,7,8-tetrahydro-4H-thieno[2,3-d]azepin-4-ol (Reference Example 28) instead of 6-methyl-4,5,6,7-tetrahydrothieno[2,3-c]pyridin-4-ol (Reference Example 6) and was conducted using 2-bromo-1-fluorobenzene instead of 1-fluoronaphthalene to give the objective compound.
Brown powder, MS spectrum: 338[M+H]$^+$

Example 369

4-(4-Carbamoyl-2-chlorophenyloxy)-6-methyl-5,6,7,8-tetrahydro-4H-thieno[2,3-d]azepine hydrochloride The same method as in Example 3 was conducted using 6-methyl-5,6,7,8-tetrahydro-4H-thieno[2,3-d]azepin-4-ol (Reference Example 28) instead of 6-methyl-4,5,6,7-tetrahydrothieno[2,3-c]pyridin-4-ol (Reference Example 6) and was conducted using 4-carbamoyl-2-chloro-1-fluorobenzene instead of 1,3-difluorobenzene to give the objective compound.
Brown powder, MS spectrum: 337[M+H]$^+$

Example 370

4-(Naphthalen-1-yloxy)-6-methyl-5,6,7,8-tetrahydro-4H-thieno[2,3-d]azepine

The same method as in Example 1 was conducted using 6-methyl-5,6,7,8-tetrahydro-4H-thieno[2,3-d]azepin-4-ol (Reference Example 28) instead of 6-methyl-4,5,6,7-tetrahydrothieno[2,3-c]pyridin-4-ol (Reference Example 6) to give the objective compound.

Brown powder, MS spectrum: 310[M+H]$^+$

Example 371

4-(4-Cyanonaphthalen-1-yloxy)-6-methyl-5,6,7,8-tetrahydro-4H-thieno[2,3-d]azepine hydrochloride The same method as in Example 3 was conducted using 6-methyl-5,6,7,8-tetrahydro-4H-thieno[2,3-d]azepin-4-ol (Reference Example 28) instead of 6-methyl-4,5,6,7-tetrahydrothieno[2,3-c]pyridin-4-ol (Reference Example 6) and was conducted using 4-cyano-1-fluoronaphthalene instead of 1,3-difluorobenzene to give the objective compound.

Brown powder, MS spectrum: 335[M+H]$^+$

Example 372

4-(3,4-Dichlorophenyloxy)-6-ethyl-5,6,7,8-tetrahydro-4H-thieno[2,3-d]azepine

The same method as in Example 1 was conducted using 6-ethyl-5,6,7,8-tetrahydro-4H-thieno[2,3-d]azepin-4-ol (Reference Example 45) instead of 6-methyl-4,5,6,7-tetrahydrothieno[2,3-c]pyridin-4-ol (Reference Example 6) and was conducted using 3,4-dichloro-1-fluorobenzene instead of 1-fluoronaphthalene to give the objective compound.

Brown powder, MS spectrum: 342[M+H]$^+$

Example 373

4-(3-Bromo-2-chlorophenyloxy)-6-ethyl-5,6,7,8-tetrahydro-4H-thieno[2,3-d]azepine The same method as in Example 1 was conducted using 6-ethyl-5,6,7,8-tetrahydro-4H-thieno[2,3-d]azepin-4-ol (Reference Example 45) instead of 6-methyl-4,5,6,7-tetrahydrothieno[2,3-c]pyridin-4-ol (Reference Example 6) and was conducted using 3-bromo-2-chloro-1-fluorobenzene instead of 1-fluoronaphthalene to give the objective compound.

Brown powder, MS spectrum: 386[M+H]$^+$

Example 374

4-(2-Bromophenyloxy)-6-ethyl-5,6,7,8-tetrahydro-4H-thieno[2,3-d]azepine

The same method as in Example 1 was conducted using 6-ethyl-5,6,7,8-tetrahydro-4H-thieno[2,3-d]azepin-4-ol (Reference Example 45) instead of 6-methyl-4,5,6,7-tetrahydrothieno[2,3-c]pyridin-4-ol (Reference Example 6) and was conducted using 2-bromo-1-fluorobenzene instead of 1-fluoronaphthalene to give the objective compound.

Brown powder, MS spectrum: 352[M+H]$^+$

Example 375

4-(4-Carbamoyl-2-chlorophenyloxy)-6-ethyl-5,6,7,8-tetrahydro-4H-thieno[2,3-d]azepine The same method as in Example 1 was conducted using 6-ethyl-5,6,7,8-tetrahydro-4H-thieno[2,3-d]azepin-4-ol (Reference Example 45) instead of 6-methyl-4,5,6,7-tetrahydrothieno[2,3-c]pyridin-4-ol (Reference Example 6) and was conducted using 4-carbamoyl-2-chloro-1-fluorobenzene instead of 1-fluoronaphthalene to give the objective compound.

Brown powder, MS spectrum: 351[M+H]$^+$

Example 376

4-(Naphthalen-1-yloxy)-6-ethyl-5,6,7,8-tetrahydro-4H-thieno[2,3-d]azepine

The same method as in Example 1 was conducted using 6-ethyl-5,6,7,8-tetrahydro-4H-thieno[2,3-d]azepin-4-ol (Reference Example 45) instead of 6-methyl-4,5,6,7-tetrahydrothieno[2,3-c]pyridin-4-ol (Reference Example 6) to give the objective compound.

Brown powder, MS spectrum: 324[M+H]$^+$

Example 377

4-(4-Cyanonaphthalen-1-yloxy)-6-ethyl-5,6,7,8-tetrahydro-4H-thieno[2,3-d]azepine hydrochloride The same method as in Example 3 was conducted using 6-ethyl-5,6,7,8-tetrahydro-4H-thieno[2,3-d]azepin-4-ol (Reference Example 45) instead of 6-methyl-4,5,6,7-tetrahydrothieno[2,3-c]pyridin-4-ol (Reference Example 6) and was conducted using 4-cyano-1-fluoronaphthalene instead of 1,3-difluorobenzene to give the objective compound.

Brown powder, MS spectrum: 349[M+H]$^+$

Example 378

7-(3,4-Dichlorophenyloxy)-4,5,6,7-tetrahydrofuro[3,2-c]pyridine

The same method as in Example 1 was conducted using 4,5,6,7-tetrahydrofuro[3,2-c]pyridin-7-ol (Reference Example 33) instead of 6-methyl-4,5,6,7-tetrahydrothieno[2,3-c]pyridin-4-ol (Reference Example 6) and was conducted using 3,4-dichloro-1-fluorobenzene instead of 1-fluoronaphthalene to give the objective compound.

Brown powder, MS spectrum: 284[M+H]$^+$

Example 379

7-(3-Bromo-2-chlorophenyloxy)-4,5,6,7-tetrahydrofuro[3,2-c]pyridine

The same method as in Example 1 was conducted using 4,5,6,7-tetrahydrofuro[3,2-c]pyridin-7-ol (Reference Example 33) instead of 6-methyl-4,5,6,7-tetrahydrothieno[2,3-c]pyridin-4-ol (Reference Example 6) and was conducted using 3-bromo-2-chloro-1-fluorobenzene instead of 1-fluoronaphthalene to give the objective compound.

Brown powder, MS spectrum: 328[M+H]$^+$

Example 380

7-(2-Bromophenyloxy)-4,5,6,7-tetrahydrofuro[3,2-c]pyridine

The same method as in Example 1 was conducted using 4,5,6,7-tetrahydrofuro[3,2-c]pyridin-7-ol (Reference Example 33) instead of 6-methyl-4,5,6,7-tetrahydrothieno[2,3-c]pyridin-4-ol (Reference Example 6) and was conducted using 2-bromo-1-fluorobenzene instead of 1-fluoronaphthalene to give the objective compound.
Brown powder, MS spectrum: 294[M+H]$^+$

Example 381

7-(4-Carbamoyl-2-chlorophenyloxy)-4,5,6,7-tetrahydrofuro[3,2-c]pyridine

The same method as in Example 1 was conducted using 4,5,6,7-tetrahydrofuro[3,2-c]pyridin-7-ol (Reference Example 33) instead of 6-methyl-4,5,6,7-tetrahydrothieno[2,3-c]pyridin-4-ol (Reference Example 6) and was conducted using 4-carbamoyl-2-chloro-1-fluorobenzene instead of 1-fluoronaphthalene to give the objective compound.
Brown powder, MS spectrum: 293[M+H]$^+$

Example 382

7-(Naphthalen-1-yloxy)-4,5,6,7-tetrahydrofuro[3,2-c]pyridine

The same method as in Example 1 was conducted using 4,5,6,7-tetrahydrofuro[3,2-c]pyridin-7-ol (Reference Example 33) instead of 6-methyl-4,5,6,7-tetrahydrothieno[2,3-c]pyridin-4-ol (Reference Example 6) to give the objective compound.
Brown powder, MS spectrum: 266[M+H]$^+$

Example 383

7-(4-Cyanonaphthalen-1-yloxy)-4,5,6,7-tetrahydrofuro[3,2-c]pyridine

The same method as in Example 1 was conducted using 4,5,6,7-tetrahydrofuro[3,2-c]pyridin-7-ol (Reference Example 33) instead of 6-methyl-4,5,6,7-tetrahydrothieno[2,3-c]pyridin-4-ol (Reference Example 6) and was conducted using 4-cyano-1-fluoronaphthalene instead of 1-fluoronaphthalene to give the objective compound.
Brown powder, MS spectrum: 291[M+H]$^+$

Example 384

7-(3,4-Dichlorophenyloxy)-5-methyl-4,5,6,7-tetrahydrofuro[3,2-c]pyridine

The same method as in Example 1 was conducted using 5-methyl-4,5,6,7-tetrahydrofuro[3,2-c]pyridin-7-ol (Reference Example 3) instead of 6-methyl-4,5,6,7-tetrahydrothieno[2,3-c]pyridin-4-ol (Reference Example 6) and was conducted using 3,4-dichloro-1-fluorobenzene instead of 1-fluoronaphthalene to give the objective compound.
Brown powder, MS spectrum: 298[M+H]$^+$

Example 385

7-(3-Bromo-2-chlorophenyloxy)-5-methyl-4,5,6,7-tetrahydrofuro[3,2-c]pyridine

The same method as in Example 1 was conducted using 5-methyl-4,5,6,7-tetrahydrofuro[3,2-c]pyridin-7-ol (Reference Example 3) instead of 6-methyl-4,5,6,7-tetrahydrothieno[2,3-c]pyridin-4-ol (Reference Example 6) and was conducted using 3-bromo-2-chloro-1-fluorobenzene instead of 1-fluoronaphthalene to give the objective compound.
Brown powder, MS spectrum: 342[M+H]$^+$

Example 386

7-(2-Bromophenyloxy)-5-methyl-4,5,6,7-tetrahydrofuro[3,2-c]pyridine

The same method as in Example 1 was conducted using 5-methyl-4,5,6,7-tetrahydrofuro[3,2-c]pyridin-7-ol (Reference Example 3) instead of 6-methyl-4,5,6,7-tetrahydrothieno[2,3-c]pyridin-4-ol (Reference Example 6) and was conducted using 2-bromo-1-fluorobenzene instead of 1-fluoronaphthalene to give the objective compound.
Brown powder, MS spectrum: 308[M+H]$^+$

Example 387

7-(4-Carbamoyl-2-chlorophenyloxy)-5-methyl-4,5,6,7-tetrahydrofuro[3,2-c]pyridine The same method as in Example 1 was conducted using 5-methyl-4,5,6,7-tetrahydrofuro[3,2-c]pyridin-7-ol (Reference Example 3) instead of 6-methyl-4,5,6,7-tetrahydrothieno[2,3-c]pyridin-4-ol (Reference Example 6) and was conducted using 4-carbamoyl-2-chloro-1-fluorobenzene instead of 1-fluoronaphthalene to give the objective compound.
Brown powder, MS spectrum: 307[M+H]$^+$

Example 388

7-(Naphthalen-1-yloxy)-5-methyl-4,5,6,7-tetrahydrofuro[3,2-c]pyridine

The same method as in Example 1 was conducted using 5-methyl-4,5,6,7-tetrahydrofuro[3,2-c]pyridin-7-ol (Reference Example 3) instead of 6-methyl-4,5,6,7-tetrahydrothieno[2,3-c]pyridin-4-ol (Reference Example 6) to give the objective compound.
Brown powder, MS spectrum: 280[M+H]$^+$

Example 389

7-(4-Cyanonaphthalen-1-yloxy)-5-methyl-4,5,6,7-tetrahydrofuro[3,2-c]pyridine

The same method as in Example 1 was conducted using 5-methyl-4,5,6,7-tetrahydrofuro[3,2-c]pyridin-7-ol (Reference Example 3) instead of 6-methyl-4,5,6,7-tetrahydrothieno[2,3-c]pyridin-4-ol (Reference Example 6) and was conducted using 4-cyano-1-fluoronaphthalene instead of 1-fluoronaphthalene to give the objective compound.
Brown powder, MS spectrum: 305[M+H]$^+$

Example 390

7-(3,4-Dichlorophenyloxy)-5-ethyl-4,5,6,7-tetrahydrofuro[3,2-c]pyridine

The same method as in Example 1 was conducted using 5-ethyl-4,5,6,7-tetrahydrofuro[3,2-c]pyridin-7-ol (Reference Example 34) instead of 6-methyl-4,5,6,7-tetrahydrothieno[2,3-c]pyridin-4-ol (Reference Example 6) and was conducted using 3,4-dichloro-1-fluorobenzene instead of 1-fluoronaphthalene to give the objective compound.
Brown powder, MS spectrum: 312[M+H]$^+$

Example 391

7-(3-Bromo-2-chlorophenyloxy)-5-ethyl-4,5,6,7-tetrahydrofuro[3,2-c]pyridine

The same method as in Example 1 was conducted using 5-ethyl-4,5,6,7-tetrahydrofuro[3,2-c]pyridin-7-ol (Reference Example 34) instead of 6-methyl-4,5,6,7-tetrahydrothieno[2,3-c]pyridin-4-ol (Reference Example 6) and was conducted using 3-bromo-2-chloro-1-fluorobenzene instead of 1-fluoronaphthalene to give the objective compound.
Brown powder, MS spectrum: 356[M+H]$^+$

Example 392

7-(2-Bromophenyloxy)-5-ethyl-4,5,6,7-tetrahydrofuro[3,2-c]pyridine

The same method as in Example 1 was conducted using 5-ethyl-4,5,6,7-tetrahydrofuro[3,2-c]pyridin-7-ol (Reference Example 34) instead of 6-methyl-4,5,6,7-tetrahydrothieno[2,3-c]pyridin-4-ol (Reference Example 6) and was conducted using 2-bromo-1-fluorobenzene instead of 1-fluoronaphthalene to give the objective compound.
Brown powder, MS spectrum: 322[M+H]$^+$

Example 393

7-(4-Carbamoyl-2-chlorophenyloxy)-5-ethyl-4,5,6,7-tetrahydrofuro[3,2-c]pyridine

The same method as in Example 1 was conducted using 5-ethyl-4,5,6,7-tetrahydrofuro[3,2-c]pyridin-7-ol (Reference Example 34) instead of 6-methyl-4,5,6,7-tetrahydrothieno[2,3-c]pyridin-4-ol (Reference Example 6) and was conducted using 4-carbamoyl-2-chloro-1-fluorobenzene instead of 1-fluoronaphthalene to give the objective compound.
Brown powder, MS spectrum: 321[M+H]$^+$

Example 394

7-(Naphthalen-1-yloxy)-5-ethyl-4,5,6,7-tetrahydrofuro[3,2-c]pyridine

The same method as in Example 1 was conducted using 5-ethyl-4,5,6,7-tetrahydrofuro[3,2-c]pyridin-7-ol (Reference Example 34) instead of 6-methyl-4,5,6,7-tetrahydrothieno[2,3-c]pyridin-4-ol (Reference Example 6) to give the objective compound.
Brown powder, MS spectrum: 294[M+H]$^+$

Example 395

7-(4-Cyanonaphthalen-1-yloxy)-5-ethyl-4,5,6,7-tetrahydrofuro[3,2-c]pyridine

The same method as in Example 1 was conducted using 5-ethyl-4,5,6,7-tetrahydrofuro[3,2-c]pyridin-7-ol (Reference Example 34) instead of 6-methyl-4,5,6,7-tetrahydrothieno[2,3-c]pyridin-4-ol (Reference Example 6) and was conducted using 4-cyano-1-fluoronaphthalene instead of 1-fluoronaphthalene to give the objective compound.
Brown powder, MS spectrum: 319[M+H]$^+$

Example 396

(+)-4-(3,4-Dichlorophenyloxy)-6-methyl-4,5,6,7-tetrahydrofuro[2,3-c]pyridine hydrochloride The same method as in Example 3 was conducted using (+)-6-methyl-4,5,6,7-tetrahydrothieno[2,3-c]pyridin-4-ol (Reference Example 50) instead of 6-methyl-4,5,6,7-tetrahydrothieno[2,3-c]pyridin-4-ol (Reference Example 6) and was conducted using 3,4-dichloro-1-fluorobenzene instead of 1,3-difluorobenzene to give the objective compound.
Ecru solid, MS spectrum: 298[M+H]$^+$, 99.0% ee
Specific rotation $[\alpha]_D$=+102.6° (25° C., c=1.18, MeOH)

Example 397

(+)-7-Methyl-4-(naphthalen-1-yloxy)-5,6,7,8-tetrahydro-4H-furo[2,3-c]azepine hydrochloride The same method as in Example 3 was conducted using 7-methyl-5,6,7,8-tetrahydro-4H-furo[2,3-c]azepin-4-ol (Reference Example 52) instead of 6-methyl-4,5,6,7-tetrahydrothieno[2,3-c]pyridin-4-ol (Reference Example 6) and was conducted using 1-fluoronaphthalene instead of 1,3-difluorobenzene to give the objective compound.
Colorless powder, MS spectrum: 294[M+H]$^+$, 99.0% ee
Specific rotation $[\alpha]_D$=+30.3° (25° C., c=3.13, MeOH)

Example 398

(+)-4-(3-Bromo-2-chlorophenyloxy)-7-methyl-5,6,7,8-tetrahydro-4H-furo[2,3-c]azepine hydrochloride The same method as in Example 3 was conducted using 7-methyl-5,6,7,8-tetrahydro-4H-furo[2,3-c]azepin-4-ol (Reference Example 52) instead of 6-methyl-4,5,6,7-tetrahydrothieno[2,3-c]pyridin-4-ol (Reference Example 6) and was conducted using 3-bromo-2-chloro-1-fluorobenzene instead of 1,3-difluorobenzene to give the objective compound.
Colorless powder, MS spectrum: 358[M+H]$^+$, 99.0% ee
Specific rotation $[\alpha]_D$=+56.3° (25° C., c=2.01, MeOH)

Example 399

(+)-4-(3-Bromo-2-chlorophenyloxy)-2,7-dimethyl-5,6,7,8-tetrahydro-4H-furo[2,3-c]azepine hydrochloride The same method as in Example 3 was conducted using (+)-2,7-dimethyl-5,6,7,8-tetrahydro-4H-furo[2,3-c]azepin-4-ol (Reference Example 56) instead of 6-methyl-4,5,6,7-tetrahydrothieno[2,3-c]pyridin-4-ol (Reference Example 6)

and was conducted using 3-bromo-2-chloro-1-fluorobenzene instead of 1,3-difluorobenzene to give the objective compound.

Pale yellow powder, MS spectrum: 370[M+H]$^+$, 99.9% ee
Specific rotation [α]$_D$=+29.2° (25° C., c=0.96, MeOH)

Example 400

(+)-4-(2,3-Dichlorophenyloxy)-7-methyl-5,6,7,8-tetrahydro-4H-furo[2,3-c]azepine hydrochloride The same method as in Example 3 was conducted using (+)-7-methyl-5,6,7,8-tetrahydro-4H-furo[2,3-c]azepin-4-ol (Reference Example 52) instead of 6-methyl-4,5,6,7-tetrahydrothieno[2,3-c]pyridin-4-ol (Reference Example 6) and was conducted using 2,3-dichloro-1-fluorobenzene instead of 1,3-difluorobenzene to give the objective compound.

Colorless powder, MS spectrum: 312[M+H]$^+$, 99.0% ee
Specific rotation [α]$_D$=+79.0° (25° C., c=1.38, MeOH)

Example 401

(+)-2,7-Dimethyl-4-(naphthalen-1-yloxy)-5,6,7,8-tetrahydro-4H-furo[2,3-c]azepine hydrochloride The same method as in Example 3 was conducted using (+)-2,7-dimethyl-5,6,7,8-tetrahydro-4H-furo[2,3-c]azepin-4-ol (Reference Example 56) instead of 6-methyl-4,5,6,7-tetrahydrothieno[2,3-c]pyridin-4-ol (Reference Example 6) and was conducted using 1-fluoronaphthalene instead of 1,3-difluorobenzene to give the objective compound.

Pink powder, MS spectrum: 308[M+H]$^+$, 99.9% ee
Specific rotation [α]$_D$=+7.0° (25° C., c=1.03, MeOH)

Example 402

(+)-4-(2-Chloro-4-carbamoylphenyloxy)-7-methyl-5,6,7,8-tetrahydro-4H-furo[2,3-c]azepine hydrochloride The same method as in Example 3 was conducted using (+)-7-methyl-5,6,7,8-tetrahydro-4H-furo[2,3-c]azepin-4-ol (Reference Example 52) instead of 6-methyl-4,5,6,7-tetrahydrothieno[2,3-c]pyridin-4-ol (Reference Example 6) and was conducted using 4-carbamoyl-2-chloro-fluorobenzene instead of 1,3-difluorobenzene to give the objective compound.

Pale yellow powder, MS spectrum: 321[M+H]$^+$, 99.0% ee
Specific rotation [α]$_D$=+100.3° (25° C., c=2.63, MeOH)

Example 403

(−)-7-Methyl-4-(naphthalen-1-yloxy)-5,6,7,8-tetrahydro-4H-furo[2,3-c]azepine hydrochloride The same method as in Example 3 was conducted using (−)-7-methyl-5,6,7,8-tetrahydro-4H-furo[2,3-c]azepin-4-ol (Reference Example 54) instead of 6-methyl-4,5,6,7-tetrahydrothieno[2,3-c]pyridin-4-ol (Reference Example 6) and was conducted using 1-fluoronaphthalene instead of 1,3-difluorobenzene to give the objective compound.

Colorless powder, MS spectrum: 294[M+H]$^+$, 98.7% ee
Specific rotation [α]$_D$=−35.4° (25° C., c=2.48, MeOH)

Example 404

(−)-4-(3-Bromo-2-chlorophenyloxy)-7-methyl-5,6,7,8-tetrahydro-4H-furo[2,3-c]azepine hydrochloride The same method as in Example 3 was conducted using (−)-7-methyl-5,6,7,8-tetrahydro-4H-furo[2,3-c]azepin-4-ol (Reference Example 54) instead of 6-methyl-4,5,6,7-tetrahydrothieno[2,3-c]pyridin-4-ol (Reference Example 6) and was conducted using 3-bromo-2-chloro-1-fluorobenzene instead of 1,3-difluorobenzene to give the objective compound.

Colorless powder, MS spectrum: 358[M+H]$^+$, 98.7% ee
Specific rotation [α]$_D$=−61.5° (25° C., c=1.83, MeOH)

Example 405

(−)-4-(3-Bromo-2-chlorophenyloxy)-2,7-dimethyl-5,6,7,8-tetrahydro-4H-furo[2,3-c]azepine hydrochloride The same method as in Example 3 was conducted using (−)-2,7-dimethyl-5,6,7,8-tetrahydro-4H-furo[2,3-c]azepin-4-ol (Reference Example 58) instead of 6-methyl-4,5,6,7-tetrahydrothieno[2,3-c]pyridin-4-ol (Reference Example 6) and was conducted using 3-bromo-2-chloro-1-fluorobenzene instead of 1,3-difluorobenzene to give the objective compound.

Pale yellow powder, MS spectrum: 370[M+H]$^+$, 99.0% ee
Specific rotation [α]$_D$=−40.9° (25° C., c=1.67, MeOH)

Example 406

(−)-4-(2,3-Dichlorophenyloxy)-7-methyl-5,6,7,8-tetrahydro-4H-furo[2,3-c]azepine hydrochloride The same method as in Example 3 was conducted using (−)-7-methyl-5,6,7,8-tetrahydro-4H-furo[2,3-c]azepin-4-ol (Reference Example 54) instead of 6-methyl-4,5,6,7-tetrahydrothieno[2,3-c]pyridin-4-ol (Reference Example 6) and was conducted using 2,3-dichloro-1-fluorobenzene instead of 1,3-difluorobenzene to give the objective compound.

Colorless powder, MS spectrum: 312[M+H]$^+$, 98.7% ee
Specific rotation [α]$_D$=−94.0° (25° C., c=1.00, MeOH)

Example 407

(−)-2,7-Dimethyl-4-(naphthalen-1-yloxy)-5,6,7,8-tetrahydro-4H-furo[2,3-c]azepine hydrochloride The same method as in Example 3 was conducted using (−)-2,7-dimethyl-5,6,7,8-tetrahydro-4H-furo[2,3-c]azepin-4-ol (Reference Example 58) instead of 6-methyl-4,5,6,7-tetrahydrothieno[2,3-c]pyridin-4-ol (Reference Example 6) and was conducted using 1-fluoronaphthalene instead of 1,3-difluorobenzene to give the objective compound.

Pink powder, MS spectrum: 308[M+H]$^+$, 99.0% ee
Specific rotation [α]$_D$=−13.6° (25° C., c=1.00, MeOH)

Example 408

(−)-4-(2-Chloro-4-carbamoylphenyloxy)-7-methyl-5,6,7,8-tetrahydro-4H furo[2,3-c]azepine hydrochloride The same method as in Example 3 was conducted using (−)-7-methyl-5,6,7,8-tetrahydro-4H-furo[2,3-c]azepin-4-ol (Reference Example 54) instead of 6-methyl-4,5,6,7-tetrahydrothieno[2,3-c]pyridin-4-ol (Reference Example 6) and was conducted using 4-carbamoyl-2-chloro-1-fluorobenzene instead of 1,3-difluorobenzene to give the objective compound.

Pale yellow powder, MS spectrum: 321[M+H]$^+$, 98.7% ee
Specific rotation $[\alpha]_D$=−105.7° (25° C., =1.81, c MeOH)

Test Example 1

Experiments for Inhibition of Serotonin Reuptake and Experiments for Inhibition of Norepinephrine Reuptake Cerebral cortex of male SD rats (JAPAN SLC Inc.), over six weeks of age was excised and a 0.32M sucrose solution was added thereto in an amount of 10 mL per gram of the cerebral cortex followed by homogenizing. The homogenized solution was centrifuged, the supernatant thereof was further centrifuged at high speed and, to the resulting pellets, a PSS solution (pH 7.4; comprising 150 mM of NaCl, 4 mM of KCl, 1 mM of MgCl$_2$, 2.5 mM of HEPES, 0.9 mg/mL of glucose, 0.176 mg/mL of ascorbic acid and 1 mM of pargylin) was added in an amount of 10 mL per gram of the pellets to give a synaptosome solution. A compound to be tested (100 μL) was added to 100 μL of the synaptosome solution and 700 μL of a 50 mM Tris buffer (pH 7.4; trihydroxylaminomethane) followed by subjecting to pre-incubation at 37° C. for 5 minutes. After the pre-incubation, 100 μL of [$^3$H] serotonin or [$^3$H]norepinephrine diluted to 10 nM and 20 nM, respectively, with a Tris buffer was added thereto followed by incubating at 37° C. for 5 minutes.

Synaptosome was recovered on a GF/B filter using a cell harvester and further washed three times using a washing solution (50 mM Tris buffer; pH 7.4; 4° C.). The filter was transferred to a vial, a scintillator was added thereto and the radiation activity was measured using a liquid scintillation counter.

Incidentally, the non-specific reaction was defined as the radiation activity under ice-cooling (4° C.) and the difference between the total radiation activity and the radiation activity under the non-specific reaction was adopted as the radiation activity specifically re-uptaken in the synaptosome. IC$_{50}$ value was determined from the re-uptake inhibition rate in the presence of a test compound and, from IC$_{50}$ value and the Kd value of [$^3$H]serotonin or [$^3$H]norepinephrine, Ki value of the test compound showing a re-uptake inhibiting activity of serotonin or norepinephrine, respectively, was calculated.

TABLE 1

| Test Compound | Serotonin Reuptake Inhibiting Activity; Ki value (nM) | Norepinephrine Reuptake Inhibiting Activity; Ki value (nM) |
|---|---|---|
| Example 2 | 27.2 | 477.8 |
| Example 24 | 9.5 | 278.6 |
| Example 57 | 14.1 | 244.0 |
| Example 66 | 3.9 | 484.4 |
| Example 84 | 7.9 | 207.1 |
| Example 98 | 8.6 | 454.9 |
| Example 102 | 3.4 | 4.0 |
| Example 108 | 1.7 | 64.4 |
| Example 109 | 8.9 | 66.2 |
| Example 115 | 1.2 | 70.7 |
| Example 135 | 5.4 | 43.2 |
| Example 140 | 4.1 | 8.4 |
| Example 148 | 2.1 | 2.0 |
| Example 149 | 1.8 | 1.7 |
| Example 157 | 6.8 | 57.5 |
| Example 163 | 3.8 | 12.0 |
| Example 168 | 6.6 | 23.8 |

TABLE 1-continued

| Test Compound | Serotonin Reuptake Inhibiting Activity; Ki value (nM) | Norepinephrine Reuptake Inhibiting Activity; Ki value (nM) |
|---|---|---|
| Example 177 | 3.1 | 27.5 |
| Example 179 | 1.0 | 24.4 |
| Example 213 | 0.9 | 4.1 |
| Example 200 | 1.7 | 21.5 |
| Example 225 | 18.3 | 11.7 |
| Example 398 | 1.7 | 5.6 |
| Example 400 | 0.5 | 2.4 |
| Example 401 | 1.0 | 3.2 |

Test Example 2

Measurement of Urine Leak Point Pressure in Rats Under Anesthesia

Under anesthesia with urethane (1.2 g/kg; subcutaneous administration), the thoracic spine of female rats of 8 to 12 weeks of age (Japan SLC Inc.) was cut at the level of T8 to T9 so that the micturition reflex was made to disappear, then the abdomen was subjected to a median incision to expose the bladder and then a cannula was inserted into the bladder. An appropriate amount (ca. 0.4 mL) of a physiological saline was previously infused into the bladder, both sides of the bladder were gradually pressed with two cotton buds and the inner pressure of the bladder when the physiological saline solution leaked out from the urethral orifice was measured as a pressure upon leakage of urine. The measurement was repeated several times until the measured values became stable and, after that, the test compound was intravenously administered and a pharmacological effect of the test compound was evaluated.

As a result, intravenous administration of not more than 10 mg/kg of the test compounds of Examples 21, 102, 133, 398, 400 and 401 raised the leak point pressure. Thus, urine was less prone to leak out after those test compounds were administered.

Test Example 3

Measurement of Electromyogram of External Urethral Sphincter of Rats Under Anesthesia Abdomen of female rats of 6 to 12 weeks of age or in a retired state (Japan SLC Inc.) was subjected to a median incision under anesthesia with urethane (1.2 g/kg; subcutaneous administration) to cut the pubis. A stainless electrode was inserted into the external urethral sphincter found around the urinary canal using a 27G needle as a guide cannula. Electric signal from the stainless electrode was amplified using a biological amplifier (MEG-1200 manufactured by NIHON KOHDEN CORPORATION) and the electromyogram of the external urethral sphincter was recorded using a recticorder and a DAT recorder. If necessary, measurement of the inner pressure of bladder and incision of the thoracic spine were carried out at the same time. After confirmation of disappearance or stabilization of natural ignition of the external urethral sphincter, the test compound was administered intravenously, subcutaneously or intraduodenally and the influence of the test compound on the electromyogram of the external urethral sphincter was examined.

Test Example 4

Observation of General Symptoms in Mice

The test compound was intravenously administered to male Slc:ICR mice of six weeks of age (Japan SLC Inc.) and the behaviors of the mice were observed continuously until 6 hours thereafter and also after 24 hours.

Test Example 5

Measurements of Heart Rate and Electrocardiogram of Guinea Pigs Under Anesthetization Male guinea pigs of an Std:Hartley strain of 350 to 1,000 g body weight (Japan SLC Inc.) were anesthetized with isoflurane (5%; 25% $O_2$+75% air) in a chamber, taken out from the chamber and in fixed face-up position. During the experiment, the guinea pigs were subjected to inhalation anesthesia (54 strokes/minute; tidal volume 10 mL/kg) with isoflurane (2.5 to 3.5%; 25% $O_2$+75% air) via an artificial respirator (Model 681; Harvard Apparatus Inc., U.S.A.) from a cannula inserted into the airway. Electrocardiogram was measured via a preamp for bioelectricity (AB-621G; manufactured by NIHON KOHDEN CORPORATION) by means of the standard I- and II-inductions of four limbs and the analysis thereof was carried out using an ECG processor (SP 2000 version 1.31F4, Softron). The heart rate was measured via an instant heart rate unit (AT-601G; manufactured by NIHON KOHDEN CORPORATION) using R wave of the electrocardiogram as a trigger. Pacing was conducted in such a manner that an electrode was inserted from the right jugular vein to the right ventricle and the cycle length was fixed at 300 msec via an isolater (SS-202J; manufactured by NIHON KOHDEN CORPORATION) from an electric stimulation apparatus (SEN-3301; manufactured by NIHON KOHDEN CORPORATION). A cannula for the administration of a test compound was inserted into the left jugular vein. The administration of a test compound was carried out in such a manner that a volume of 2.0 mL/kg was applied taking 10 minutes. Measurement of parameters during a non-pacing period was conducted every minute during the periods of 15 minutes before and after the administration and at 20, 25 and 30 minutes after the administration, while measurement during a pacing period was conducted every five minutes from immediately before the administration until 30 minutes after the administration. Correction of the QT intervals upon the non-pacing period was carried out using the formulae of Bazette (QTcb, $QT/RR^{1/2}$) and Fridericia (QTcf, $QT/RR^{1/3}$). When arrhythmia such as premature beat or atrioventricular conductive block was observed on the electrocardiogram before the administration of the test compound, such a case was excluded from the experiment.

Test Example 6

Measurement of Heart Rate and Electrocardiogram of Dogs Under Anesthesia

Dogs of 8 to 12 kg body weight were anesthetized with thiopental sodium (20 mg/kg, i.v.) and fixed in face-up position on a temperature-keeping mat kept at 37 to 38° C. (K-20; American Pharmaseal Company, Valencia). During the experiment, dogs were subjected to the inhalation anesthesia (tidal volume 20 mL/kg; 20 breaths/min.) with halothane (1 to 2%; 25% $O_2$+75% air) via an artificial respirator (Model 613; Harvard Apparatus Inc.) from a cannula inserted into the airway. Electrocardiogram was measured via a preamp for bioelectricity (AB-620G; manufactured by NIHON KOHDEN CORPORATION) using a needle electrode by means of the standard II-inductions of four limbs and the analysis thereof was carried out using an ECG processor (SP 2000 version 1.31F4, Softron). Correction of QT intervals (QTcf) was conducted by the formula of Fridericia ($QT/RR^{1/3}$). Administration of a medium or a test compound was conducted in such a manner that a volume of 2 mL/kg was subjected to a continuous infusion for a period of 30 minutes using an infusion pump (KDS 100; KD Scientific Inc., U.S.A.) by a cannula previously placed in the outer saphenous vein. Measurement was conducted with intervals of 5 minutes from 10 minutes before the continuous infusion of a test compound until 120 minutes after the start.

Test Example 7

Measurement of hERG Current

CHO-K1 cells transformed with hERG were used. An extracellular fluid was perfused (ca. 3 mL/min) in a chamber for patch clamp fixed on a stage of a microscope. A cover glass to which the cells for the measurement were adhered was aligned in the chamber. A patch clamp method was applied to the cells for the measurement and the hERG current was gained via a patch clamp amplifier. An electrode showing the electrode resistance of 4 to 8 MΩ when an inner liquid of electrode was filled therein was used. Membrane potential of the cells was fixed at −75 mV and depolarizing pulse of +50 mV was applied for 0.5 seconds at the frequency of once every ten seconds and, after that, repolarizing pulse of −40 mV was applied for 0.5 second to induce the hERG current. After confirming that a stable hERG tail current was gained, a solution of a test compound was applied. The cover glass seeded with the cells was exchanged upon every application. Temperature of the extracellular liquid in the perfusion container was maintained at 36° C.±1° C. After perfusion of the applied solution of a test compound, a positive control substance at a high concentration (E-4031; 10 μmol/L) was applied and it was confirmed that the hERG current was completely suppressed.

Test Example 8

Simple Test for Reverse Mutation

After a test strain (*Salmonella typhimurium* and *Escherichia coli*), a test compound and S9 mix {a 9000×g supernatant fraction of a liver homogenate of male rats of an SD strain (Charles River Laboratories Japan Inc.) to which phenobarbital and 5,6-benzoflavone were co-administered; manufactured by Oriental Yeast Co., Ltd.} were subjected to a pre-incubation (at 37° C. for 20 minutes), it was seeded on a culture dish and incubated for 48 hours and the number of reverse-mutated colonies that appeared thereon was counted. Measurement of the reverse-mutated colony numbers was conducted using an automated colony counter (BMS-400; manufactured by TOYO SOKKI CO., LTD.) where the same plate was rotated in 900 for two times. After that, area correction and missed-out count correction were done and the result was adopted as reverse-mutation colony numbers for each plate. When the count by the automated colony counter was impossible due to separation of the test compound, etc., a manual colony counter was used and the observation was done by naked eye.

Test Example 9

Simple Test for Chromosomal Aberration

As a cell strain for the test, a cell strain CHL/IU which was derived from lung of neonatal Chinese hamsters was used and the test was carried out in the absence and presence of S9 mix {a 9000×g supernatant fraction of a liver homogenate of male rats of an SD strain (Charles River Laboratories Japan Inc.) to which phenobarbital and 5,6-benzoflavone were co-administered; manufactured by Oriental Yeast Co., Ltd.}. The test strain was seeded on a culture dish, a test compound was added after 3 days, then the cell strain was peeled off on the next day and chromosomal aberration was tested. A chromosome specimen was prepared by a conventional method and structural aberrations (gap, incision and exchange of chromatid type and chromosome type and fragmentation) and the number of aberrations (ploidy) were observed. With regard to the frequency of appearance of cells with the chromosomal aberrations, a direct probability calculating method of Fisher was conducted between a negative (solvent) control and a test compound. A part of the cell collection liquid collected at the preparation of chromosome specimens was taken and subjected to the cell number measurement using a particle counting/analyzing apparatus whereby the cell growth rate was calculated.

As mentioned hereinabove, it is apparent that the compound of the present invention and a pharmaceutically acceptable salt thereof have an excellent inhibitory action against reuptake of serotonin and an excellent inhibitory action against reuptake of norepinephrine and are able to be used as a preventive or therapeutic agent for diseases such as depression, panic disorder, anxiety, obsessive-compulsive disorder, chronic pain, fibromyalgia, obesity, stress urinary incontinence or overactive bladder.

Preparation Example 1

Tablets (For Oral Administration)

Formulation: Each tablet (80 mg) contains the following

| | |
|---|---|
| Compound of Example 1 | 5.0 mg |
| Corn starch | 46.6 mg |
| Crystalline cellulose | 24.0 mg |
| Methyl cellulose | 4.0 mg |
| Magnesium stearate | 0.4 mg |

The mixed powder in the above ratio was made into tablets by a conventional method to prepare tablets for oral administration.

Preparation Example 2

Tablets (For Oral Administration)

Formulation: Each tablet (80 mg) contains the following

| | |
|---|---|
| Compound of Example 2 | 5.0 mg |
| Corn starch | 46.6 mg |
| Crystalline cellulose | 24.0 mg |
| Methyl cellulose | 4.0 mg |
| Magnesium stearate | 0.4 mg |

The mixed powder in the above ratio was made into tablets by a conventional method to prepare tablets for oral administration.

INDUSTRIAL APPLICABILITY

The compound of the present invention and a pharmaceutically acceptable salt thereof are able to be used as a preventive or a therapeutic agent for diseases such as depression, panic disorder, anxiety, obsessive-compulsive disorder, chronic pain, fibromyalgia, obesity, stress urinary incontinence or overactive bladder.

The invention claimed is:

1. A compound represented by formula [1] or a pharmaceutically acceptable salt thereof,

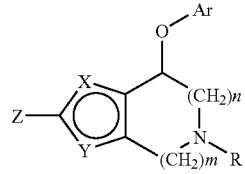

[1]

wherein:
X is CH and Y is oxygen;
R represents hydrogen, dialkylaminoacetyl, or alkyl optionally substituted with one to three substituents selected from the group consisting of cycloalkyl, alkenyl, halogen, cyano, amino, dialkylamino, alkoxycarbonyl, pyridyl, alkoxy, and hydroxy;
Z represents hydrogen, alkyl, halogen, nitrile, or phenyl optionally substituted with one to three substituents selected from the group consisting of alkyl, alkoxy, and halogen;
Ar represents phenyl, naphthyl, pyridyl, quinolyl, isoquinolyl, indolyl, carbazolyl, dibenzofuranyl, benzothienyl, or benzofuranyl, each of which is optionally substituted with one to three substituents selected from the group consisting of alkyl, hydroxyalkyl, alkoxy, halogen, haloalkyl, haloalkoxy, nitro, cyano, phenyl, aminocarbonyl, benzyloxy, benzyloxycarbonyl, hydroxycarbonyl, methoxycarbonyl, methanesulfonyl, amino, acetylamino, phthalimido, acetyl, monoalkylaminocarbonyl, and dialkylaminocarbonyl;
wherein when Ar is an optionally substituted phenyl, the phenyl as such is optionally condensed with a cyclopentane ring, a cyclohexane ring, or a dioxolane ring; and
n is 2 and m is 1.

2. The compound according to claim 1 or a pharmaceutically acceptable salt thereof, wherein R is hydrogen or alkyl optionally substituted with one to three substituents selected from the group consisting of cycloalkyl, alkenyl, halogen, cyano, amino, dialkylamino, alkoxycarbonyl, pyridyl, alkoxy, and hydroxy.

3. The compound according to claim 1 or a pharmaceutically acceptable salt thereof, wherein Z is hydrogen, alkyl, halogen, or nitrile.

4. The compound according to claim 1 or a pharmaceutically acceptable salt thereof, wherein Z is hydrogen or alkyl.

5. The compound according to claim for a pharmaceutically acceptable salt thereof, wherein:
Ar is phenyl, naphthyl, or pyridyl, each of which is optionally substituted with one to three substituents selected from the group consisting of alkyl, hydroxyalkyl, alkoxy, halogen, haloalkyl, haloalkoxy, nitro, cyano, phenyl, aminocarbonyl, benzyloxy, benzyloxycarbonyl, hydroxycarbonyl, methoxycarbonyl, methanesulfonyl, amino, acetylamino, phthalimido, acetyl, monoalkylaminocarbonyl, and dialkylaminocarbonyl; and when Ar is an optionally substituted phenyl, the phenyl as such is optionally condensed with a cyclopentane ring, a cyclohexane ring, or a dioxolane ring.

6. The compound according to claim 1 or a pharmaceutically acceptable salt thereof, wherein Ar is phenyl, naphthyl, or pyridyl, each of which is optionally substituted with one to three substituents selected from the group consisting of alkyl, halogen, aminocarbonyl, and dialkylaminocarbonyl.

7. The compound according to claim 1 or a pharmaceutically acceptable salt thereof, wherein:

R is hydrogen or alkyl optionally substituted with one to three substituents selected from the group consisting of cycloalkyl, alkenyl, halogen, cyano, amino, dialkylamino, alkoxycarbonyl, pyridyl, alkoxy, and hydroxy;

Z is hydrogen or alkyl;

Ar is phenyl, naphthyl, or pyridyl, each of which is optionally substituted with one to three substituents selected from the group consisting of alkyl, halogen, aminocarbonyl, and dialkylaminocarbonyl; and n is 2 and m is 1.

8. The compound according to claim 1 or a pharmaceutically acceptable salt thereof, wherein the compound is selected from the group consisting of:

(1) 2,7-dimethyl-4-(naphthalen-1-yloxy)-5,6,7,8-tetrahydro-4H-furo[2,3-c]azepine,
(2) 4-(2,3-dichlorophenyloxy)-2,7-dimethyl-5,6,7,8-tetrahydro-4H-furo[2,3-c]azepine,
(3) 4-(3-bromo-2-chlorophenyloxy)-7-methyl-5,6,7,8-tetrahydro-4H-furo[2,3-c]azepine,
(4) 7-methyl-4-(naphthalen-1-yloxy)-5,6,7,8-tetra-hydro-4H-furo[2,3-c]azepine,
(5) 4-(2,3-dichlorophenyloxy)-7-methyl-5,6,7,8-tetrahydro-4H-furo[2,3-c]azepine,
(6) 4-(3-bromo-2-chlorophenyloxy)-2,7-dimethyl-5,6,7,8-tetrahydro-4H-furo[2,3-c]azepine,
(7) 4-(2-chloro-4-carbamoylphenyloxy)-7-methyl-5,6,7,8-tetrahydro-4H-furo[2,3-c]azepine,
(8) (+)-4-(3-bromo-2-chlorophenoxy)-7-methyl-5,6,7,8-tetrahydro-4H-furo[2,3-c]azepine,
(9) (+)-4-(2,3-dichlorophenoxy)-7-methyl-5,6,7,8-tetrahydro-4H-furo[2,3-c]azepine,
(10) (+)-2,7-dimethyl-4-(naphthalen-1-yloxy)-5,6,7,8-tetrahydro-4H-furo[2,3-c]azepine,
(11) 4-(Naphthalen-1-yloxy)-2-methyl-5,6,7,8-tetrahydro-4H-furo[2,3-c]azepine,
(12) 4-(2-Bromophenyloxy)-5,6,7,8-tetrahydro-4H-furo[2,3-c]azepine,
(13) 4-(3-Bromophenylox)-5,6,7,8-tetrahydro-4H-furo[2,3-c]azepine,
(14) 4-(4-Cyanonaphthalen-1-yloxy)-5,6,7,8-tetrahydro-4H-furo[2,3-c]azepine,
(15) 4-(4-Bromonapthalen-1-yloxy)-5,6,7,8-tetrahydro-4H-furo[2,3-c]azepine,
(16) 4-(4-Carbamoylnaphthalen-1-yloxy)-5,6,7,8-tetrahydro-4H-furo[2,3-c]azepine,
(17) 4-(4-Bromonaphthalen-1-yloxy)-2-methyl-5,6,7,8-tetrahydro-4H-furo[2,3-c]azepine,
(18) 4-(2,3-Dichlorophenyloxy)-2-methyl-5,6,7,8-tetrahydro-4H-furo[2,3-c]azepine,
(19) 4-(2-Bromophenyloxy-2-methyl-5,6,7,8-tetrahydro-4H-furo[2,3-c]azepine,
(20) 4-(3-Bromophenyloxy)-2-methyl-5,6,7,8-tetrahydro-4H-furo[2,3-c]azepine,
(21) 4-(4-Carbamoyl-2-chlorophenyloxy)-5,6,7,8-tetrahydro-4H-furo[2,3-c]azepine,
(22) 4-(Benzothiophen-7-yloxy)-5,6,7,8-tetrahydro-4H-furo[2,3-c]azepine,
(23) 4-(4-Bromo-2-(trifluoromethyl)phenyloxy)-5,6,7,8-tetrahydro-4H-furo[2,3-c]azepine,
(24) 4-(4-Methylnaphthalen-1-yloxy)-2-methyl-5,6,7,8-tetrahydro-4H-furo[2,3-c]azepine,
(25) 4-(4-Cyanonaphthalen-1-yloxy)-2-methyl-5,6,7,8-tetrahydro-4H-furo[2,3-c]azepine,
(26) 4-(3-Bromo-2,5-dichlorophenyloxy)-2-methyl-5,6,7,8-tetrahydro-4H-furo[2,3-c]azepine,
(27) 4-(4-Benzyloxy-3-bromo-2-chlorophenyloxy)-5,6,7,8-tetrahydro-4H-furo[2,3-c]azepine.

9. A pharmaceutical composition comprising the compound of claim 1 or a pharmaceutically acceptable salt thereof as an active ingredient, and a pharmaceutically acceptable carrier.

10. A Method of treating depression, panic disorder, anxiety, obsessive-compulsive disorder, chronic pain, fibromyalgia, obesity, stress urinary incontinence, or overactive bladder, comprising administering an effective amount of a pharmaceutical composition of claim 9 to a patient in need thereof.

* * * * *